(12) United States Patent
Jung et al.

(10) Patent No.: US 10,323,031 B2
(45) Date of Patent: Jun. 18, 2019

(54) PESTICIDALLY ACTIVE TETRACYCLIC DERIVATIVES WITH SULFUR CONTAINING SUBSTITUENTS

(71) Applicant: Syngenta Participations AG, Basel (CH)

(72) Inventors: Pierre Joseph Marcel Jung, Stein (CH); Ottmar Franz Hueter, Stein (CH); Andrew Edmunds, Stein (CH); Michel Muehlebach, Stein (CH); Roger Graham Hall, Stein (CH); Jerome Yves Cassayre, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/554,283

(22) PCT Filed: Mar. 7, 2016

(86) PCT No.: PCT/EP2016/054757
§ 371 (c)(1),
(2) Date: Aug. 29, 2017

(87) PCT Pub. No.: WO2016/142326
PCT Pub. Date: Sep. 15, 2016

(65) Prior Publication Data
US 2018/0134697 A1   May 17, 2018

(30) Foreign Application Priority Data

Mar. 12, 2015   (EP) ..................................... 15158762
Jul. 31, 2015   (EP) ..................................... 15179249

(51) Int. Cl.
*C07D 471/04* (2006.01)
*A01N 43/90* (2006.01)
*C07D 519/00* (2006.01)

(52) U.S. Cl.
CPC ........... *C07D 471/04* (2013.01); *A01N 43/90* (2013.01); *C07D 519/00* (2013.01)

(58) Field of Classification Search
CPC ..... C07D 471/04; C07D 519/00; A01N 43/90
See application file for complete search history.

(56) References Cited

U.S. PATENT DOCUMENTS

2014/0194290 A1   7/2014   Takahashi et al.
2014/0364444 A1   12/2014  Takyo et al.

FOREIGN PATENT DOCUMENTS

DE          3445299       *   6/1986
DE          3445299 A1        6/1986

OTHER PUBLICATIONS

Extended European Search Report EP 15158762.3.
International Search Report and Written Opinion for PCT/EP2016/054757, dated Jun. 15, 2016.

* cited by examiner

*Primary Examiner* — D Margaret M Seaman
(74) *Attorney, Agent, or Firm* — BakerHostetler; Toni-Junell Herbert

(57) ABSTRACT

Compounds of formula I (I), wherein the substituents are as defined in claim 1, and the agrochemically acceptable salts, stereoisomers, enantiomers, tautomers and N-oxides of those compounds, can be used as insecticides and can be prepared in a manner known per se.

17 Claims, No Drawings

PESTICIDALLY ACTIVE TETRACYCLIC DERIVATIVES WITH SULFUR CONTAINING SUBSTITUENTS

RELATED APPLICATION INFORMATION

This application is a 371 of International Application No. PCT/EP2016/054757, filed 7 Mar. 2016, which claims priority to EP Patent Application No. 15 158762.3 filed 12 Mar. 2015; and EP Patent Application No. 15 179249.6 filed 31 Jul. 2015, the contents of which are incorporated herein by reference herein.

The present invention relates to pesticidally active, in particular insecticidally active tetracyclic derivatives containing sulfur substituents, to compositions comprising those compounds, and to their use for controlling animal pests (including arthropods and in particular insects or representatives of the order Acarina).

Heterocyclic compounds with pesticidal action are known and described, for example, in WO 2012/086848 and WO 2013/018928.

There have now been found novel pesticidally active tetracyclic derivatives with a sulfur containing bicyclic moiety.

The present invention accordingly relates to compounds of formula I,

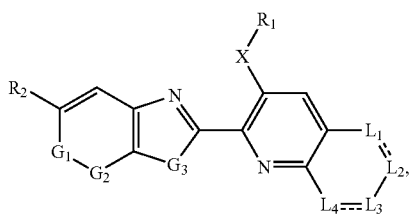

wherein

A is CH or N;
X is S, SO or $SO_2$;
$R_1$ is $C_1$-$C_6$alkyl, $C_2$-$C_6$alkenyl, $C_2$-$C_6$haloalkenyl, $C_2$-$C_6$alkynyl, $C_1$-$C_4$haloalkyl, $C_3$-$C_6$cycloalkyl, $C_3$-$C_6$cycloalkyl-$C_1$-$C_4$alkyl; or is $C_3$-$C_6$cycloalkyl mono- or polysubstituted by substituents selected from the group consisting of halogen, cyano, $C_1$-$C_4$haloalkyl and $C_1$-$C_4$alkyl; or is $C_3$-$C_6$cycloalkyl-$C_1$-$C_4$alkyl mono- or polysubstituted by substituents selected from the group consisting of halogen, cyano, $C_1$-$C_4$haloalkyl and $C_1$-$C_4$alkyl;

$R_2$ is hydrogen, halogen, $C_1$-$C_4$haloalkylsulfanyl, $C_1$-$C_4$haloalkylsulfinyl, $C_1$-$C_4$haloalkylsulfonyl, $O(C_1$-$C_4$haloalkyl), —$SF_5$, —$C(O)C_1$-$C_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano, $C_1$-$C_4$haloalkyl and $C_1$-$C_4$alkyl;

$G_1$ is $NR_4$ and $G_2$ is $C(Y)$; or
$G_1$ is $C(Y)$ and $G_2$ is $NR_5$;
Y is O or S;
$G_3$ is $NR_6$;
$R_6$ is $C_1$-$C_4$alkyl which can be mono- or polysubstituted by substituents selected from the group consisting of halogen and $C_1$-$C_2$alkylsulfinyl;

$R_4$ is hydrogen, $C_1$-$C_6$alkyl, $C_1$-$C_6$haloalkyl, or are $C_3$-$C_6$cycloalkyl which can be mono- or poly substituted by $R_7$; or are $C_3$-$C_6$cycloalkyl-$C_1$-$C_4$alkyl which can be mono- or polysubstituted by $R_7$; or $R_4$ is $C_1$-$C_4$alkyl substituted by cyano, $C_1$-$C_4$alkylsulfanyl, $C_1$-$C_4$alkylsulfonyl, $C_1$-$C_4$alkylsulfinyl, $C_1$-$C_4$alkoxy, $C_1$-$C_4$alkoxy $C_1$-$C_4$alkoxy, $C_3$-$C_6$cycloalkyl or by phenyl which itself can be mono- or polysubstituted by substituents selected from the group consisting of halogen, $C_1$-$C_4$alkyl, $C_1$-$C_4$haloalkyl and $C_1$-$C_4$alkoxy; or $R_4$ is $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_4$alkoxy $C_1$-$C_4$alkyl , $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl; or $R_4$ is $C_2$-$C_6$alkenyl substituted by $R_{11}$ or $C_2$-$C_6$alkynyl substituted by $R_{11}$; or $R_4$ is a five- to six-membered, aromatic, partially saturated or fully saturated ring system, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl and —$C(O)C_1$-$C_4$alkyl, $C_1$-$C_4$haloalkylsulfanyl, $C_1$-$C_4$haloalkylsulfinyl, $C_1$-$C_4$haloalkylsulfonyl and —$C(O)C_1$-$C_4$haloalkyl; and said ring system can contain 1, 2 or 3 heteroatoms selected from the group consisting of nitrogen, oxygen and sulphur, where said ring system may not contain more than one oxygen atom and not more than one sulfur atom;

$R_5$ is hydrogen, $C_1$-$C_6$alkyl, $C_1$-$C_6$haloalkyl, or are $C_3$-$C_6$cycloalkyl which can be mono- or polysubstituted by $R_7$; or are $C_3$-$C_6$cycloalkyl-$C_1$-$C_4$alkyl which can be mono- or polysubstituted by $R_7$; or $R_5$ is $C_1$-$C_4$alkyl substituted by cyano, $C_1$-$C_4$alkylsulfanyl, $C_1$-$C_4$alkylsulfonyl, $C_1$-$C_4$alkylsulfinyl, $C_1$-$C_4$alkoxy, $C_1$-$C_4$alkoxy $C_1$-$C_4$alkoxy, $C_3$-$C_6$cycloalkyl or by phenyl which itself can be mono- or polysubstituted by substituents selected from the group consisting of halogen, $C_1$-$C_4$alkyl, $C_1$-$C_4$haloalkyl and $C_1$-$C_4$alkoxy; or $R_5$ is $C_2$-$C_6$alkenyl, $C_2$-$C_6$haloalkenyl, $C_2$-$C_6$alkynyl, $C_2$-$C_6$haloalkynyl, $C_1$-$C_6$haloalkoxy, $C_1$-$C_6$alkoxy, $C_1$-$C_4$alkoxy $C_1$-$C_4$alkyl, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl; or $R_5$ is $C_2$-$C_6$alkenyl substituted by $R_{11}$ or $C_2$-$C_6$alkynyl substituted by $R_{11}$; or $R_5$ is a five- to six-membered, aromatic, partially saturated or fully saturated ring system, said ring system can be mono- or polysubstituted by substituents selected from the group consisting of halogen, cyano, nitro, $C_2$-$C_6$alkenyl, $C_2$-$C_6$haloalkenyl, $C_2$-$C_6$alkynyl, $C_2$-$C_6$haloalkynyl, $C_1$-$C_4$alkoxy $C_1$-$C_4$alkyl, $C_1$-$C_4$alkyl, $C_1$-$C_4$haloalkyl, $C_1$-$C_4$haloalkoxy, $C_1$-$C_4$alkoxy, $C_1$-$C_4$alkylsulfanyl, $C_1$-$C_4$alkylsulfinyl, $C_1$-$C_4$alkylsulfonyl and —$C(O)C_1$-$C_4$alkyl, $C_1$-$C_4$haloalkylsulfanyl, $C_1$-$C_4$haloalkylsulfinyl, $C_1$-$C_4$haloalkylsulfonyl and —$C(O)C_1$-$C_4$haloalkyl; and said ring system can contain 1, 2 or 3 heteroatoms selected from the group consisting of nitrogen, oxygen and sulphur, where said ring system may not contain more than one oxygen atom and not more than one sulfur atom;

$R_7$ is cyano, halogen, $C_1$-$C_6$alkyl or $C_1$-$C_4$haloalkyl;

$L_1$, $L_2$, $L_3$ and $L_4$ form together with the two carbon atoms to which $L_1$ and $L_4$ are attached, an aromatic, partially saturated or fully saturated carbocyclic or heterocyclic ring system; wherein $L_1$ is nitrogen, S(O)n, oxygen, N—$R_{10a}$ or C($R_{10a}$)$_m$;
$L_2$ is nitrogen, S(O)n, oxygen, N—$R_{10b}$ or C($R_{10b}$)$_m$;
$L_3$ is nitrogen, S(O)n, oxygen, N—$R_{10c}$ or C($R_{10c}$)$_m$;
$L_4$ is nitrogen, S(O)n, oxygen, a direct bond, N—$R_{10d}$ or C($R_{10d}$)$_m$; with the provisos that no more than 2 substituents selected from $L_1$, $L_2$, $L_3$ and $L_4$ can be oxygen or sulfur; and if two L groups are oxygen, they are not adjacent to each other; and no more than three L groups can be nitrogen;

n is 0, 1 or 2;
m is 1 or 2;

$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy $C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$alkoxycarbonyl, $C_2$-$C_6$haloalkylcarbonyl, $C_2$-$C_6$haloalkoxycarbonyl, ($C_1$-$C_6$ alkyl)NH, ($C_1$-$C_6$ alkyl)$_2$N, ($C_1$-$C_6$ cycloalkyl)NH, ($C_1$-$C_6$ cycloalkyl)$_2$N, $C_1$-$C_6$alkylcarbonylamino, $C_1$-$C_6$ cycloalkylcarbonylamino or —$SF_5$; additionally one of $R_{10a}$, $R_{10b}$, $R_{10c}$ and $R_{10d}$ can be oxo; or $R_{10a}$, $R_{10b}$, $R_{10c}$, and $R_{10d}$, independently from each other, are $C_3$-$C_6$cycloalkyl mono- to polysubstituted by substituents selected from the group consisting of halogen, $C_1$-$C_4$haloalkyl, $C_1$-$C_4$alkyl and cyano; or $R_{10a}$, $R_{10b}$, $R_{10c}$, and $R_{10d}$, independently from each other, are phenyl witch can be mono- to polysubstituted by substituents selected from the group consisting of halogen, $C_1$-$C_4$haloalkyl, $C_1$-$C_4$alkyl and cyano; and $R_{11}$ is nitro, phenyl, cyano, $C_1$-$C_4$alkoxy, $C_1$-$C_4$ alkoxy $C_1$-$C_4$alkoxy, $C_1$-$C_4$alkylsulfanyl, $C_1$-$C_4$alkylsulfonyl, $C_1$-$C_4$alkylsulfinyl, $C_1$-$C_4$haloalkylsulfanyl, $C_1$-$C_4$haloalkylsulfonyl or $C_1$-$C_4$haloalkylsulfinyl; and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

m is 1 or 2 depending on the hybridization of the carbon atom.

If m is 2 in the definition C($R_{10a}$)$_m$ $R_{10a}$ can be the same or different; for example one $R_{10a}$ can be hydrogen and the other methyl. This is also valid for the definitions of C($R_{10b}$)$_m$, C($R_{10c}$)$_m$ and C($R_{10d}$)$_m$.

The alkyl groups occurring in the definitions of the substituents can be straight-chain or branched and are, for example, but are not limited to, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, but are not limited to, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl.

Alkoxy is, for example, but are not limited to, methoxy, ethoxy, propoxy, i-propoxy, n-butoxy, isobutoxy, sec-butoxy and tert-butoxy and also the isomeric pentyloxy and hexyloxy radicals.

Alkoxyalkyl groups preferably have a chain length of 1 to 6 carbon atoms.

Alkoxyalkyl is, for example, but are not limited to, methoxymethyl, methoxyethyl, ethoxymethyl, ethoxyethyl, n-propoxymethyl, n-propoxyethyl, isopropoxymethyl or isopropoxyethyl.

Alkoxycarbonyl is for example, but are not limited to, methoxycarbonyl (which is $C_1$alkoxycarbonyl), ethoxycarbonyl, propoxycarbonyl, isopropoxycarbonyl, n-butoxycarbonyl, tert-butoxycarbonyl, n-pentoxycarbonyl or hexoxycarbonyl.

The cycloalkyl groups preferably have from 3 to 6 ring carbon atoms, for example, but are not limited to, cyclopropyl, cyclobutyl, cyclopentyl and cyclohexyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_4$ alkynyl" and "$C_2$-$C_3$alkynyl" can be formed accordingly. Examples of $C_2$-$C_6$alkynyl include, but are not limited to, ethynyl, prop-1-ynyl, but-1-ynyl, but-2-ynyl.

As used herein, the term "$C_2$-$C_6$alkenyl" refers to a straight or branched hydrocarbon chain radical group consisting solely of carbon and hydrogen atoms, containing at least one double bond, having from two to six carbon atoms, and which is attached to the rest of the molecule by a single bond. The term "$C_2$-$C_4$alkenyl" and "$C_2$-$C_3$alkenyl" can be formed accordingly. Examples of $C_2$-$C_6$alkenyl include, but are not limited to, prop-1-enyl, but-1-enyl, but-2-enyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is bond, an aromatic, partially saturated or fully saturated ring system", the ring system is preferably a group having 5 to 6 ring carbon atoms which are saturated, unsaturated or partially saturated, for example, but are not limited to phenyl, cyclopentyl and cyclohexenyl or if the ring system is an heterocyclic ring system, this ring system is preferably a group comprising 5 to 6 carbon atoms in the ring, which are saturated, unsaturated or partially saturated, for example, but are not limited to pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; pyrrolidinyl, piperidinyl; pyrrolidinyl-2-one; piperidinyl-2-one.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, di- or tri-substituted.

An example for an aromatic, partially saturated or fully saturated carbocyclic or heterocyclic ring system wherein one of $R_{10a}$, $R_{10b}$, $R_{10c}$ or $R_{10d}$ can represent oxo, is the group $J_{15}$:

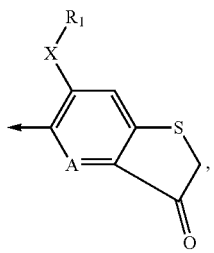

wherein X, $R_1$ and A are as defined under formula I above.

The compounds of formula I according to the invention also include hydrates which may be formed during the salt formation.

In preferred compounds of formula I, $R_2$ is hydrogen, halogen, $C_1$-$C_4$haloalkylsulfanyl, $C_1$-$C_4$haloalkylsulfinyl, $C_1$-$C_4$haloalkylsulfonyl, O($C_1$-$C_4$haloalkyl), —SF$_5$, —C(O)C$_1$-C$_4$haloalkyl, cyano, $C_1$-$C_6$haloalkyl or is $C_1$-$C_6$haloalkyl substituted by one or two substituents selected from the group consisting of hydroxyl, methoxy and cyano; or is $C_3$-$C_6$cycloalkyl which can be mono- or polysubstituted by substituents selected from the group consisting of halogen, cyano and $C_1$-$C_4$alkyl;

$R_4$ and $R_5$ are, independently from each other, hydrogen, $C_1$-$C_6$alkyl, $C_1$-$C_6$haloalkyl, or are $C_3$-$C_6$cycloalkyl which can be mono- or poly substituted by $R_7$; or are $C_3$-$C_6$cycloalkyl-$C_1$-$C_4$alkyl which can be mono- or polysubstituted by $R_7$; or $R_4$ and $R_5$ are, independently from each other, $C_1$-$C_4$alkyl substituted by cyano or by phenyl which itself can be mono- or polysubstituted by substituents selected from the group consisting of halogen, $C_1$-$C_4$alkyl, $C_1$-$C_4$haloalkyl and $C_1$-$C_4$alkoxy;

$R_4$ and $R_5$ are, independently from each other, $C_2$-$C_6$alkenyl, $C_2$-$C_6$haloalkenyl, $C_2$-$C_6$alkynyl, $C_2$-$C_6$alkynyl, $C_1$-$C_6$haloalkoxy, $C_1$-$C_6$alkoxy, $C_1$-$C_6$alkylsulfanyl, $C_1$-$C_4$alkylsulfonyl, $C_1$-$C_6$alkylsulfinyl, $C_1$-$C_6$haloalkylsulfanyl, $C_1$-$C_6$haloalkylsulfonyl, $C_1$-$C_6$haloalkylsulfinyl, amine or hydroxyl;

$R_7$ is cyano, halogen or $C_1$-$C_2$haloalkyl;

$L_1$, $L_2$, $L_3$ and $L_4$ form together with the two carbon atoms to which $L_1$ and $L_4$ are attached, an aromatic, partially saturated or fully saturated carbocyclic or heterocyclic ring system; wherein $L_1$ is nitrogen, sulfur, oxygen, N—$R_{10a}$ or C—$R_{10a}$;

$L_2$ is nitrogen, sulfur, oxygen, N—$R_{10b}$ or C—$R_{10b}$;

$L_3$ is nitrogen, sulfur, oxygen, N—$R_{10c}$ or C—$R_{10c}$;

$L_4$ is nitrogen, sulfur, oxygen, a direct bond or C—$R_{10d}$; with the provisos that no more than 2 substituents selected from $L_1$, $L_2$, $L_3$ and $L_4$ can be oxygen or sulfur; and if two L groups are oxygen, they are not adjacent to each other; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$ alkenyl, $C_2$-$C_6$ alkynyl, $C_3$-$C_6$ cycloalkyl, $C_1$-$C_6$ haloalkyl, $C_2$-$C_6$haloalkenyl, $C_2$-$C_6$haloalkynyl, $C_3$-$C_6$ halocycloalkyl, $C_1$-$C_6$ alkoxy, $C_1$-$C_6$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$alkylcarbonyl, $C_2$-$C_6$ alkoxycarbonyl or —SF$_5$; additionally one of $R_{10a}$, $R_{10b}$, $R_{10c}$ and $R_{10d}$ can be oxo.

A preferred group of compounds of formula I is represented by the compounds of formula I-1

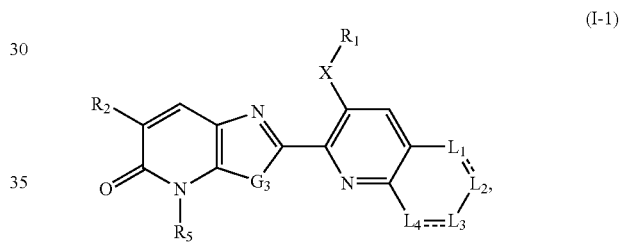

wherein the substituents X, A, $R_1$, $R_2$, $R_5$, $G_3$, $L_1$, $L_2$, $L_3$ and $L_4$ are as defined under formula I above and Y is O.

Embodiment (A1):

Preferred are compounds of formula I-1, wherein

A is C—H or N;

$R_1$ is $C_1$-$C_4$alkyl, $C_3$-$C_6$cycloalkyl-$C_1$-$C_4$alkyl or $C_3$-$C_6$cycloalkyl;

$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or is $C_3$-$C_6$cycloalkyl which can be mono- or polysubstituted by substituents selected from the group consisting of halogen, cyano and $C_1$-$C_4$alkyl;

$R_5$, X, $G_3$, $L_1$, $L_2$, $L_3$ and $L_4$ are as defined under formula I above; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl, $C_2$-$C_6$alkoxycarbonyl, —SF$_5$; additionally one of $R_{10a}$, $R_{10b}$, $R_{10c}$ and $R_{10d}$ can be oxo.

Embodiment (A2):
Further preferred are compounds of formula I-1a
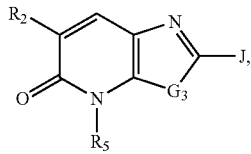
(I-1a)
wherein J is selected from the group consisting of
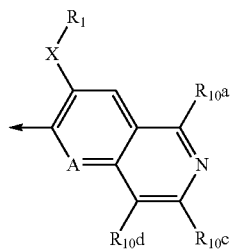
J₁
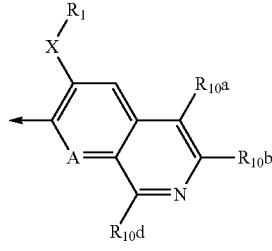
J₂
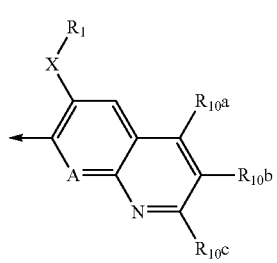
J₃
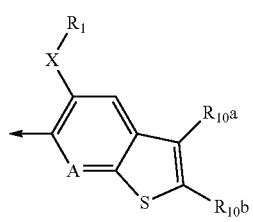
J₄
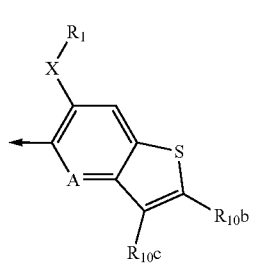
J₅
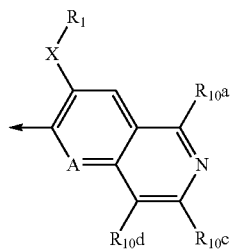
J₆
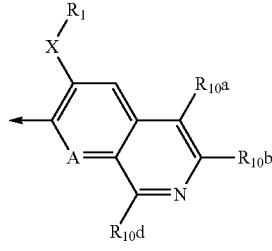
J₇
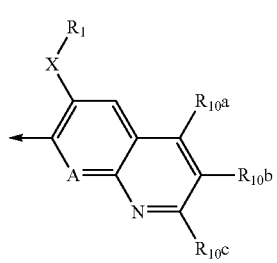
J₈
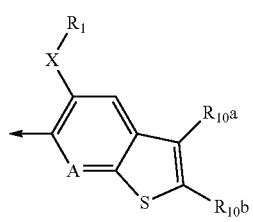
J₉
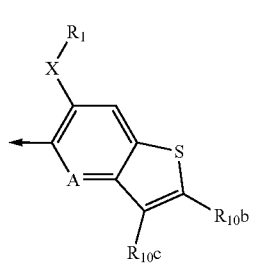
J₁₀
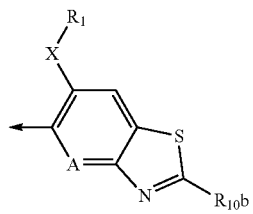
J₁₁

-continued
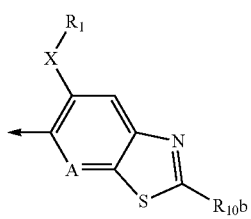
J12
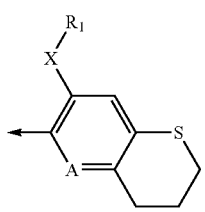
J13
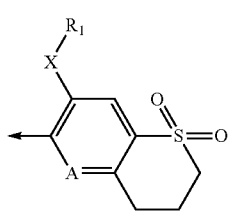
J14
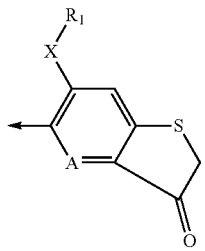
J15
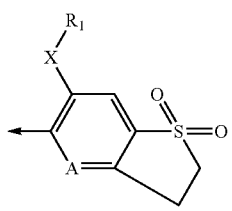
J16
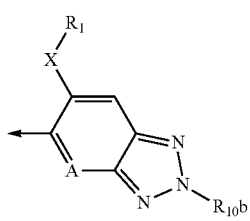
J17
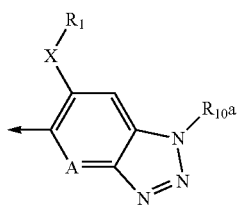
J18
-continued
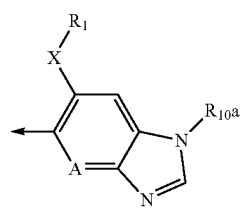
J19
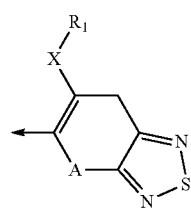
J20
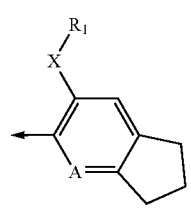
J21
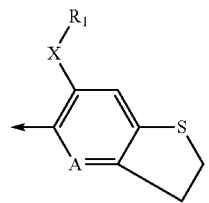
J22
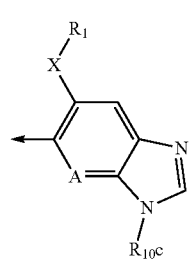
J23
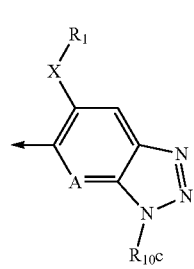
J24
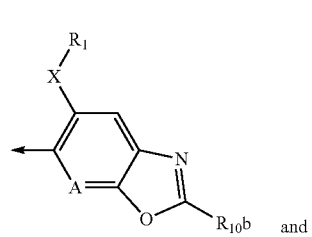 and
J25

-continued

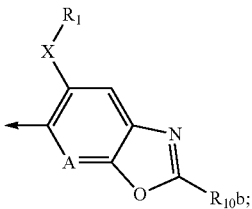

and A, $G_3$, $R_1$, $R_2$, $R_5$, X, $R_{10a}$, $R_{10b}$, $R_{10c}$, $R_{10d}$, are as defined under Embodiment (A1).

Embodiment (A3):
Further preferred are compounds of formula I-1a

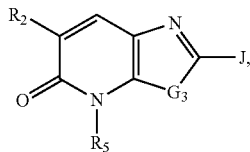
(I-1a)

wherein J is as defined under Embodiment (A2) above and
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;
X and $G_3$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A4):
Further preferred are compounds of formula I-1a

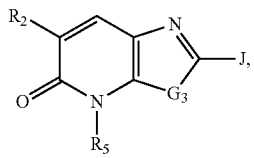
(I-1a)

wherein J is as defined under Embodiment (A2) above and
A is C—H or N;
$R_1$ is $C_1$-$C_4$alkyl;
$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A5):
Further preferred are compounds of formula I-1a

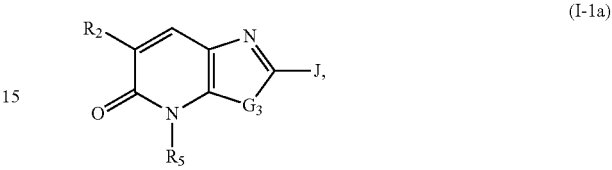
(I-1a)

wherein J is as defined under Embodiment (A2) above and
A is C—H or N;
$R_1$ is $C_1$-$C_4$ alkyl;
$R_2$ is —OCF$_3$, —SCF$_3$, —S(O)CF$_3$, —S(O)$_2$CF$_3$ or CF$_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (A6):
Further preferred are compounds of formula I-1a

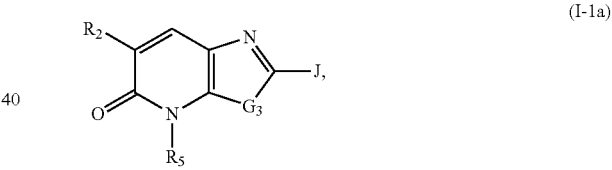
(I-1a)

wherein J is as defined under Embodiment (A2) above and
A is C—H or N;
$R_1$ is ethyl;
$R_2$ is —SCF$_3$, —S(O)CF$_3$, —S(O)$_2$CF$_3$ or CF$_3$;
X is as defined under formula I above; and
$G_3$ is N—$R_6$, wherein $R_6$ is as defined under formula I above; and
$R_{10a}$, $R_{10b}$, $R_{10c}$, and $R_{10d}$, independently from each other, are hydrogen, bromo, chloro, iodo, fluoro, cyano, methyl, ethyl, isopropyl, propyl, trifluoromethyl, CF$_3$CH$_2$—, CH$_3$O, —SCF$_3$, —S(O)CF$_3$ or —S(O)$_2$CF$_3$.

Embodiment (A7):
Further preferred are compounds of formula I-1a

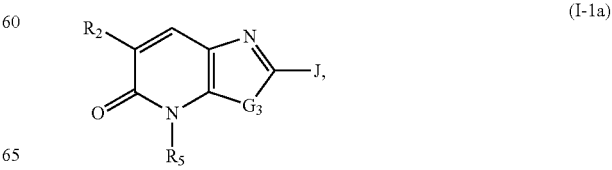
(I-1a)

wherein J is as defined under Embodiment(A2) above and
A is C—H or N;
$R_1$ is ethyl;
$R_2$ is —$SCF_3$, —$S(O)CF_3$, —$S(O)_2CF_3$ or $CF_3$;
X is as defined under formula I above;
$G_3$ is N—$R_6$, wherein $R_6$ is as defined under formula I above; and
$R_{10a}$, $R_{10b}$, $R_{10c}$, and $R_{10d}$ independently from each other, are hydrogen, bromo, chloro, iodo, fluoro, cyano, methyl or trifluoromethyl.

Embodiment (A8):

Further preferred are compounds of formula I-1a

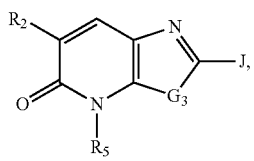

(I-1a)

wherein J is as defined under Embodiment(A2) and
A is C—H or N;
$R_1$ is ethyl;
$R_2$ is $CF_3$;
X is as defined under formula I above;
$G_3$ is N—$R_6$, $R_6$ is as defined under formula I above;
$R_{10a}$, $R_{10b}$, $R_{10c}$, and $R_{10d}$ independently from each other, are hydrogen in all groups J except $J_2$; and
$R_{10a}$, $R_{10b}$, and $R_{10d}$, independently from each other, are hydrogen in $J_2$ and $R_{10c}$ is methyl in $J_2$.

In all of the preferred embodiments of formula I, I-1 and I-1a above, X is preferably S or $SO_2$ and $R_6$ is methyl.

In all of the preferred embodiments of formula I, I-1 and I-1a above, $R_5$ is preferably methyl or ethyl, in particular ethyl.

A further preferred group of compounds of formula I is represented by the compounds of formula I-2

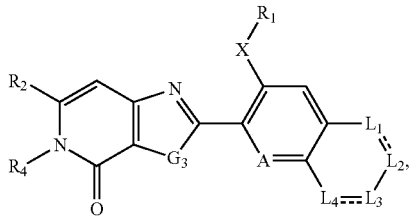

(I-2)

wherein the substituents X, A, $R_1$, $R_2$, $R_4$, $G_3$, $L_1$, $L_2$, $L_3$ and $L_4$ are as defined under formula I above and Y is O.

Embodiment (B1):

Preferred are compounds of formula I-2, wherein
A is C—H or N;
$R_1$ is $C_1$-$C_4$ alkyl, $C_3$-$C_6$ cycloalkyl-$C_1$-$C_4$ alkyl or $C_3$-$C_6$ cycloalkyl;
$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$ cycloalkyl which can be mono- or polysubstituted by substituents selected from the group consisting of halogen, cyano and $C_1$-$C_4$ alkyl;
X and $G_3$ is as defined under formula I above;
$L_1$, $L_2$, $L_3$ and $L_4$ are as defined under formula I above; and $R_{12}$, $R_{10a}$, $R_{10b}$, $R_{10c}$, and $R_{10d}$ independently from each other, are hydrogen, halogen, nitro, cyano, hydroxyl, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl-$C_1$-$C_4$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_3$-$C_6$ cyclohaloalkyl-$C_1$-$C_4$ cycloalkyl, $C_1$-$C_6$ alkoxy, $C_1$-$C_6$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_6$ alkoxycarbonyl, —$SF_5$; additionally one of $R_{10a}$, $R_{10b}$, $R_{10c}$ and $R_{10d}$ can be oxo.

Embodiment (B2):

Further preferred are compounds of formula I-2a

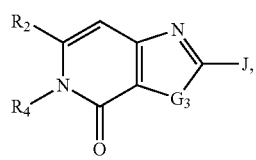

(I-2a)

wherein J is selected from the group consisting of

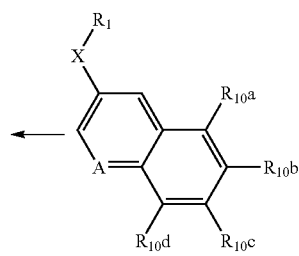

$J_1$

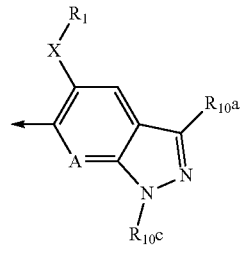

$J_2$

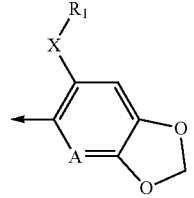

$J_3$

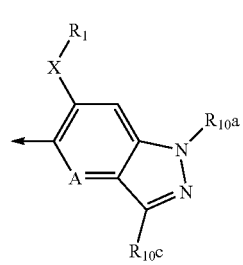

$J_4$

15
-continued
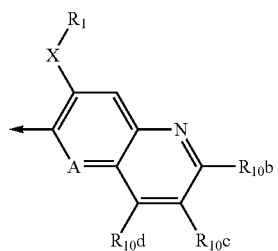
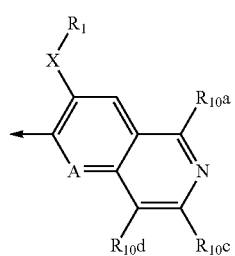
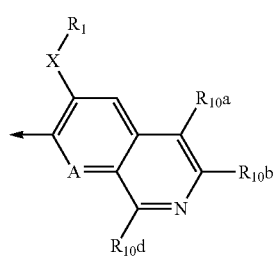
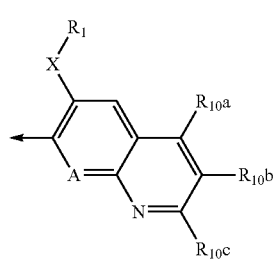
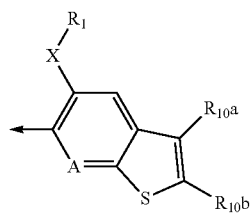
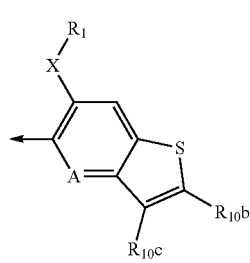
16
-continued
$J_5$
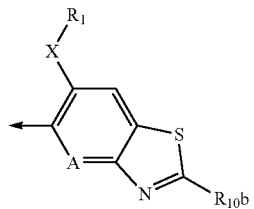
$J_6$
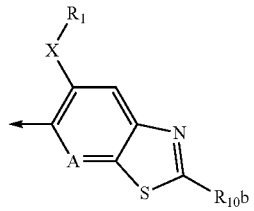
$J_7$
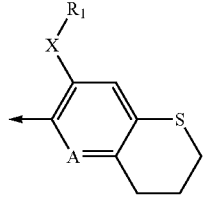
$J_8$
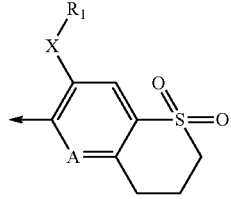
$J_9$
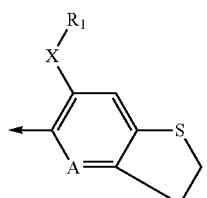
$J_{10}$
$J_{11}$
$J_{12}$
$J_{13}$
$J_{14}$
$J_{15}$
$J_{16}$
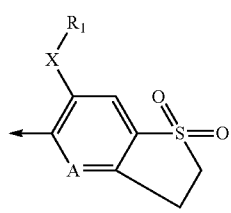
$J_{17}$
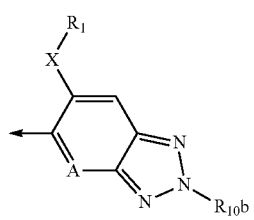

-continued

J18 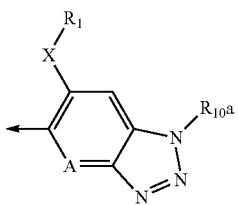

J19 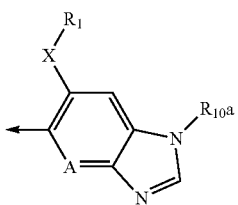

J20 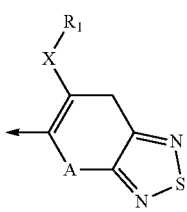

J21 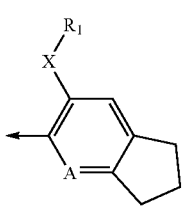

J22 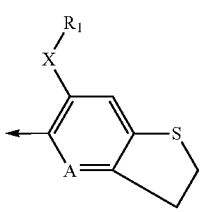

J23 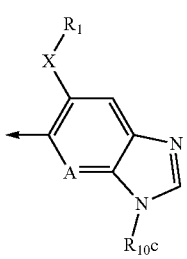

J24 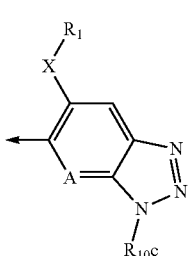

-continued

J25 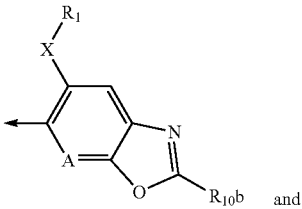 and

J26 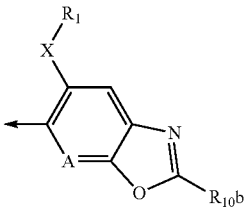

and A, $G_3$, $R_1$, $R_2$, X, $R_{10a}$, $R_{10b}$, $R_{10c}$, $R_{10d}$, are as defined under Embodiment(B1).

Embodiment (B3):
Further preferred are compounds of formula I-2a

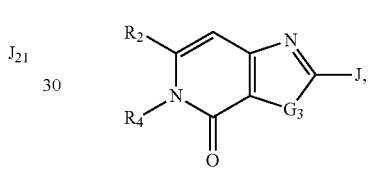
(I-2a)

wherein J is as defined under Embodiment(B2) and
A is C—H or N;
$R_1$ is $C_1$-$C_4$alkyl, $C_3$-$C_6$cycloalkyl-$C_1$-$C_4$alkyl or $C_3$-$C_6$cycloalkyl;
$R_2$ is halogen, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $C_1$-$C_4$haloalkyl, cyano or $C_3$-$C_6$cycloalkyl;
X and $G_3$ is as defined under formula I above; and
$R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (B4):
Further preferred are compounds of formula I-2a

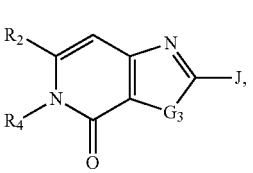
(I-2a)

wherein J is as defined under Embodiment(B2) and
A is C—H or N;
$R_1$ is $C_1$-$C_4$alkyl;

$R_2$ is $C_1$-$C_4$haloalkylsulfanyl, $C_1$-$C_4$haloalkylsulfinyl, $C_1$-$C_4$haloalkylsulfonyl, $C_1$-$C_4$haloalkoxy or $C_1$-$C_4$haloalkyl;

X is as defined under formula I above; and $G_3$ is N—$R_6$, wherein $R_6$ is as defined under formula I above; and $R_{10a}$, $R_{10b}$, $R_{10c}$, and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (B5):

Further preferred are compounds of formula I-2a

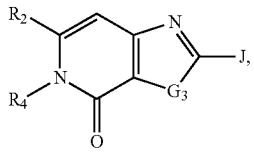
(I-2a)

wherein J is as defined under Embodiment(B2) and

A is C—H or N;

$R_1$ is $C_1$-$C_4$ alkyl;

$R_2$ is —$OCF_3$, —$SCF_3$, —$S(O)CF_3$, —$S(O)_2CF_3$ or $CF_3$;

X is as defined under formula I above; and $G_3$ is N—$R_6$, wherein $R_6$ is as defined under formula I above; and $R_{10a}$, $R_{10b}$, $R_{10c}$, and $R_{10d}$, independently from each other, are hydrogen, halogen, cyano, $C_1$-$C_6$alkyl, $C_2$-$C_6$alkenyl, $C_2$-$C_6$alkynyl, $C_1$-$C_6$haloalkyl, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

Embodiment (B6):

Further preferred are compounds of formula I-2a

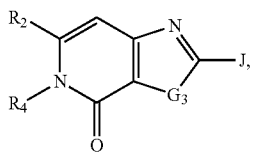
(I-2a)

wherein J is as defined under Embodiment(B2) and

A is C—H or N;

$R_1$ is ethyl;

$R_2$ is —$SCF_3$, —$S(O)CF_3$, —$S(O)_2CF_3$ or $CF_3$;

X is as defined under formula I above; and $G_3$ is N—$R_6$, wherein $R_6$ is as defined under formula I above; and $R_{10a}$, $R_{10b}$, $R_{10c}$, and $R_{10d}$, independently from each other, are hydrogen, bromo, chloro, iodo, fluoro, cyano, methyl, ethyl, isopropyl, propyl, trifluoromethyl, $CF_3CH_2$—, $CH_3O$, —$SCF_3$, —$S(O)CF_3$ or —$S(O)_2CF_3$.

Embodiment (B7):

Further preferred are compounds of formula I-2a

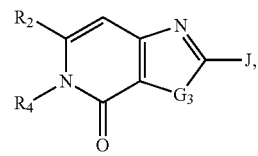
(I-2a)

wherein J is as defined under Embodiment(B2) and

A is C—H or N;

$R_1$ is ethyl;

$R_2$ is —$SCF_3$, —$S(O)CF_3$, —$S(O)_2CF_3$ or $CF_3$;

X is as defined under formula I above;

$G_3$ is N—$R_6$, wherein $R_6$ is as defined under formula I above; and $R_{10a}$, $R_{10b}$, $R_{10c}$, and $R_{10d}$, independently from each other, are hydrogen, Br, Cl, I, F, cyano, methyl, or trifluoromethyl.

Embodiment (B8):

Further preferred are compounds of formula I-2a

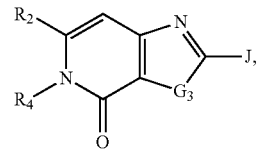
(I-2a)

wherein J is as defined under Embodiment(B2) and

A is C—H or N;

$R_1$ is ethyl;

$R_2$ is $CF_3$;

X is as defined under formula I above;

$G_3$ is N—$R_6$, $R_6$ is as defined under formula I above;

$R_{10a}$, $R_{10b}$, $R_{10c}$, and $R_{10d}$, independently from each other, are hydrogen in all groups J except $J_2$ ; and $R_{10a}$, $R_{10b}$, and $R_{10d}$, independently from each other, are hydrogen in $J_2$ and $R_{10c}$ is methyl in $J_2$.

In all of the preferred embodiments of formula I, I-2 and I-2a above, X is preferably S or $SO_2$ and $R_6$ is methyl.

In all of the preferred embodiments of formula I, I-2 and I-2a above, $R_4$ is preferably methyl or ethyl, in particular ethyl.

In all of the preferred embodiments A2-A8 and B2-B8, J is preferably selected from $J_1$, $J_2$, $J_3$, $J_4$, $J_5$, $J_6$, $J_{12}$, $J_{17}$, $J_{18}$, $J_{24}$, $J_{19}$, $J_{20}$ and $J_{23}$, in particular in all of the preferred embodiments A2-A8 and B2-B8, J is $J_1$.

Embodiment (B9):

More preferred are compounds of formula I-2a

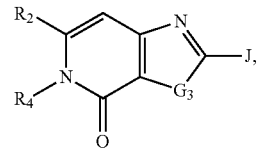
(I-2a)

wherein J is selected from the group consisting of

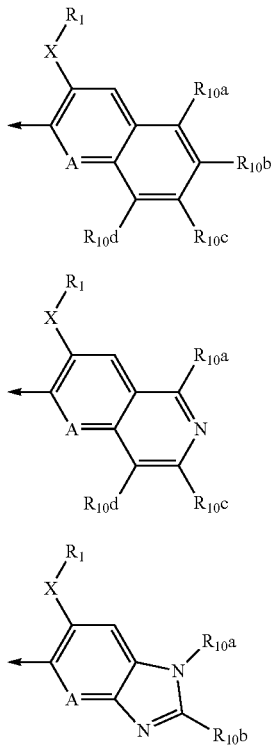

wherein
  A is CH or N;
  $R_2$ is $C_1$-$C_2$haloalkyl;
  $R_4$ is $C_1$-$C_4$alkyl; and
  $R_{10a}$, $R_{10b}$, $R_{10c}$, and $R_{10d}$, independently from each other, are hydrogen, $C_1$-$C_2$haloalkyl or $C_1$-$C_2$alkyl.

Embodiment (B10):

Even more preferred are compounds of formula I-2a

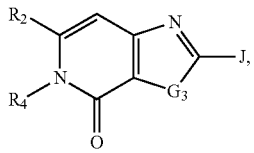
(I-2a)

wherein J is selected from the group consisting of

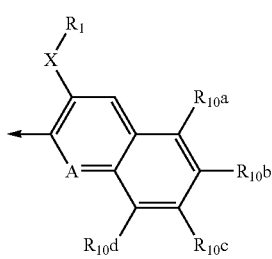

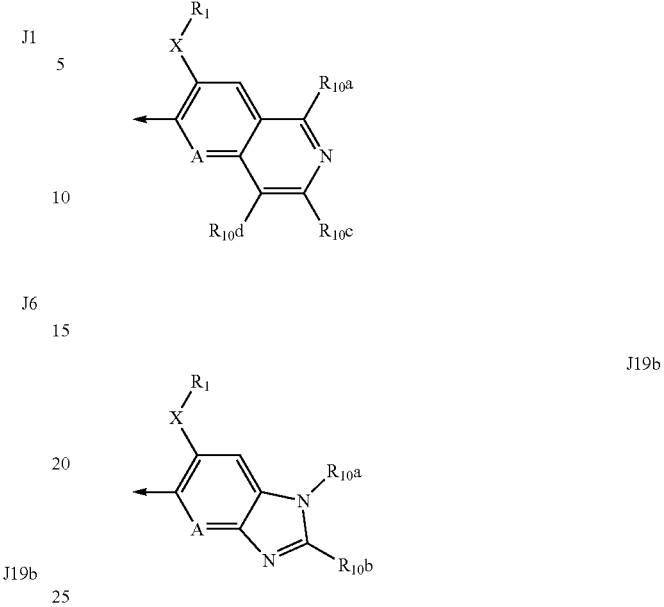

wherein
  A is CH or N;
  $R_2$ is trifluoromethyl;
  $R_4$ is methyl or ethyl; and
  $R_{10a}$, $R_{10b}$, $R_{10c}$, and $R_{10d}$, independently from each other, are hydrogen, trifluoromethyl or methyl.

The process according to the invention for preparing compounds of formula (I) is carried out by methods known to those skilled in the art, or described for example in WO 2009/131237, WO 2011/043404, WO 2011/040629, WO 2010/125985, WO 2012/086848, WO 2013/018928, WO 2013/191113, WO 2013/180193 and WO 2013/180194, and comprises reaction of a compound of formula II,

(II)

wherein Q is the group

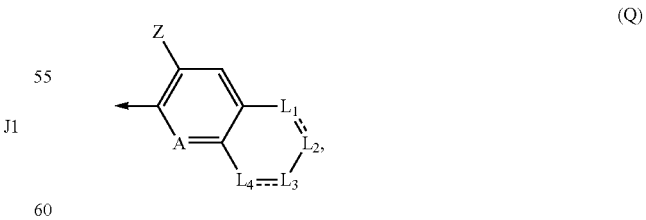
(Q)

wherein Z is X—$R_1$ or a leaving group, for example a halogen, and wherein X, $R_1$, $L_1$, $L_2$, $L_3$, $L_4$ and A are as described under formula I above, and wherein the arrow in the radical Q shows the point of attachment to the carbon atom of the carboxyl group in the compound of formula II, with a compound of formula III,

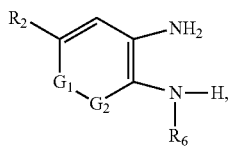
(III)

wherein R₆, R₂, G₁ and G₂ are as described under formula I above, in the presence of a dehydrating agent, such as for example polyphosphoric acid at temperature between 150° C. to 250° C., to yield compounds of formula Ia, wherein the substituents are as described above and under formula I. Such processes are well known and have been described for example in WO 2008/128968 or WO 2006/003440. The process is summarized in scheme 1 for compounds of formula Ia:

Scheme 1

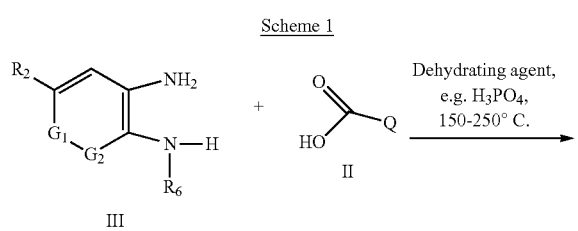

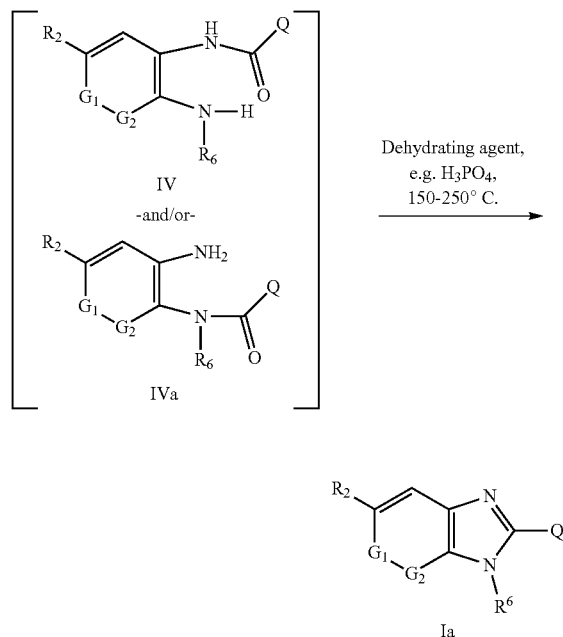

As can be seen in scheme 1, the formation of compounds of formula Ia occurs through the intermediacy of a compound of formula IV (and/or its position isomer IVa). Intermediate IV or intermediate IVa may form as a pure entity, or intermediates IV and IVa may arise as a mixture of regioisomeric acylation products. It is in many cases advantageous to thus prepare compounds of formula (I) through such intermediates IV/IVa, which may be isolated and optionally purified. This is illustrated for compounds of formula Ia in scheme 2:

Scheme 2

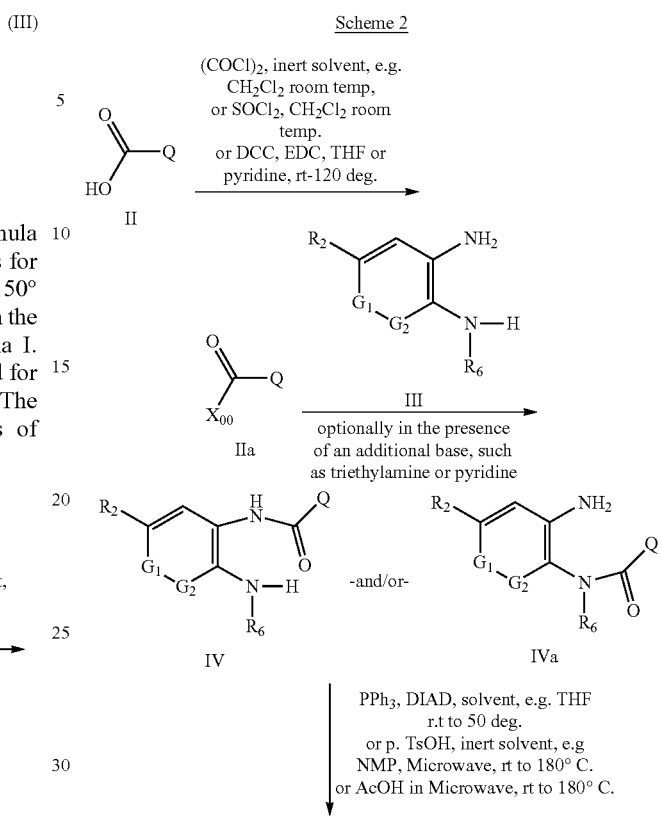

wherein:

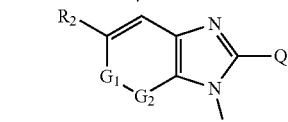

$X_{00}$ = Halogen,

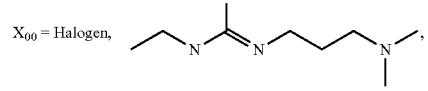

$X_{01}$

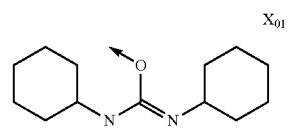

$X_{02}$

Compounds of the formula IV and/or IVa (or a mixture thereof), or a salt thereof, wherein Q is as defined above, and wherein R₆, R₂, G₁ and G₂ are as described under formula I above, may be prepared by i) activation of compound of formula II, wherein Q is as defined above, by methods known to those skilled in the art and described in, for example, Tetrahedron, 2005, 61 (46), 10827-10852, to form an activated species IIa, wherein Q is as defined above and wherein $X_{00}$ is halogen, preferably chlorine. For example, compounds IIa where $X_{00}$ is halogen, preferably chlorine, are formed by treatment of II with, for example, oxallyl chloride (COCl)₂ or thionyl chloride SOCl₂ in the presence of catalytic quantities of N,N-dimethylformamide DMF in inert solvents such as methylene chloride CH₂Cl₂ or tetrahydrofuran THF at temperatures between 20 to 100° C., preferably 25° C. Alternatively, treatment of compounds of formula II with, for example, 1-ethyl-3-(3-dimethylaminopropyl)carbodiimide EDC or dicyclohexyl carbodiimide DCC will generate an activated species IIa, wherein $X_{00}$ is $X_{01}$ or $X_{02}$ respectively, in an inert solvent, such as pyridine or tetrahydrofuran THF, optionally in the presence of a base, such as triethylamine, at temperatures between 25-180° C.; followed by ii) treatment of the activated species IIa with a compound of formula III (or a salt thereof), wherein $R_6$, $R_2$, $G_1$ and $G_2$ are as described under formula I above, optionally in the presence of a base, such as triethylamine or pyridine, in an inert solvents such as dichloromethane, tetrahydrofuran, dioxane or toluene, at temperatures between 0 and 80° C., to form the compounds of formula IV and/or IVa (or a mixture thereof).

Compounds of formula IV and/or IVa (or a mixture thereof) may further be converted into compounds of formula Ia, wherein Q is as defined above, and wherein $R_6$, $R_2$, $G_1$ and $G_2$ are as described under formula I above, by dehydration, e.g. by heating the compounds IV and/or IVa (or a mixture thereof) in the presence of an acid catalyst, such as for example methane sulfonic acid, or para-toluene sulfonic acid TsOH, in an inert solvent such as N-methyl pyrrolidine NMP or in pur acid such as actetic acid with or without solvent, at temperatures between 25-180° C., preferably 100-170° C., optionally under microwave conditions. Such processes have been described previously, for example, in WO 2010/125985.

Compounds of formula Ia, wherein Q is as defined above, and wherein Z is a leaving group, for example halogen, preferably fluorine or chlorine, and wherein $R_6$, $R_2$, $G_1$ and $G_2$ are as described under formula I above, can be reacted with compounds of formula V

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula Ib, wherein $R_1$ is as described under formula I above, and in which $R_6$, A, $R_2$, $L_1$, $L_2$, $L_3$, $L_4$, $G_1$ and $G_2$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Similar chemistry has been previously described, as for example in WO2013/018928. Examples of salts of the compound of formula V include compounds of the formula Va

wherein $R_1$ is as defined above and wherein M is, for example, sodium or potassium. This is illustrated for compounds of formula Ib in scheme 3:

Scheme 3

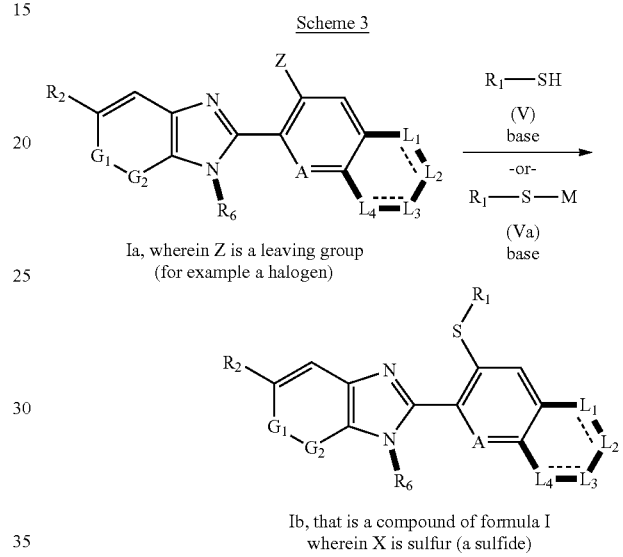

Ia, wherein Z is a leaving group
(for example a halogen)

Ib, that is a compound of formula I
wherein X is sulfur (a sulfide)

Alternatively, this reaction can be carried out in the presence of a palladium catalyst, such as tris(dibenzylideneacetone)dipalladium(0), in the presence of a phosphor ligand, such as xanthphos, in an inert solvent, for example, xylene at temperatures between 100-160° C., preferably 140° C., as described by Perrio et al. in Tetrahedron 2005, 61, 5253-5259.

The subgroup of compounds of formula I, wherein X is SO (sulfoxide) and/or $SO_2$ (sulfone), may be obtained by means of an oxidation reaction of the corresponding sulfide compounds of formula I, wherein X is S (i.e. a compound of formula Ib above), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds Ib to produce the sulfoxide compounds I (wherein X=SO), and preferably 2 to 2.2 moles of oxidant, relative to 1 mole of of the sulfide compounds Ib to produce the sulfone compounds I (wherein X=SC$_2$). Such oxidation reactions are disclosed, for example, in WO 2013/018928.

The sequence to prepare compounds of formula IIIa wherein R$_2$, R$_4$ and R$_6$ are as described under formula I above, from compounds of formula VIII, may involve i. alkylation of compound VIII with R$_6$—X$_{LG}$, wherein R$_6$ is as described under formula I above and wherein X$_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula VII, wherein R$_6$, R$_4$ and R$_2$ are as described under formula I above Alternatively, the alkylation could be realized via amino-reduction (see for example: Comprehensive Organic Transformations: A Guide to Functional Group Preparations. Edited by Richard C. Larock 1989 p 421, VCH publishers) or cooper coupling (e.g. Chan-Lam coupling: See for example: Org. Lett., Vol. 11, No. 8, 2009, 1677-1680); ii. a reaction of nitration of compound VII in classical conditions, for example, see for example, Advanced Organic Chemistry: Reactions, Mechanisms, and Structure, Fourth Edition by Jerry March, 1992 (Publisher Wiley New York, N.Y.) pages 523-525; and finally iii. a reaction of reduction of compound VI in classical conditions, for example, see for example, Advanced Organic Chemistry: Reactions, Mechanisms, and Structure, Fourth Edition by Jerry March, 1992 (Publisher Wiley New York, N.Y.) p 1216-1217. See scheme 4.

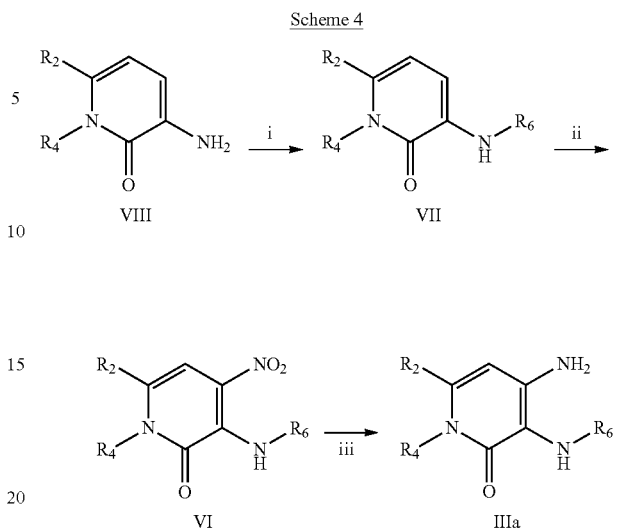

Scheme 4

Compounds of formula VIII may be made by methods known to a person skilled in the art, for example Synthesis 2005, No. 8, pp 1269-1278 and Synthesis 2011, No. 7, pp 1149-1156.

Compounds of formula I-2a, wherein Z is X—R$_1$ or a leaving group, for example halogen, and wherein X, R$_1$, R$_4$, R$_6$, A and R$_2$ are as described under formula I above, may be prepared by reaction between compounds of formula 11 respectively IIa, wherein Z is X—R$_1$ or a leaving group, for example halogen, and wherein X, R$_1$ and A are as described under formula I above, and in which X$_{00}$ is as described above, and compounds of formula IIIa, wherein R$_6$ and R$_2$ are as described under formula I above, under similar conditions as for the preparation of compounds of formula Ia from compounds of formula II/IIa and III described above (see scheme 1 and 2). This is illustrated for compounds of formula IIIa in scheme 5:

Scheme 5

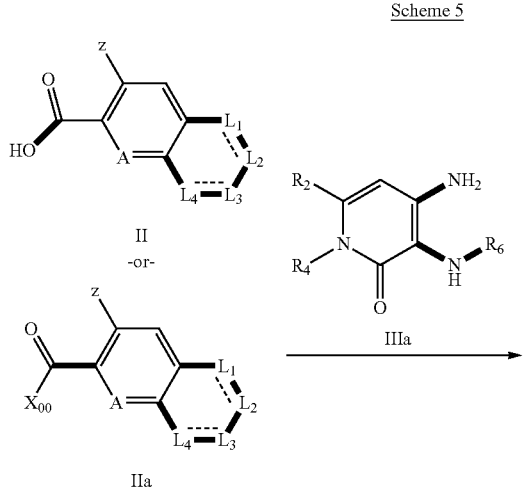

-continued

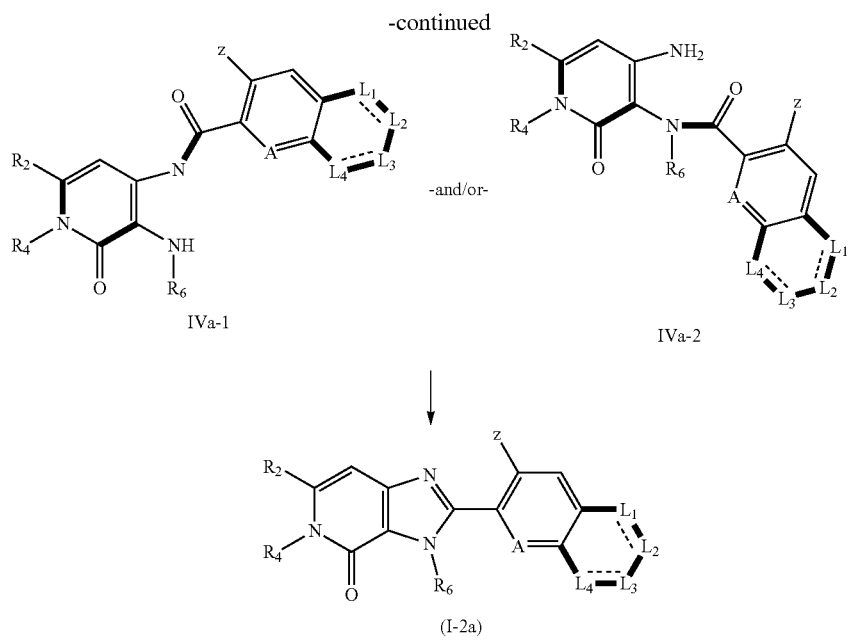

IVa-1

-and/or-

IVa-2

↓

(I-2a)

The sequence to prepare compounds of formula IIIb wherein $R_2$, $R_5$ and $R_6$ are as described under formula I above, from compounds of formula XII, may involve i. alkylation of compound XII with $R_5$—$X_{LG}$, wherein $R_5$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula XI, wherein $R_6$ and $R_5$ are as described under formula I above. Alternatively, the alkylation could be realized via amino-reduction (see for example: Comprehensive Organic Transformations: A Guide to Functional Group Preparations. Edited by Richard C. Larock 1989 p 421, VCH publishers) or cooper coupling (e.g. Chan-Lam coupling: See for example: Org. Lett., Vol. 11, No. 8, 2009, 1677-1680).; ii. a reaction of Vicarious nucleophilic substitution (VNS) reaction of compound XI in classical conditions, for example, J. Org. Chem., Vol. 61, No. 2, 1996 p 442; iii. alkylation of compound X with $R_6$-XLG, wherein $R_6$ is as described under formula I above and wherein XLG is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IX, wherein $R_6$, $R_5$ and $R_2$ are as described under formula I above and finally iv. a reaction of reduction of compound IX in classical conditions, for example, see for example, Advanced Organic Chemistry: Reactions, Mechanisms, and Structure, Fourth Edition by Jerry March, 1992 (Publisher Wiley New York, N. Y.) p 1216-1217. See scheme 6.

Scheme 6

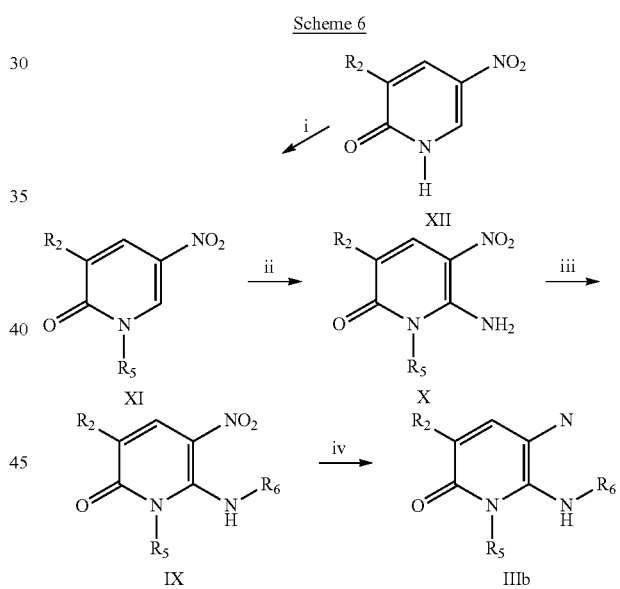

Compounds of formula XII are commercialy available or may be made by methods known to a person skilled in the art.

Compounds of formula I-1a, wherein Z is X—$R_1$ or a leaving group, for example halogen, and wherein X, $R_1$, $R_2$, $R_5$, $R_6$ and A are as described under formula I above, may be prepared by reaction between compounds of formula II respectively IIa, wherein Z is X—$R_1$ or a leaving group, for example halogen, and wherein X, $R_1$ and A are as described under formula I above, and in which $X_{00}$ is as described above, and compounds of formula IIIb, wherein $R_5$, $R_6$ and $R_2$ are as described under formula I above, under similar conditions as for the preparation of compounds of formula Ia from compounds of formula II/IIa and III described above (see scheme 1 and 2). This is illustrated in scheme 7:

Scheme 7

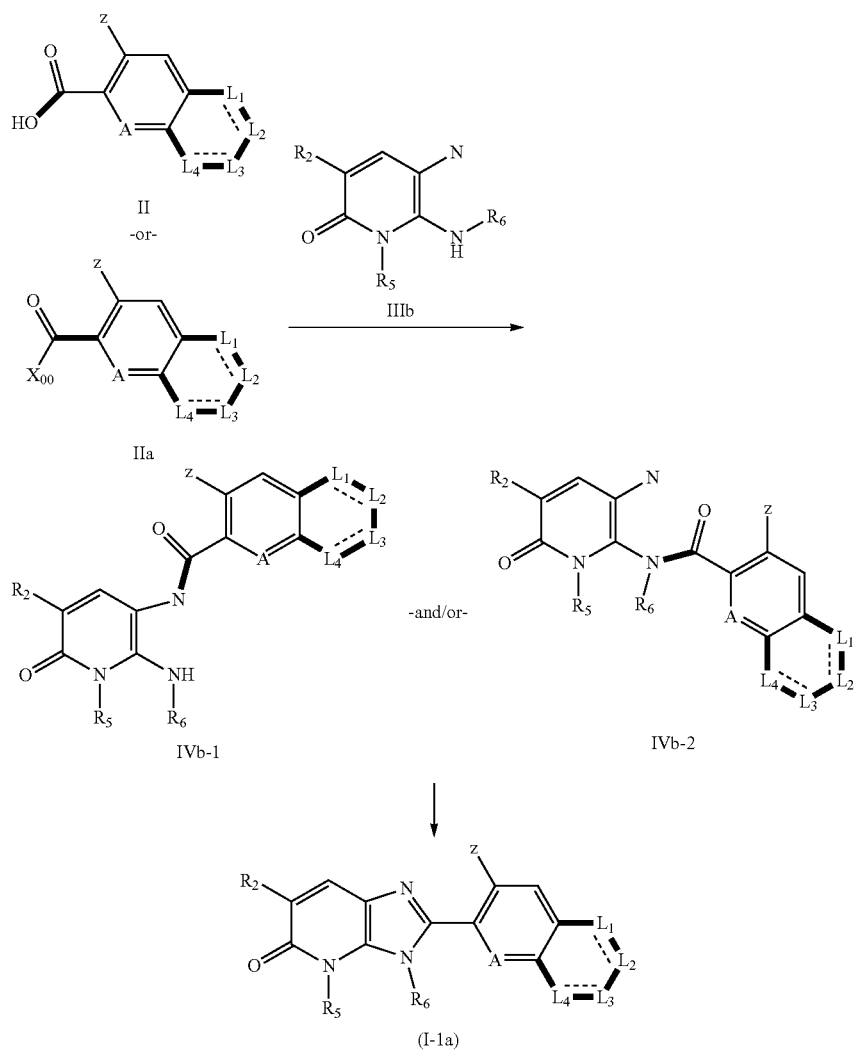

Compounds of formula II,

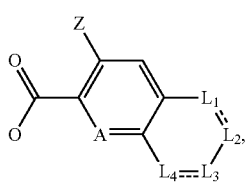

(II)

wherein Z is X—R$_1$ or a leaving group or a group that could be transformed in leaving group such as, for example amine or nitro, and wherein X, R$_1$, L$_1$, L$_2$, L$_3$, L$_4$ and A are as described under formula I above, may be either known, commercially available or may be made by methods known to a person skilled in the art.

Compounds of formula IIc, wherein Q is as defined above, and wherein Z is a leaving group, for example halogen, preferably fluorine or chlorine, and wherein A, L$_1$, L$_2$, L$_3$ and L$_4$ are as described under formula I above, and wherein R is alkyl or hydrogen can be reacted with compounds of formula V

or a salt thereof, wherein R$_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula IId, wherein R is alkyl or hydrogen, R$_1$ is as described under formula I above, and in which A, L$_1$, L$_2$, L$_3$ and L$_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $$R_1-S-M \quad \text{(Va)},$$

wherein $R_1$ is as defined above and wherein M is, for example, sodium or potassium. This is illustrated for compounds of formula IId in scheme 8:

Scheme 8

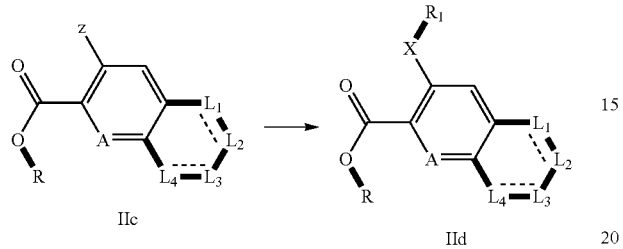

IIc → IId

Alternatively, compounds of formula IIc, wherein Z is a amine and wherein A, $L_1$, $L_2$, $L_3$ and $L_4$ are as described under formula I above, and wherein R is alkyl or hydrogen can be transformed to compounds of formula IId via diazotation and reaction with dialkyldisulfide. This transformation is well known and could be made by methods known to a person skilled in the art (see for example: Synthetic Communications, 31(12), 1857-1861; 2001 or Organic & Biomolecular Chemistry, 6(4), 745-761; 2008).

Compounds of formula IIc, wherein Z is a amine and wherein A, $L_1$, $L_2$, $L_3$ and $L_4$ are as described under formula I above, and wherein R is alkyl or hydrogen can be transformed to compounds of formula IIe via diazotation and reaction with sodium sulphide, followed by reduction. This transformation is well known and could be made by methods known to a person skilled in the art (see for example : US 20040116734 or Chemische Berichte, 120(7), 1151-73; 1987). Alkylation of compound IIe with $R_1$—$X_{LG}$, wherein $R_1$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula IId, wherein $R_1$ is as described under formula I above. See scheme 9.

Scheme 9

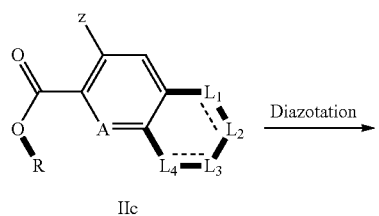

IIc

Diazotation →

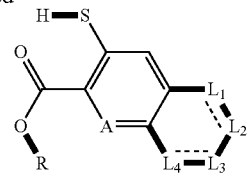

IIe

↓ $R_1$—$X_{LG}$

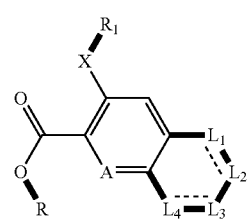

IId

Compound of formula (II) may be prepared by reaction of a compound of formula (IId), wherein R is alkyl via hydrolysis. For instance, in the case where R is methyl or ethyl, the hydrolysis can be done with water and a base, such as potassium hydroxide or lithium hydroxide, in the absence or in the presence of a solvent, such as, for instance, tetrahydrofuran or methanol. In the case where R is, for example, tert-butyl, the hydrolysis is done in the presence of acid, such as trifluoroacetic acid or hydrochloric acid. The reaction is carried out at a temperature of from −120° C. to +130° C., preferably from —100° C. to 100° C. See scheme 10.

Scheme 10

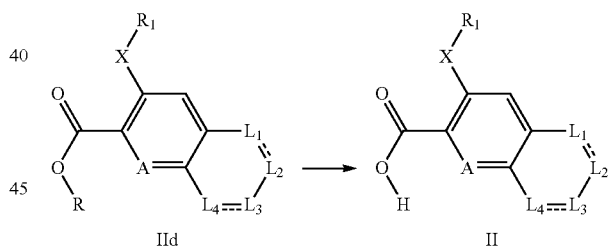

IId → II

Alternatively, compound of formula II may be prepared by reaction of a compound of formula (XIII) wherein Z is a leaving group as nitro or halogen such as fluorine and wherein A, $L_1$, $L_2$, $L_3$ and $L_4$ are as described under formula I above by reaction of a compound of formula V or Va $$R_1-SH \quad \text{(V)},$$

$$R_1-S-M \quad \text{(Va)},$$

to give compounds of formula XIIId or a salt thereof, wherein X and $R_1$ is as defined in formula I and in which A, $L_1$, $L_2$, $L_3$ and $L_4$ are as described under formula I above, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide.

Compounds of formula II may be prepared by hydrolysis of the cyano of compound of formula XIIId in acidic or basic conditions. This transformation is well known and could be made by methods known to a person skilled in the art (see for example: Comprehensive Organic Transformations: A Guide to Functional Group Preparations. Edited by Richard C. Larock 1989 p 993, VCH publishers).

This is illustrated for compounds of formula II in scheme 11.

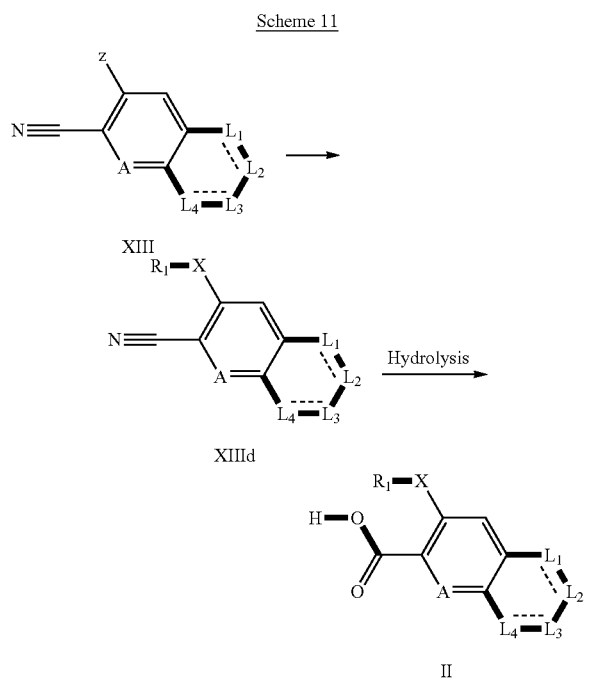

Compounds of formula XIII are either known, commercially available or may be made by methods known to a person skilled in the art.

Alternatively, compound of formula II may be prepared by reaction of a compound of formula (XIV) where in Z is a leaving group as nitro or halogen such as fluorine and wherein A, $L_1$, $L_2$, $L_3$ and $L_4$ are as described under formula I above by oxidation in presence of a oxidant such as oxygen, hydrogen peroxide or an metal oxide such as chromium trioxide with or without acid such as sulphuric acid with or without metal catalyst. This transformation is well known and could be made by methods known to a person skilled in the art (see for example: Comprehensive Organic Transformations: A Guide to Functional Group Preparations. Edited by Richard C. Larock 1989 p 823, VCH publishers). This is illustrated for compounds of formula II in scheme 12.

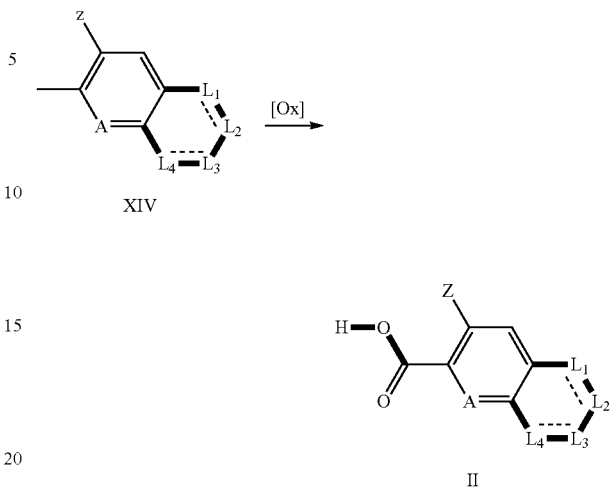

Compounds of formula XIV are either known, commercially available or may be made by methods known to a person skilled in the art.

Alternatively synthesis of compounds of formula I (benzimidazoles ($J_{19}$ and $J_{23}$) wherein: $L_1$=N or $NR_{10a}$, $L_2$=C—$R_{10b}$, $L_3$=N or N—$R_{10c}$, $L_4$=bond; benzothiadiazoles ($J_{20}$): $L_1$=N, $L_2$=S, $L_3$=N, $L_4$=bond; benzothiazoles ($J_{12}$): $L_1$=N, $L_2$=C—$R_{10b}$, $L_3$=S, $L_4$=bond; benzotriazoles ($J_{18}$, $J_{17}$ and $J_{24}$): $L_1$=N or N—$R_{10a}$, $L_2$=N or N—$R_{10b}$, $L_3$=N or N—$R_{10c}$, $L_4$=bond; benzoxazoles ($J_{25}$): $L_1$=N, $L_2$=C—$R_{10b}$, $L_3$=O, $L_4$=bond can be made via cyclisation of intermediates of formulae XVII or XVIII as depicted in scheme 13.

The synthesis of cyclic compounds as described in the scheme 13 is very well known and could be made by methods known to a person skilled in the art by analogy of what was described previously in literature. For example, for the synthesis of benzimidazoles starting from the intermediate type XVIII see Monatshefte fuer Chemie 2011, 142(1), 87-91; Organic Preparations and Procedures International 2013, 45(1), 57-65; Organic Preparations and Procedures International 2013, 45(2), 162-167; Tetrahedron Letters 2007 48(18), 3251-3254; or starting from the intermediate type XVII, see for example Journal of Organic Chemistry 2011, 76(23), 9577-9583 or Tetrahedron 2013, 69(6), 1717-1719. In general manner, see for review on the preparation of benzimidazoles: The Chemistry of Heterocyclic Compounds; Weissberger, A., Taylor, E. C., Eds.; Wiley-VCH: New York, NY, 1981; Vol. 40, pp 6-60.

For example, for the synthesis of benzothiadiazoles starting from the intermediate type XVIII see Tetrahedron 2005, 61(46), 10975-10982. See for a more general review on the preparation and properties of benzimidazoles: *Eur. J. Org. Chem.* 2013, 228-255.

For example, for the synthesis of benzotriazoles starting from the intermediate type XVIII see for example, Bioorganic & Medicinal Chemistry 2010, 18(24), 8457-8462, using cyclocondensation as described in scheme 13 (e.g. AcOH, NaNO$_2$). For a more general review on the preparation of benzotriazoles, see, for example, Journal Chem. Pharm. Res., 2011, 3(6) p 375-381.

For example, for the synthesis of benzothiazoles starting from the intermediate type XVII see for example, Journal of Combinatorial Chemistry 2009, 11(6), 1047-1049; Chemistry—A European Journal 2012, 18(16), 4840-4843, S4840/1-S4840/35; or WO13066729. In addition, synthesis of benzothiazoles are well known and could be made easily by methods known to a person skilled in the art via other type of intermediates see, for example, Journal of Current Pharmaceutical Research 2010; 3(1): 13-23.

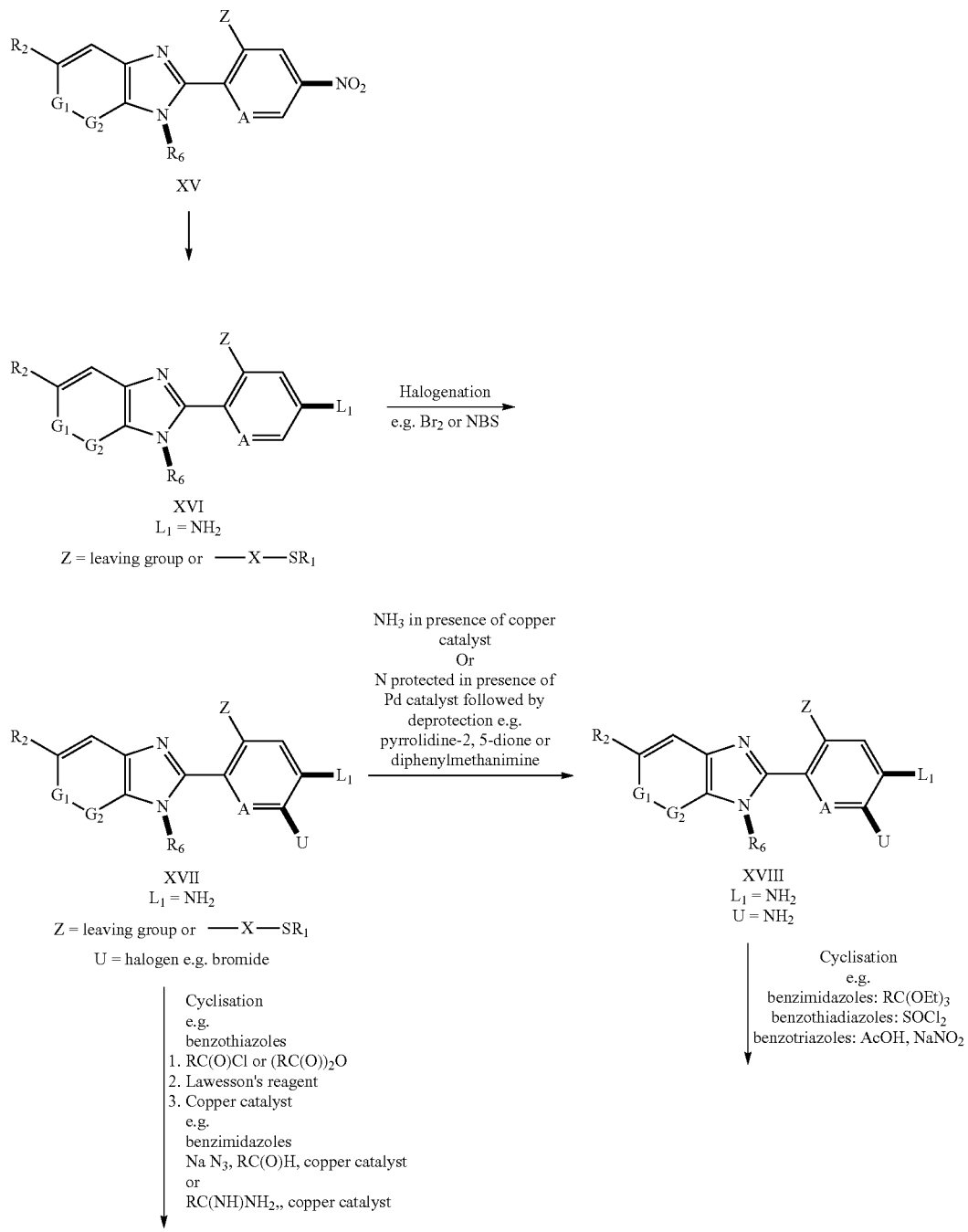

Scheme 13: Alternative preparation of compounds of formula I

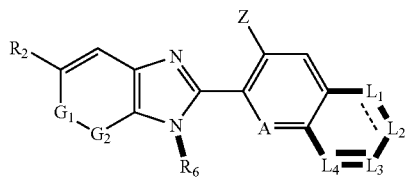

Ia or Ib
L₄ = Bond
Z = leaving group or —X—SR₁ if Z = leaving group see scheme 3

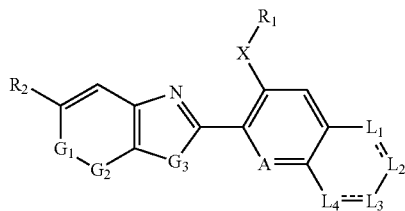

I
L₄ = Bond

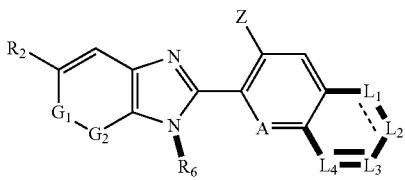

Ia or Ib
L₄ = Bond
Z = leaving group or —X—SR₁ if Z = leaving group see scheme 3

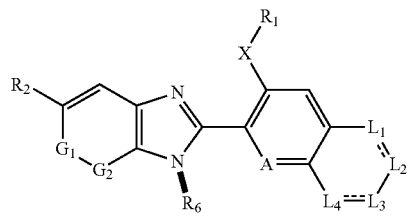

I
L₄ = Bond

Compounds of formula XV may be prepared by identical reaction described in scheme 1 to 6 wherein $L_1$ is $NO_2$ or compounds of formula XV may be prepared by identical reaction described in scheme 1 to 6 wherein $L_1$ is a protected nitrogen, for example $L_1$ could be pyrrolidine-2,5-dione followed by deprotection, for example with hydrazine.

Compounds of formula Ia, Ib, and I containing an N—H as $L_1$, $L_2$ or $L_3$ could react with a alkylation agent such as methyl iodide in presence of a base, such as potassium carbonate or sodium hydride, to give compounds of formula Ia, Ib, and I wherein $L_1$, $L_2$ or $L_3$ is, for example, an N—$CH_3$.

Compounds of formula I, wherein Y is S, can be prepared (scheme 14) by reacting compounds of formula I-1 or I-2, wherein Y is O with a reagent that could transfer a sulphur atom such as, for example, the Lawesson's reagent in a solvent such as, for example dimethylformamide or toluene, usually at temperature between 50 to 150° C. This type of transformation is known to a person skilled in the art and are, for example, described in Tetrahedron (2007), 63(48), 11862-11877 or US20120309796.

Alternatively, the O of the C(O) can be transformed on S on previews intermediate such as for example , compounds of formula XII or XI.

Preparation of Quinoxalines derivatives: The compound of formula Ia or Ib wherein $R_2$, $G_1$, $G_2$ and $G_3$ are as defined in formula I, L1 and L2 are nitrogen, $L_2$ and $L_3$ are, respectively C—$R_{10b}$ and C—$R_{10c}$, and Z is a leaving group or X—$R_1$, can be produced by reacting a compound of formula XVIII (for example, prepared as describe in scheme 15) with Glyoxal analogues (XIX) and transformed in compound of formula I (if Z is a leaving group) via the conditions described, for example in scheme 3. Such transformation is well known to those skilled in the art and have been described, for example in Journal of Heterocyclic Chemistry, 51(5), 1504-1508; 2014, Synthesis, 45(11), 1546-1552; 2013 and cited references.

scheme 14

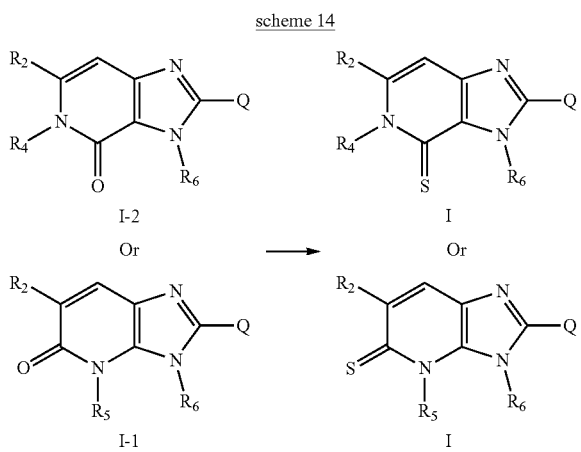

I-2

Or

I-1

Scheme 17

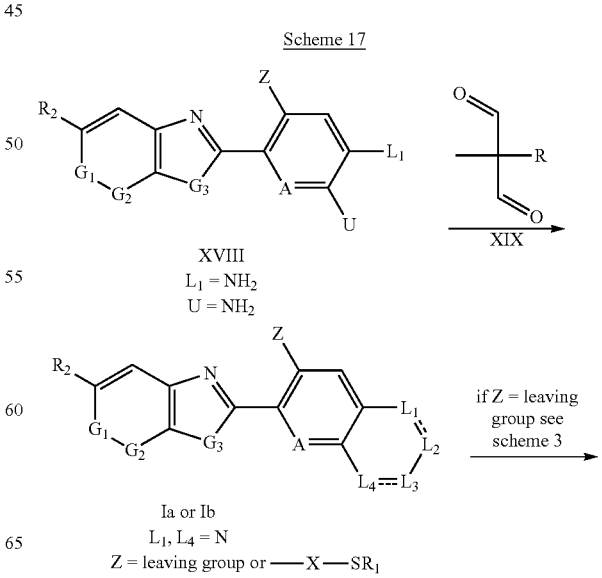

XVIII
$L_1$ = $NH_2$
U = $NH_2$

Ia or Ib
$L_1$, $L_4$ = N
Z = leaving group or —X—SR₁ if Z = leaving group see scheme 3

-continued

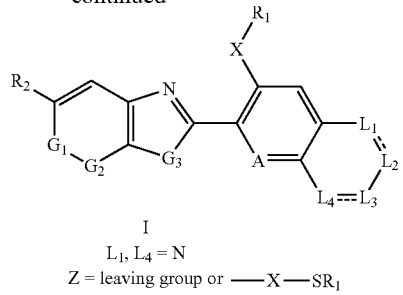

I
$L_1, L_4 = N$
Z = leaving group or —X—$SR_1$

For preparing all other compounds of the formula (I) functionalized according to the definitions of formula III and Q, there are a large number of suitable known standard methods, for example alkylation, halogenation, acylation, amidation, oximation, oxidation and reduction, the choice of the preparation methods which are suitable depending on the properties (reactivity) of the substituents in the intermediates.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties, can be obtained in free form or in the form of salts.

The compounds of formula I and, where appropriate, the tautomer's thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 4 below can be prepared according to the methods described above. The examples which follow are intended to illustrate the invention and show preferred compounds of formula I. "Ph" represents the phenyl group.

Table 1: This table discloses the 264 compounds of the formula I-1 a:

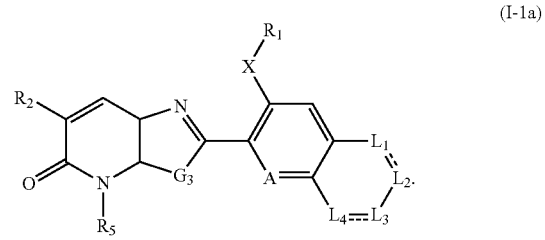

(I-1a)

TABLE 1

| Comp. No. | $G_3$ | X | $R_1$ | A | $R_2$ | $R_5$ | $L_1$ | $L_2$ | $L_3$ | $L_4$ |
|---|---|---|---|---|---|---|---|---|---|---|
| 1.001 | N—$CH_3$ | S | —$CH_2CH_3$ | C—H | $CF_3$ | $CH_3$ | CH | CH | CH | CH |
| 1.002 | N—$CH_3$ | $SO_2$ | —$CH_2CH_3$ | C—H | $CF_3$ | $CH_3$ | CH | CH | CH | CH |
| 1.003 | N—$CH_3$ | S | —$CH_2CH_3$ | C—H | $SCF_3$ | $CH_3$ | CH | CH | CH | CH |
| 1.004 | N—$CH_3$ | $SO_2$ | —$CH_2CH_3$ | C—H | $SCF_3$ | $CH_3$ | CH | CH | CH | CH |
| 1.005 | N—$CH_3$ | S | —$CH_2CH_3$ | C—H | $CF_2CF_3$ | $CH_3$ | CH | CH | CH | CH |
| 1.006 | N—$CH_3$ | $SO_2$ | —$CH_2CH_3$ | C—H | $CF_2CF_3$ | $CH_3$ | CH | CH | CH | CH |
| 1.007 | N—$CH_3$ | S | —$CH_2CH_3$ | N | $CF_3$ | $CH_3$ | CH | CH | CH | CH |
| 1.008 | N—$CH_3$ | $SO_2$ | —$CH_2CH_3$ | N | $CF_3$ | $CH_3$ | CH | CH | CH | CH |
| 1.009 | N—$CH_3$ | S | —$CH_2CH_3$ | N | $SCF_3$ | $CH_3$ | CH | CH | CH | CH |
| 1.010 | N—$CH_3$ | $SO_2$ | —$CH_2CH_3$ | N | $SCF_3$ | $CH_3$ | CH | CH | CH | CH |
| 1.011 | N—$CH_3$ | S | —$CH_2CH_3$ | N | $CF_2CF_3$ | $CH_3$ | CH | CH | CH | CH |
| 1.012 | N—$CH_3$ | $SO_2$ | —$CH_2CH_3$ | N | $CF_2CF_3$ | $CH_3$ | CH | CH | CH | CH |
| 1.013 | N—$CH_3$ | S | —$CH_2CH_3$ | C—H | $CF_3$ | $CH_3$ | CH | N | N—$CH_3$ | bond |
| 1.014 | N—$CH_3$ | $SO_2$ | —$CH_2CH_3$ | C—H | $CF_3$ | $CH_3$ | CH | N | N—$CH_3$ | bond |
| 1.015 | N—$CH_3$ | S | —$CH_2CH_3$ | C—H | $CF_3$ | $CH_3$ | CH | N—$CH_3$ | N | bond |
| 1.016 | N—$CH_3$ | $SO_2$ | —$CH_2CH_3$ | C—H | $CF_3$ | $CH_3$ | CH | N—$CH_3$ | N | bond |
| 1.017 | N—$CH_3$ | S | —$CH_2CH_3$ | N | $CF_3$ | $CH_3$ | CH | N | N—$CH_3$ | bond |
| 1.018 | N—$CH_3$ | $SO_2$ | —$CH_2CH_3$ | N | $CF_3$ | $CH_3$ | CH | N | N—$CH_3$ | bond |
| 1.019 | N—$CH_3$ | S | —$CH_2CH_3$ | N | $CF_3$ | $CH_3$ | CH | N—$CH_3$ | N | bond |
| 1.020 | N—$CH_3$ | $SO_2$ | —$CH_2CH_3$ | N | $CF_3$ | $CH_3$ | CH | N—$CH_3$ | N | bond |
| 1.021 | N—$CH_3$ | S | —$CH_2CH_3$ | C—H | $CF_3$ | $CH_3$ | N | CH | CH | CH |
| 1.022 | N—$CH_3$ | $SO_2$ | —$CH_2CH_3$ | C—H | $CF_3$ | $CH_3$ | N | CH | CH | CH |
| 1.023 | N—$CH_3$ | S | —$CH_2CH_3$ | N | $CF_3$ | $CH_3$ | N | CH | CH | CH |
| 1.024 | N—$CH_3$ | $SO_2$ | —$CH_2CH_3$ | N | $CF_3$ | $CH_3$ | N | CH | CH | CH |
| 1.025 | N—$CH_3$ | S | —$CH_2CH_3$ | C—H | $CF_3$ | $CH_3$ | CH | N | CH | CH |
| 1.026 | N—$CH_3$ | $SO_2$ | —$CH_2CH_3$ | C—H | $CF_3$ | $CH_3$ | CH | N | CH | CH |
| 1.027 | N—$CH_3$ | S | —$CH_2CH_3$ | N | $CF_3$ | $CH_3$ | CH | N | CH | CH |
| 1.028 | N—$CH_3$ | $SO_2$ | —$CH_2CH_3$ | N | $CF_3$ | $CH_3$ | CH | N | CH | CH |
| 1.029 | N—$CH_3$ | S | —$CH_2CH_3$ | C—H | $CF_3$ | $CH_3$ | N—$CH_3$ | N | CH | Bond |
| 1.030 | N—$CH_3$ | $SO_2$ | —$CH_2CH_3$ | C—H | $CF_3$ | $CH_3$ | N—$CH_3$ | N | CH | Bond |
| 1.031 | N—$CH_3$ | S | —$CH_2CH_3$ | N | $CF_3$ | $CH_3$ | N—$CH_3$ | N | CH | Bond |
| 1.032 | N—$CH_3$ | $SO_2$ | —$CH_2CH_3$ | N | $CF_3$ | $CH_3$ | N—$CH_3$ | N | CH | Bond |
| 1.033 | N—$CH_3$ | S | —$CH_2CH_3$ | C—H | $CF_3$ | $CH_3$ | N | N—$CH_3$ | CH | Bond |
| 1.034 | N—$CH_3$ | $SO_2$ | —$CH_2CH_3$ | C—H | $CF_3$ | $CH_3$ | N | N—$CH_3$ | CH | Bond |
| 1.035 | N—$CH_3$ | S | —$CH_2CH_3$ | N | $CF_3$ | $CH_3$ | N | N—$CH_3$ | CH | Bond |
| 1.036 | N—$CH_3$ | $SO_2$ | —$CH_2CH_3$ | N | $CF_3$ | $CH_3$ | N | N—$CH_3$ | CH | Bond |
| 1.037 | N—$CH_3$ | S | —$CH_2CH_3$ | C—H | $CF_3$ | $CH_3$ | N | N—H | CH | Bond |
| 1.038 | N—$CH_3$ | $SO_2$ | —$CH_2CH_3$ | C—H | $CF_3$ | $CH_3$ | N | N—H | CH | Bond |
| 1.039 | N—$CH_3$ | S | —$CH_2CH_3$ | N | $CF_3$ | $CH_3$ | N | N—H | CH | Bond |
| 1.040 | N—$CH_3$ | $SO_2$ | —$CH_2CH_3$ | N | $CF_3$ | $CH_3$ | N | N—H | CH | Bond |
| 1.041 | N—$CH_3$ | S | —$CH_2CH_3$ | C—H | $CF_3$ | $CH_3$ | CH | N | N—H | bond |
| 1.042 | N—$CH_3$ | $SO_2$ | —$CH_2CH_3$ | C—H | $CF_3$ | $CH_3$ | CH | N | N—H | bond |
| 1.043 | N—$CH_3$ | S | —$CH_2CH_3$ | N | $CF_3$ | $CH_3$ | CH | N | N—H | bond |
| 1.044 | N—$CH_3$ | $SO_2$ | —$CH_2CH_3$ | N | $CF_3$ | $CH_3$ | CH | N | N—H | bond |
| 1.045 | N—$CH_3$ | S | —$CH_2CH_3$ | C—H | $CF_3$ | $CH_3$ | N | S | N | bond |
| 1.046 | N—$CH_3$ | $SO_2$ | —$CH_2CH_3$ | C—H | $CF_3$ | $CH_3$ | N | S | N | bond |
| 1.047 | N—$CH_3$ | S | —$CH_2CH_3$ | N | $CF_3$ | $CH_3$ | N | S | N | bond |
| 1.048 | N—$CH_3$ | $SO_2$ | —$CH_2CH_3$ | N | $CF_3$ | $CH_3$ | N | S | N | bond |
| 1.049 | N—$CH_3$ | S | —$CH_2CH_3$ | C—H | $CF_3$ | $CH_3$ | N | NH | N | bond |

TABLE 1-continued

| Comp. No. | G$_3$ | X | R$_1$ | A | R$_2$ | R$_5$ | L$_1$ | L$_2$ | L$_3$ | L$_4$ |
|---|---|---|---|---|---|---|---|---|---|---|
| 1.050 | N—CH$_3$ | SO$_2$ | —CH$_2$CH$_3$ | C—H | CF$_3$ | CH$_3$ | N | NH | N | bond |
| 1.051 | N—CH$_3$ | S | —CH$_2$CH$_3$ | N | CF$_3$ | CH$_3$ | N | NH | N | bond |
| 1.052 | N—CH$_3$ | SO$_2$ | —CH$_2$CH$_3$ | N | CF$_3$ | CH$_3$ | N | NH | N | bond |
| 1.053 | N—CH$_3$ | S | —CH$_2$CH$_3$ | C—H | CF$_3$ | CH$_3$ | N | N—CH$_3$ | N | bond |
| 1.054 | N—CH$_3$ | SO$_2$ | —CH$_2$CH$_3$ | C—H | CF$_3$ | CH$_3$ | N | N—CH$_3$ | N | bond |
| 1.055 | N—CH$_3$ | S | —CH$_2$CH$_3$ | N | CF$_3$ | CH$_3$ | N | N—CH$_3$ | N | bond |
| 1.056 | N—CH$_3$ | SO$_2$ | —CH$_2$CH$_3$ | N | CF$_3$ | CH$_3$ | N | N—CH$_3$ | N | bond |
| 1.057 | N—CH$_3$ | S | —CH$_2$CH$_3$ | C—H | CF$_3$ | CH$_3$ | N | N | N—CH$_3$ | bond |
| 1.058 | N—CH$_3$ | SO$_2$ | —CH$_2$CH$_3$ | C—H | CF$_3$ | CH$_3$ | N | N | N—CH$_3$ | bond |
| 1.059 | N—CH$_3$ | S | —CH$_2$CH$_3$ | N | CF$_3$ | CH$_3$ | N | N | N—CH$_3$ | bond |
| 1.060 | N—CH$_3$ | SO$_2$ | —CH$_2$CH$_3$ | N | CF$_3$ | CH$_3$ | N | N | N—CH$_3$ | bond |
| 1.061 | N—CH$_3$ | S | —CH$_2$CH$_3$ | C—H | CF$_3$ | CH$_3$ | N—CH$_3$ | N | N | bond |
| 1.062 | N—CH$_3$ | SO$_2$ | —CH$_2$CH$_3$ | C—H | CF$_3$ | CH$_3$ | N—CH$_3$ | N | N | bond |
| 1.063 | N—CH$_3$ | S | —CH$_2$CH$_3$ | N | CF$_3$ | CH$_3$ | N—CH$_3$ | N | N | bond |
| 1.064 | N—CH$_3$ | SO$_2$ | —CH$_2$CH$_3$ | N | CF$_3$ | CH$_3$ | N—CH$_3$ | N | N | bond |
| 1.065 | N—CH$_3$ | S | —CH$_2$CH$_3$ | C—H | CF$_3$ | CH$_3$ | CH | C—CF3 | CH | CH |
| 1.066 | N—CH$_3$ | SO$_2$ | —CH$_2$CH$_3$ | C—H | CF$_3$ | CH$_3$ | CH | C—CF$_3$ | CH | CH |
| 1.067 | N—CH$_3$ | S | —CH$_2$CH$_3$ | N | CF$_3$ | CH$_3$ | CH | C—CF$_3$ | CH | CH |
| 1.068 | N—CH$_3$ | SO$_2$ | —CH$_2$CH$_3$ | N | CF$_3$ | CH$_3$ | CH | C—CF$_3$ | CH | CH |
| 1.069 | N—CH$_3$ | S | —CH$_2$CH$_3$ | C—H | CF$_3$ | CH$_3$ | CH | C—F | CH | CH |
| 1.070 | N—CH$_3$ | SO$_2$ | —CH$_2$CH$_3$ | C—H | CF$_3$ | CH$_3$ | CH | C—F | CH | CH |
| 1.071 | N—CH$_3$ | S | —CH$_2$CH$_3$ | N | CF$_3$ | CH$_3$ | CH | C—F | CH | CH |
| 1.072 | N—CH$_3$ | SO$_2$ | —CH$_2$CH$_3$ | N | CF$_3$ | CH$_3$ | CH | C—F | CH | CH |
| 1.073 | N—CH$_3$ | S | —CH$_2$CH$_3$ | C—H | CF$_3$ | CH$_3$ | N | C—H | S | bond |
| 1.074 | N—CH$_3$ | SO$_2$ | —CH$_2$CH$_3$ | C—H | CF$_3$ | CH$_3$ | N | C—H | S | bond |
| 1.075 | N—CH$_3$ | S | —CH$_2$CH$_3$ | N | CF$_3$ | CH$_3$ | N | C—H | S | bond |
| 1.076 | N—CH$_3$ | SO$_2$ | —CH$_2$CH$_3$ | N | CF$_3$ | CH$_3$ | N | C—H | S | bond |
| 1.077 | N—CH$_3$ | S | —CH$_2$CH$_3$ | C—H | CF$_3$ | CH$_3$ | N | C—CH$_3$ | S | bond |
| 1.078 | N—CH$_3$ | SO$_2$ | —CH$_2$CH$_3$ | C—H | CF$_3$ | CH$_3$ | N | C—CH$_3$ | S | bond |
| 1.079 | N—CH$_3$ | S | —CH$_2$CH$_3$ | N | CF$_3$ | CH$_3$ | N | C—CH$_3$ | S | bond |
| 1.080 | N—CH$_3$ | SO$_2$ | —CH$_2$CH$_3$ | N | CF$_3$ | CH$_3$ | N | C—CH$_3$ | S | bond |
| 1.081 | N—CH$_3$ | S | —CH$_2$CH$_3$ | C—H | CF$_3$ | CH$_3$ | N | C—CF$_3$ | S | bond |
| 1.082 | N—CH$_3$ | SO$_2$ | —CH$_2$CH$_3$ | C—H | CF$_3$ | CH$_3$ | N | C—CF$_3$ | S | bond |
| 1.083 | N—CH$_3$ | S | —CH$_2$CH$_3$ | N | CF$_3$ | CH$_3$ | N | C—CF$_3$ | S | bond |
| 1.084 | N—CH$_3$ | SO$_2$ | —CH$_2$CH$_3$ | N | CF$_3$ | CH$_3$ | N | C—CF$_3$ | S | bond |
| 1.085 | N—CH$_3$ | S | —CH$_2$CH$_3$ | C—H | CF$_3$ | CH$_3$ | S | C—H | N | bond |
| 1.086 | N—CH$_3$ | SO$_2$ | —CH$_2$CH$_3$ | C—H | CF$_3$ | CH$_3$ | S | C—H | N | bond |
| 1.087 | N—CH$_3$ | S | —CH$_2$CH$_3$ | N | CF$_3$ | CH$_3$ | S | C—H | N | bond |
| 1.088 | N—CH$_3$ | SO$_2$ | —CH$_2$CH$_3$ | N | CF$_3$ | CH$_3$ | S | C—H | N | bond |
| 1.089 | N—CH$_3$ | S | —CH$_2$CH$_3$ | C—H | CF$_3$ | CH$_3$ | S | C—CH$_3$ | N | bond |
| 1.090 | N—CH$_3$ | SO$_2$ | —CH$_2$CH$_3$ | C—H | CF$_3$ | CH$_3$ | S | C—CH$_3$ | N | bond |
| 1.091 | N—CH$_3$ | S | —CH$_2$CH$_3$ | N | CF$_3$ | CH$_3$ | S | C—CH$_3$ | N | bond |
| 1.092 | N—CH$_3$ | SO$_2$ | —CH$_2$CH$_3$ | N | CF$_3$ | CH$_3$ | S | C—CH$_3$ | N | bond |
| 1.093 | N—CH$_3$ | S | —CH$_2$CH$_3$ | C—H | CF$_3$ | CH$_3$ | S | C—CF$_3$ | N | bond |
| 1.094 | N—CH$_3$ | SO$_2$ | —CH$_2$CH$_3$ | C—H | CF$_3$ | CH$_3$ | S | C—CF$_3$ | N | bond |
| 1.095 | N—CH$_3$ | S | —CH$_2$CH$_3$ | N | CF$_3$ | CH$_3$ | S | C—CF$_3$ | N | bond |
| 1.096 | N—CH$_3$ | SO$_2$ | —CH$_2$CH$_3$ | N | CF$_3$ | CH$_3$ | S | C—CF$_3$ | N | bond |
| 1.097 | N—CH$_3$ | S | —CH$_2$CH$_3$ | C—H | CF$_3$ | CH$_3$ | N—H | C—CF$_3$ | N | bond |
| 1.098 | N—CH$_3$ | SO$_2$ | —CH$_2$CH$_3$ | C—H | CF$_3$ | CH$_3$ | N—H | C—CF$_3$ | N | bond |
| 1.099 | N—CH$_3$ | S | —CH$_2$CH$_3$ | N | CF$_3$ | CH$_3$ | N—H | C—CF$_3$ | N | bond |
| 1.100 | N—CH$_3$ | SO$_2$ | —CH$_2$CH$_3$ | N | CF$_3$ | CH$_3$ | N—H | C—CF$_3$ | N | bond |
| 1.101 | N—CH$_3$ | S | —CH$_2$CH$_3$ | C—H | CF$_3$ | CH$_3$ | N—H | C—CH$_3$ | N | bond |
| 1.102 | N—CH$_3$ | SO$_2$ | —CH$_2$CH$_3$ | C—H | CF$_3$ | CH$_3$ | N—H | C—CH$_3$ | N | bond |
| 1.103 | N—CH$_3$ | S | —CH$_2$CH$_3$ | N | CF$_3$ | CH$_3$ | N—H | C—CH$_3$ | N | bond |
| 1.104 | N—CH$_3$ | SO$_2$ | —CH$_2$CH$_3$ | N | CF$_3$ | CH$_3$ | N—H | C—CH$_3$ | N | bond |
| 1.105 | N—CH$_3$ | S | —CH$_2$CH$_3$ | C—H | CF$_3$ | CH$_3$ | N—H | CH | N | bond |
| 1.106 | N—CH$_3$ | SO$_2$ | —CH$_2$CH$_3$ | C—H | CF$_3$ | CH$_3$ | N—H | CH | N | bond |
| 1.107 | N—CH$_3$ | S | —CH$_2$CH$_3$ | N | CF$_3$ | CH$_3$ | N—H | CH | N | bond |
| 1.108 | N—CH$_3$ | SO$_2$ | —CH$_2$CH$_3$ | N | CF$_3$ | CH$_3$ | N—H | CH | N | bond |
| 1.109 | N—CH$_3$ | S | —CH$_2$CH$_3$ | C—H | CF$_3$ | CH$_3$ | N—CH$_3$ | CH | N | bond |
| 1.110 | N—CH$_3$ | SO$_2$ | —CH$_2$CH$_3$ | C—H | CF$_3$ | CH$_3$ | N—CH$_3$ | CH | N | bond |
| 1.111 | N—CH$_3$ | S | —CH$_2$CH$_3$ | N | CF$_3$ | CH$_3$ | N—CH$_3$ | CH | N | bond |
| 1.112 | N—CH$_3$ | SO$_2$ | —CH$_2$CH$_3$ | N | CF$_3$ | CH$_3$ | N—CH$_3$ | CH | N | bond |
| 1.113 | N—CH$_3$ | S | —CH$_2$CH$_3$ | C—H | CF$_3$ | CH$_3$ | N—CH$_3$ | C—CH$_3$ | N | bond |
| 1.114 | N—CH$_3$ | SO$_2$ | —CH$_2$CH$_3$ | C—H | CF$_3$ | CH$_3$ | N—CH$_3$ | C—CH$_3$ | N | bond |
| 1.115 | N—CH$_3$ | S | —CH$_2$CH$_3$ | N | CF$_3$ | CH$_3$ | N—CH$_3$ | C—CH$_3$ | N | bond |
| 1.116 | N—CH$_3$ | SO$_2$ | —CH$_2$CH$_3$ | N | CF$_3$ | CH$_3$ | N—CH$_3$ | C—CH$_3$ | N | bond |
| 1.117 | N—CH$_3$ | S | —CH$_2$CH$_3$ | C—H | CF$_3$ | CH$_3$ | N—CH$_3$ | C—CF$_3$ | N | bond |
| 1.118 | N—CH$_3$ | SO$_2$ | —CH$_2$CH$_3$ | C—H | CF$_3$ | CH$_3$ | N—CH$_3$ | C—CF$_3$ | N | bond |
| 1.119 | N—CH$_3$ | S | —CH$_2$CH$_3$ | N | CF$_3$ | CH$_3$ | N—CH$_3$ | C—CF$_3$ | N | bond |
| 1.120 | N—CH$_3$ | SO$_2$ | —CH$_2$CH$_3$ | N | CF$_3$ | CH$_3$ | N—CH$_3$ | C—CF$_3$ | N | bond |
| 1.121 | N—CH$_3$ | S | —CH$_2$CH$_3$ | C—H | CF$_3$ | CH$_3$ | N | CH | N—CH$_3$ | bond |
| 1.122 | N—CH$_3$ | SO$_2$ | —CH$_2$CH$_3$ | C—H | CF$_3$ | CH$_3$ | N | CH | N—CH$_3$ | bond |
| 1.123 | N—CH$_3$ | S | —CH$_2$CH$_3$ | N | CF$_3$ | CH$_3$ | N | CH | N—CH$_3$ | bond |
| 1.124 | N—CH$_3$ | SO$_2$ | —CH$_2$CH$_3$ | N | CF$_3$ | CH$_3$ | N | CH | N—CH$_3$ | bond |
| 1.125 | N—CH$_3$ | S | —CH$_2$CH$_3$ | C—H | CF$_3$ | CH$_3$ | N | C—CH$_3$ | N—CH$_3$ | bond |
| 1.126 | N—CH$_3$ | SO$_2$ | —CH$_2$CH$_3$ | C—H | CF$_3$ | CH$_3$ | N | C—CH$_3$ | N—CH$_3$ | bond |
| 1.127 | N—CH$_3$ | S | —CH$_2$CH$_3$ | N | CF$_3$ | CH$_3$ | N | C—CH$_3$ | N—CH$_3$ | bond |

TABLE 1-continued

| Comp. No. | G₃ | X | R₁ | A | R₂ | R₅ | L₁ | L₂ | L₃ | L₄ |
|---|---|---|---|---|---|---|---|---|---|---|
| 1.128 | N—CH₃ | SO₂ | —CH₂CH₃ | N | CF₃ | CH₃ | N | C—CH₃ | N—CH₃ | bond |
| 1.129 | N—CH₃ | S | —CH₂CH₃ | C—H | CF₃ | CH₃ | N | C—CF₃ | N—CH₃ | bond |
| 1.130 | N—CH₃ | SO₂ | —CH₂CH₃ | C—H | CF₃ | CH₃ | N | C—CF₃ | N—CH₃ | bond |
| 1.131 | N—CH₃ | S | —CH₂CH₃ | N | CF₃ | CH₃ | N | C—CF₃ | N—CH₃ | bond |
| 1.132 | N—CH₃ | SO₂ | —CH₂CH₃ | N | CF₃ | CH₃ | N | C—CF₃ | N—CH₃ | Bond |
| 1.133 | N—CH₂CH₃ | S | —CH₂CH₃ | C—H | CF₃ | CH₃ | CH | CH | CH | CH |
| 1.134 | N—CH₂CH₃ | SO₂ | —CH₂CH₃ | C—H | CF₃ | CH₃ | CH | CH | CH | CH |
| 1.135 | N—CH₂CH₃ | S | —CH₂CH₃ | C—H | SCF₃ | CH₃ | CH | CH | CH | CH |
| 1.136 | N—CH₂CH₃ | SO₂ | —CH₂CH₃ | C—H | SCF₃ | CH₃ | CH | CH | CH | CH |
| 1.137 | N—CH₂CH₃ | S | —CH₂CH₃ | C—H | CF₂CF₃ | CH₃ | CH | CH | CH | CH |
| 1.138 | N—CH₂CH₃ | SO₂ | —CH₂CH₃ | C—H | CF₂CF₃ | CH₃ | CH | CH | CH | CH |
| 1.139 | N—CH₂CH₃ | S | —CH₂CH₃ | N | CF₃ | CH₃ | CH | CH | CH | CH |
| 1.140 | N—CH₂CH₃ | SO₂ | —CH₂CH₃ | N | CF₃ | CH₃ | CH | CH | CH | CH |
| 1.141 | N—CH₂CH₃ | S | —CH₂CH₃ | N | SCF₃ | CH₃ | CH | CH | CH | CH |
| 1.142 | N—CH₂CH₃ | SO₂ | —CH₂CH₃ | N | SCF₃ | CH₃ | CH | CH | CH | CH |
| 1.143 | N—CH₂CH₃ | S | —CH₂CH₃ | N | CF₂CF₃ | CH₃ | CH | CH | CH | CH |
| 1.144 | N—CH₂CH₃ | SO₂ | —CH₂CH₃ | N | CF₂CF₃ | CH₃ | CH | CH | CH | CH |
| 1.145 | N—CH₂CH₃ | S | —CH₂CH₃ | C—H | CF₃ | CH₃ | CH | N | N—CH₃ | bond |
| 1.146 | N—CH₂CH₃ | SO₂ | —CH₂CH₃ | C—H | CF₃ | CH₃ | CH | N | N—CH₃ | bond |
| 1.147 | N—CH₂CH₃ | S | —CH₂CH₃ | C—H | CF₃ | CH₃ | CH | N—CH₃ | N | bond |
| 1.148 | N—CH₂CH₃ | SO₂ | —CH₂CH₃ | C—H | CF₃ | CH₃ | CH | N—CH₃ | N | bond |
| 1.149 | N—CH₂CH₃ | S | —CH₂CH₃ | N | CF₃ | CH₃ | CH | N | N—CH₃ | bond |
| 1.15 | N—CH₂CH₃ | SO₂ | —CH₂CH₃ | N | CF₃ | CH₃ | CH | N | N—CH₃ | bond |
| 1.151 | N—CH₂CH₃ | S | —CH₂CH₃ | N | CF₃ | CH₃ | CH | N—CH₃ | N | bond |
| 1.152 | N—CH₂CH₃ | SO₂ | —CH₂CH₃ | N | CF₃ | CH₃ | CH | N—CH₃ | N | bond |
| 1.153 | N—CH₂CH₃ | S | —CH₂CH₃ | C—H | CF₃ | CH₃ | N | CH | CH | CH |
| 1.154 | N—CH₂CH₃ | SO₂ | —CH₂CH₃ | C—H | CF₃ | CH₃ | N | CH | CH | CH |
| 1.155 | N—CH₂CH₃ | S | —CH₂CH₃ | N | CF₃ | CH₃ | N | CH | CH | CH |
| 1.156 | N—CH₂CH₃ | SO₂ | —CH₂CH₃ | N | CF₃ | CH₃ | N | CH | CH | CH |
| 1.157 | N—CH₂CH₃ | S | —CH₂CH₃ | C—H | CF₃ | CH₃ | CH | N | CH | CH |
| 1.158 | N—CH₂CH₃ | SO₂ | —CH₂CH₃ | C—H | CF₃ | CH₃ | CH | N | CH | CH |
| 1.159 | N—CH₂CH₃ | S | —CH₂CH₃ | N | CF₃ | CH₃ | CH | N | CH | CH |
| 1.160 | N—CH₂CH₃ | SO₂ | —CH₂CH₃ | N | CF₃ | CH₃ | CH | N | CH | CH |
| 1.161 | N—CH₂CH₃ | S | —CH₂CH₃ | C—H | CF₃ | CH₃ | N—CH₃ | N | CH | Bond |
| 1.162 | N—CH₂CH₃ | SO₂ | —CH₂CH₃ | C—H | CF₃ | CH₃ | N—CH₃ | N | CH | Bond |
| 1.163 | N—CH₂CH₃ | S | —CH₂CH₃ | N | CF₃ | CH₃ | N—CH₃ | N | CH | Bond |
| 1.164 | N—CH₂CH₃ | SO₂ | —CH₂CH₃ | N | CF₃ | CH₃ | N—CH₃ | N | CH | Bond |
| 1.165 | N—CH₂CH₃ | S | —CH₂CH₃ | C—H | CF₃ | CH₃ | N | N—CH₃ | CH | Bond |
| 1.166 | N—CH₂CH₃ | SO₂ | —CH₂CH₃ | C—H | CF₃ | CH₃ | N | N—CH₃ | CH | Bond |
| 1.167 | N—CH₂CH₃ | S | —CH₂CH₃ | N | CF₃ | CH₃ | N | N—CH₃ | CH | Bond |
| 1.168 | N—CH₂CH₃ | SO₂ | —CH₂CH₃ | N | CF₃ | CH₃ | N | N—CH₃ | CH | Bond |
| 1.169 | N—CH₂CH₃ | S | —CH₂CH₃ | C—H | CF₃ | CH₃ | N | N—H | CH | Bond |
| 1.170 | N—CH₂CH₃ | SO₂ | —CH₂CH₃ | C—H | CF₃ | CH₃ | N | N—H | CH | Bond |
| 1.171 | N—CH₂CH₃ | S | —CH₂CH₃ | N | CF₃ | CH₃ | N | N—H | CH | Bond |
| 1.172 | N—CH₂CH₃ | SO₂ | —CH₂CH₃ | N | CF₃ | CH₃ | N | N—H | CH | Bond |
| 1.173 | N—CH₂CH₃ | S | —CH₂CH₃ | C—H | CF₃ | CH₃ | CH | N | N—H | bond |
| 1.174 | N—CH₂CH₃ | SO₂ | —CH₂CH₃ | C—H | CF₃ | CH₃ | CH | N | N—H | bond |
| 1.175 | N—CH₂CH₃ | S | —CH₂CH₃ | N | CF₃ | CH₃ | CH | N | N—H | bond |
| 1.176 | N—CH₂CH₃ | SO₂ | —CH₂CH₃ | N | CF₃ | CH₃ | CH | N | N—H | bond |
| 1.177 | N—CH₂CH₃ | S | —CH₂CH₃ | C—H | CF₃ | CH₃ | N | S | N | bond |
| 1.178 | N—CH₂CH₃ | SO₂ | —CH₂CH₃ | C—H | CF₃ | CH₃ | N | S | N | bond |
| 1.179 | N—CH₂CH₃ | S | —CH₂CH₃ | N | CF₃ | CH₃ | N | S | N | bond |
| 1.180 | N—CH₂CH₃ | SO₂ | —CH₂CH₃ | N | CF₃ | CH₃ | N | S | N | bond |
| 1.181 | N—CH₂CH₃ | S | —CH₂CH₃ | C—H | CF₃ | CH₃ | N | NH | N | bond |
| 1.182 | N—CH₂CH₃ | SO₂ | —CH₂CH₃ | C—H | CF₃ | CH₃ | N | NH | N | bond |
| 1.183 | N—CH₂CH₃ | S | —CH₂CH₃ | N | CF₃ | CH₃ | N | NH | N | bond |
| 1.184 | N—CH₂CH₃ | SO₂ | —CH₂CH₃ | N | CF₃ | CH₃ | N | NH | N | bond |
| 1.185 | N—CH₂CH₃ | S | —CH₂CH₃ | C—H | CF₃ | CH₃ | N | N—CH₃ | N | bond |
| 1.186 | N—CH₂CH₃ | SO₂ | —CH₂CH₃ | C—H | CF₃ | CH₃ | N | N—CH₃ | N | bond |
| 1.187 | N—CH₂CH₃ | S | —CH₂CH₃ | N | CF₃ | CH₃ | N | N—CH₃ | N | bond |
| 1.188 | N—CH₂CH₃ | SO₂ | —CH₂CH₃ | N | CF₃ | CH₃ | N | N—CH₃ | N | bond |
| 1.189 | N—CH₂CH₃ | S | —CH₂CH₃ | C—H | CF₃ | CH₃ | N | N | N—CH₃ | bond |
| 1.190 | N—CH₂CH₃ | SO₂ | —CH₂CH₃ | C—H | CF₃ | CH₃ | N | N | N—CH₃ | bond |
| 1.191 | N—CH₂CH₃ | S | —CH₂CH₃ | N | CF₃ | CH₃ | N | N | N—CH₃ | bond |
| 1.192 | N—CH₂CH₃ | SO₂ | —CH₂CH₃ | N | CF₃ | CH₃ | N | N | N—CH₃ | bond |
| 1.193 | N—CH₂CH₃ | S | —CH₂CH₃ | C—H | CF₃ | CH₃ | N—CH₃ | N | N | bond |
| 1.194 | N—CH₂CH₃ | SO₂ | —CH₂CH₃ | C—H | CF₃ | CH₃ | N—CH₃ | N | N | bond |
| 1.195 | N—CH₂CH₃ | S | —CH₂CH₃ | N | CF₃ | CH₃ | N—CH₃ | N | N | bond |
| 1.196 | N—CH₂CH₃ | SO₂ | —CH₂CH₃ | N | CF₃ | CH₃ | N—CH₃ | N | N | bond |
| 1.197 | N—CH₂CH₃ | S | —CH₂CH₃ | C—H | CF₃ | CH₃ | CH | C—CF3 | CH | CH |
| 1.198 | N—CH₂CH₃ | SO₂ | —CH₂CH₃ | C—H | CF₃ | CH₃ | CH | C—CF₃ | CH | CH |
| 1.199 | N—CH₂CH₃ | S | —CH₂CH₃ | N | CF₃ | CH₃ | CH | C—CF₃ | CH | CH |
| 1.200 | N—CH₂CH₃ | SO₂ | —CH₂CH₃ | N | CF₃ | CH₃ | CH | C—CF₃ | CH | CH |
| 1.201 | N—CH₂CH₃ | S | —CH₂CH₃ | C—H | CF₃ | CH₃ | CH | C—F | CH | CH |
| 1.202 | N—CH₂CH₃ | SO₂ | —CH₂CH₃ | C—H | CF₃ | CH₃ | CH | C—F | CH | CH |
| 1.203 | N—CH₂CH₃ | S | —CH₂CH₃ | N | CF₃ | CH₃ | CH | C—F | CH | CH |
| 1.204 | N—CH₂CH₃ | SO₂ | —CH₂CH₃ | N | CF₃ | CH₃ | CH | C—F | CH | CH |
| 1.205 | N—CH₂CH₃ | S | —CH₂CH₃ | C—H | CF₃ | CH₃ | N | C—H | S | bond |

TABLE 1-continued

| Comp. No. | G$_3$ | X | R$_1$ | A | R$_2$ | R$_5$ | L$_1$ | L$_2$ | L$_3$ | L$_4$ |
|---|---|---|---|---|---|---|---|---|---|---|
| 1.206 | N—CH$_2$CH$_3$ | SO$_2$ | —CH$_2$CH$_3$ | C—H | CF$_3$ | CH$_3$ | N | C—H | S | bond |
| 1.207 | N—CH$_2$CH$_3$ | S | —CH$_2$CH$_3$ | N | CF$_3$ | CH$_3$ | N | C—H | S | bond |
| 1.208 | N—CH$_2$CH$_3$ | SO$_2$ | —CH$_2$CH$_3$ | N | CF$_3$ | CH$_3$ | N | C—H | S | bond |
| 1.209 | N—CH$_2$CH$_3$ | S | —CH$_2$CH$_3$ | C—H | CF$_3$ | CH$_3$ | N | C—CH$_3$ | S | bond |
| 1.210 | N—CH$_2$CH$_3$ | SO$_2$ | —CH$_2$CH$_3$ | C—H | CF$_3$ | CH$_3$ | N | C—CH$_3$ | S | bond |
| 1.211 | N—CH$_2$CH$_3$ | S | —CH$_2$CH$_3$ | N | CF$_3$ | CH$_3$ | N | C—CH$_3$ | S | bond |
| 1.212 | N—CH$_2$CH$_3$ | SO$_2$ | —CH$_2$CH$_3$ | N | CF$_3$ | CH$_3$ | N | C—CH$_3$ | S | bond |
| 1.213 | N—CH$_2$CH$_3$ | S | —CH$_2$CH$_3$ | C—H | CF$_3$ | CH$_3$ | N | C—CF$_3$ | S | bond |
| 1.214 | N—CH$_2$CH$_3$ | SO$_2$ | —CH$_2$CH$_3$ | C—H | CF$_3$ | CH$_3$ | N | C—CF$_3$ | S | bond |
| 1.215 | N—CH$_2$CH$_3$ | S | —CH$_2$CH$_3$ | N | CF$_3$ | CH$_3$ | N | C—CF$_3$ | S | bond |
| 1.216 | N—CH$_2$CH$_3$ | SO$_2$ | —CH$_2$CH$_3$ | N | CF$_3$ | CH$_3$ | N | C—CF$_3$ | S | bond |
| 1.217 | N—CH$_2$CH$_3$ | S | —CH$_2$CH$_3$ | C—H | CF$_3$ | CH$_3$ | S | C—H | N | bond |
| 1.218 | N—CH$_2$CH$_3$ | SO$_2$ | —CH$_2$CH$_3$ | C—H | CF$_3$ | CH$_3$ | S | C—H | N | bond |
| 1.219 | N—CH$_2$CH$_3$ | S | —CH$_2$CH$_3$ | N | CF$_3$ | CH$_3$ | S | C—H | N | bond |
| 1.220 | N—CH$_2$CH$_3$ | SO$_2$ | —CH$_2$CH$_3$ | N | CF$_3$ | CH$_3$ | S | C—H | N | bond |
| 1.221 | N—CH$_2$CH$_3$ | S | —CH$_2$CH$_3$ | C—H | CF$_3$ | CH$_3$ | S | C—CH$_3$ | N | bond |
| 1.222 | N—CH$_2$CH$_3$ | SO$_2$ | —CH$_2$CH$_3$ | C—H | CF$_3$ | CH$_3$ | S | C—CH$_3$ | N | bond |
| 1.223 | N—CH$_2$CH$_3$ | S | —CH$_2$CH$_3$ | N | CF$_3$ | CH$_3$ | S | C—CH$_3$ | N | bond |
| 1.224 | N—CH$_2$CH$_3$ | SO$_2$ | —CH$_2$CH$_3$ | N | CF$_3$ | CH$_3$ | S | C—CH$_3$ | N | bond |
| 1.225 | N—CH$_2$CH$_3$ | S | —CH$_2$CH$_3$ | C—H | CF$_3$ | CH$_3$ | S | C—CF$_3$ | N | bond |
| 1.226 | N—CH$_2$CH$_3$ | SO$_2$ | —CH$_2$CH$_3$ | C—H | CF$_3$ | CH$_3$ | S | C—CF$_3$ | N | bond |
| 1.227 | N—CH$_2$CH$_3$ | S | —CH$_2$CH$_3$ | N | CF$_3$ | CH$_3$ | S | C—CF$_3$ | N | bond |
| 1.228 | N—CH$_2$CH$_3$ | SO$_2$ | —CH$_2$CH$_3$ | N | CF$_3$ | CH$_3$ | S | C—CF$_3$ | N | bond |
| 1.229 | N—CH$_2$CH$_3$ | S | —CH$_2$CH$_3$ | C—H | CF$_3$ | CH$_3$ | N—H | C—CF$_3$ | N | bond |
| 1.230 | N—CH$_2$CH$_3$ | SO$_2$ | —CH$_2$CH$_3$ | C—H | CF$_3$ | CH$_3$ | N—H | C—CF$_3$ | N | bond |
| 1.231 | N—CH$_2$CH$_3$ | S | —CH$_2$CH$_3$ | N | CF$_3$ | CH$_3$ | N—H | C—CF$_3$ | N | bond |
| 1.232 | N—CH$_2$CH$_3$ | SO$_2$ | —CH$_2$CH$_3$ | N | CF$_3$ | CH$_3$ | N—H | C—CF$_3$ | N | bond |
| 1.233 | N—CH$_2$CH$_3$ | S | —CH$_2$CH$_3$ | C—H | CF$_3$ | CH$_3$ | N—H | C—CH$_3$ | N | bond |
| 1.234 | N—CH$_2$CH$_3$ | SO$_2$ | —CH$_2$CH$_3$ | C—H | CF$_3$ | CH$_3$ | N—H | C—CH$_3$ | N | bond |
| 1.235 | N—CH$_2$CH$_3$ | S | —CH$_2$CH$_3$ | N | CF$_3$ | CH$_3$ | N—H | C—CH$_3$ | N | bond |
| 1.236 | N—CH$_2$CH$_3$ | SO$_2$ | —CH$_2$CH$_3$ | N | CF$_3$ | CH$_3$ | N—H | C—CH$_3$ | N | bond |
| 1.237 | N—CH$_2$CH$_3$ | S | —CH$_2$CH$_3$ | C—H | CF$_3$ | CH$_3$ | N—H | CH | N | bond |
| 1.238 | N—CH$_2$CH$_3$ | SO$_2$ | —CH$_2$CH$_3$ | C—H | CF$_3$ | CH$_3$ | N—H | CH | N | bond |
| 1.239 | N—CH$_2$CH$_3$ | S | —CH$_2$CH$_3$ | N | CF$_3$ | CH$_3$ | N—H | CH | N | bond |
| 1.240 | N—CH$_2$CH$_3$ | SO$_2$ | —CH$_2$CH$_3$ | N | CF$_3$ | CH$_3$ | N—H | CH | N | bond |
| 1.241 | N—CH$_2$CH$_3$ | S | —CH$_2$CH$_3$ | C—H | CF$_3$ | CH$_3$ | N—CH$_3$ | CH | N | bond |
| 1.242 | N—CH$_2$CH$_3$ | SO$_2$ | —CH$_2$CH$_3$ | C—H | CF$_3$ | CH$_3$ | N—CH$_3$ | CH | N | bond |
| 1.243 | N—CH$_2$CH$_3$ | S | —CH$_2$CH$_3$ | N | CF$_3$ | CH$_3$ | N—CH$_3$ | CH | N | bond |
| 1.244 | N—CH$_2$CH$_3$ | SO$_2$ | —CH$_2$CH$_3$ | N | CF$_3$ | CH$_3$ | N—CH$_3$ | CH | N | bond |
| 1.245 | N—CH$_2$CH$_3$ | S | —CH$_2$CH$_3$ | C—H | CF$_3$ | CH$_3$ | N—CH$_3$ | C—CH$_3$ | N | bond |
| 1.246 | N—CH$_2$CH$_3$ | SO$_2$ | —CH$_2$CH$_3$ | C—H | CF$_3$ | CH$_3$ | N—CH$_3$ | C—CH$_3$ | N | bond |
| 1.247 | N—CH$_2$CH$_3$ | S | —CH$_2$CH$_3$ | N | CF$_3$ | CH$_3$ | N—CH$_3$ | C—CH$_3$ | N | bond |
| 1.248 | N—CH$_2$CH$_3$ | SO$_2$ | —CH$_2$CH$_3$ | N | CF$_3$ | CH$_3$ | N—CH$_3$ | C—CH$_3$ | N | bond |
| 1.249 | N—CH$_2$CH$_3$ | S | —CH$_2$CH$_3$ | C—H | CF$_3$ | CH$_3$ | N—CH$_3$ | C—CF$_3$ | N | bond |
| 1.250 | N—CH$_2$CH$_3$ | SO$_2$ | —CH$_2$CH$_3$ | C—H | CF$_3$ | CH$_3$ | N—CH$_3$ | C—CF$_3$ | N | bond |
| 1.251 | N—CH$_2$CH$_3$ | S | —CH$_2$CH$_3$ | N | CF$_3$ | CH$_3$ | N—CH$_3$ | C—CF$_3$ | N | bond |
| 1.252 | N—CH$_2$CH$_3$ | SO$_2$ | —CH$_2$CH$_3$ | N | CF$_3$ | CH$_3$ | N—CH$_3$ | C—CF$_3$ | N | bond |
| 1.253 | N—CH$_2$CH$_3$ | S | —CH$_2$CH$_3$ | C—H | CF$_3$ | CH$_3$ | N | CH | N—CH$_3$ | bond |
| 1.254 | N—CH$_2$CH$_3$ | SO$_2$ | —CH$_2$CH$_3$ | C—H | CF$_3$ | CH$_3$ | N | CH | N—CH$_3$ | bond |
| 1.255 | N—CH$_2$CH$_3$ | S | —CH$_2$CH$_3$ | N | CF$_3$ | CH$_3$ | N | CH | N—CH$_3$ | bond |
| 1.256 | N—CH$_2$CH$_3$ | SO$_2$ | —CH$_2$CH$_3$ | N | CF$_3$ | CH$_3$ | N | CH | N—CH$_3$ | bond |
| 1.257 | N—CH$_2$CH$_3$ | S | —CH$_2$CH$_3$ | C—H | CF$_3$ | CH$_3$ | N | C—CH$_3$ | N—CH$_3$ | bond |
| 1.258 | N—CH$_2$CH$_3$ | SO$_2$ | —CH$_2$CH$_3$ | C—H | CF$_3$ | CH$_3$ | N | C—CH$_3$ | N—CH$_3$ | bond |
| 1.259 | N—CH$_2$CH$_3$ | S | —CH$_2$CH$_3$ | N | CF$_3$ | CH$_3$ | N | C—CH$_3$ | N—CH$_3$ | bond |
| 1.260 | N—CH$_2$CH$_3$ | SO$_2$ | —CH$_2$CH$_3$ | N | CF$_3$ | CH$_3$ | N | C—CH$_3$ | N—CH$_3$ | bond |
| 1.261 | N—CH$_2$CH$_3$ | S | —CH$_2$CH$_3$ | C—H | CF$_3$ | CH$_3$ | N | C—CF$_3$ | N—CH$_3$ | bond |
| 1.262 | N—CH$_2$CH$_3$ | SO$_2$ | —CH$_2$CH$_3$ | C—H | CF$_3$ | CH$_3$ | N | C—CF$_3$ | N—CH$_3$ | bond |
| 1.263 | N—CH$_2$CH$_3$ | S | —CH$_2$CH$_3$ | N | CF$_3$ | CH$_3$ | N | C—CF$_3$ | N—CH$_3$ | bond |
| 1.264 | N—CH$_2$CH$_3$ | SO$_2$ | —CH$_2$CH$_3$ | N | CF$_3$ | CH$_3$ | N | C—CF$_3$ | N—CH$_3$ | bond | and the N-oxides or tautomers of the compounds of Table 1.

Table 2: This table discloses the 264 compounds of the formula I-1b:

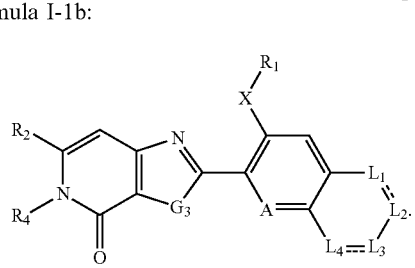

(I-1b)

TABLE 2

| Comp. No. | G$_3$ | X | R$_1$ | A | R$_2$ | R$_4$ | L$_1$ | L$_2$ | L$_3$ | L$_4$ |
|---|---|---|---|---|---|---|---|---|---|---|
| 2.001 | N—CH$_3$ | S | —CH$_2$CH$_3$ | C—H | CF$_3$ | CH$_3$ | CH | CH | CH | CH |
| 2.002 | N—CH$_3$ | SO$_2$ | —CH$_2$CH$_3$ | C—H | CF$_3$ | CH$_3$ | CH | CH | CH | CH |
| 2.003 | N—CH$_3$ | S | —CH$_2$CH$_3$ | C—H | SCF$_3$ | CH$_3$ | CH | CH | CH | CH |
| 2.004 | N—CH$_3$ | SO$_2$ | —CH$_2$CH$_3$ | C—H | SCF$_3$ | CH$_3$ | CH | CH | CH | CH |
| 2.005 | N—CH$_3$ | S | —CH$_2$CH$_3$ | C—H | CF$_2$CF$_3$ | CH$_3$ | CH | CH | CH | CH |
| 2.006 | N—CH$_3$ | SO$_2$ | —CH$_2$CH$_3$ | C—H | CF$_2$CF$_3$ | CH$_3$ | CH | CH | CH | CH |
| 2.007 | N—CH$_3$ | S | —CH$_2$CH$_3$ | N | CF$_3$ | CH$_3$ | CH | CH | CH | CH |
| 2.008 | N—CH$_3$ | SO$_2$ | —CH$_2$CH$_3$ | N | CF$_3$ | CH$_3$ | CH | CH | CH | CH |
| 2.009 | N—CH$_3$ | S | —CH$_2$CH$_3$ | N | SCF$_3$ | CH$_3$ | CH | CH | CH | CH |
| 2.010 | N—CH$_3$ | SO$_2$ | —CH$_2$CH$_3$ | N | SCF$_3$ | CH$_3$ | CH | CH | CH | CH |
| 2.011 | N—CH$_3$ | S | —CH$_2$CH$_3$ | N | CF$_2$CF$_3$ | CH$_3$ | CH | CH | CH | CH |
| 2.012 | N—CH$_3$ | SO$_2$ | —CH$_2$CH$_3$ | N | CF$_2$CF$_3$ | CH$_3$ | CH | CH | CH | CH |
| 2.013 | N—CH$_3$ | S | —CH$_2$CH$_3$ | C—H | CF$_3$ | CH$_3$ | CH | N | N—CH$_3$ | bond |
| 2.014 | N—CH$_3$ | SO$_2$ | —CH$_2$CH$_3$ | C—H | CF$_3$ | CH$_3$ | CH | N | N—CH$_3$ | bond |
| 2.015 | N—CH$_3$ | S | —CH$_2$CH$_3$ | C—H | CF$_3$ | CH$_3$ | CH | N—CH$_3$ | N | bond |
| 2.016 | N—CH$_3$ | SO$_2$ | —CH$_2$CH$_3$ | C—H | CF$_3$ | CH$_3$ | CH | N—CH$_3$ | N | bond |
| 2.017 | N—CH$_3$ | S | —CH$_2$CH$_3$ | N | CF$_3$ | CH$_3$ | CH | N | N—CH$_3$ | bond |
| 2.018 | N—CH$_3$ | SO$_2$ | —CH$_2$CH$_3$ | N | CF$_3$ | CH$_3$ | CH | N | N—CH$_3$ | bond |
| 2.019 | N—CH$_3$ | S | —CH$_2$CH$_3$ | N | CF$_3$ | CH$_3$ | CH | N—CH$_3$ | N | bond |
| 2.020 | N—CH$_3$ | SO$_2$ | —CH$_2$CH$_3$ | N | CF$_3$ | CH$_3$ | CH | N—CH$_3$ | N | bond |
| 2.021 | N—CH$_3$ | S | —CH$_2$CH$_3$ | C—H | CF$_3$ | CH$_3$ | N | CH | CH | CH |
| 2.022 | N—CH$_3$ | SO$_2$ | —CH$_2$CH$_3$ | C—H | CF$_3$ | CH$_3$ | N | CH | CH | CH |
| 2.023 | N—CH$_3$ | S | —CH$_2$CH$_3$ | N | CF$_3$ | CH$_3$ | N | CH | CH | CH |
| 2.024 | N—CH$_3$ | SO$_2$ | —CH$_2$CH$_3$ | N | CF$_3$ | CH$_3$ | N | CH | CH | CH |
| 2.025 | N—CH$_3$ | S | —CH$_2$CH$_3$ | C—H | CF$_3$ | CH$_3$ | CH | N | CH | CH |
| 2.026 | N—CH$_3$ | SO$_2$ | —CH$_2$CH$_3$ | C—H | CF$_3$ | CH$_3$ | CH | N | CH | CH |
| 2.027 | N—CH$_3$ | S | —CH$_2$CH$_3$ | N | CF$_3$ | CH$_3$ | CH | N | CH | CH |
| 2.028 | N—CH$_3$ | SO$_2$ | —CH$_2$CH$_3$ | N | CF$_3$ | CH$_3$ | CH | N | CH | CH |
| 2.029 | N—CH$_3$ | S | —CH$_2$CH$_3$ | C—H | CF$_3$ | CH$_3$ | N—CH$_3$ | N | CH | Bond |
| 2.030 | N—CH$_3$ | SO$_2$ | —CH$_2$CH$_3$ | C—H | CF$_3$ | CH$_3$ | N—CH$_3$ | N | CH | Bond |
| 2.031 | N—CH$_3$ | S | —CH$_2$CH$_3$ | N | CF$_3$ | CH$_3$ | N—CH$_3$ | N | CH | Bond |
| 2.032 | N—CH$_3$ | SO$_2$ | —CH$_2$CH$_3$ | N | CF$_3$ | CH$_3$ | N—CH$_3$ | N | CH | Bond |
| 2.033 | N—CH$_3$ | S | —CH$_2$CH$_3$ | C—H | CF$_3$ | CH$_3$ | N | N—CH$_3$ | CH | Bond |
| 2.034 | N—CH$_3$ | SO$_2$ | —CH$_2$CH$_3$ | C—H | CF$_3$ | CH$_3$ | N | N—CH$_3$ | CH | Bond |
| 2.035 | N—CH$_3$ | S | —CH$_2$CH$_3$ | N | CF$_3$ | CH$_3$ | N | N—CH$_3$ | CH | Bond |
| 2.036 | N—CH$_3$ | SO$_2$ | —CH$_2$CH$_3$ | N | CF$_3$ | CH$_3$ | N | N—CH$_3$ | CH | Bond |
| 2.037 | N—CH$_3$ | S | —CH$_2$CH$_3$ | C—H | CF$_3$ | CH$_3$ | N | N—H | CH | Bond |
| 2.038 | N—CH$_3$ | SO$_2$ | —CH$_2$CH$_3$ | C—H | CF$_3$ | CH$_3$ | N | N—H | CH | Bond |
| 2.039 | N—CH$_3$ | S | —CH$_2$CH$_3$ | N | CF$_3$ | CH$_3$ | N | N—H | CH | Bond |
| 2.040 | N—CH$_3$ | SO$_2$ | —CH$_2$CH$_3$ | N | CF$_3$ | CH$_3$ | N | N—H | CH | Bond |
| 2.041 | N—CH$_3$ | S | —CH$_2$CH$_3$ | C—H | CF$_3$ | CH$_3$ | CH | N | N—H | bond |
| 2.042 | N—CH$_3$ | SO$_2$ | —CH$_2$CH$_3$ | C—H | CF$_3$ | CH$_3$ | CH | N | N—H | bond |
| 2.043 | N—CH$_3$ | S | —CH$_2$CH$_3$ | N | CF$_3$ | CH$_3$ | CH | N | N—H | bond |
| 2.044 | N—CH$_3$ | SO$_2$ | —CH$_2$CH$_3$ | N | CF$_3$ | CH$_3$ | CH | N | N—H | bond |
| 2.045 | N—CH$_3$ | S | —CH$_2$CH$_3$ | C—H | CF$_3$ | CH$_3$ | N | S | N | bond |
| 2.046 | N—CH$_3$ | SO$_2$ | —CH$_2$CH$_3$ | C—H | CF$_3$ | CH$_3$ | N | S | N | bond |
| 2.047 | N—CH$_3$ | S | —CH$_2$CH$_3$ | N | CF$_3$ | CH$_3$ | N | S | N | bond |
| 2.048 | N—CH$_3$ | SO$_2$ | —CH$_2$CH$_3$ | N | CF$_3$ | CH$_3$ | N | S | N | bond |
| 2.049 | N—CH$_3$ | S | —CH$_2$CH$_3$ | C—H | CF$_3$ | CH$_3$ | N | NH | N | bond |
| 2.050 | N—CH$_3$ | SO$_2$ | —CH$_2$CH$_3$ | C—H | CF$_3$ | CH$_3$ | N | NH | N | bond |
| 2.051 | N—CH$_3$ | S | —CH$_2$CH$_3$ | N | CF$_3$ | CH$_3$ | N | NH | N | bond |
| 2.052 | N—CH$_3$ | SO$_2$ | —CH$_2$CH$_3$ | N | CF$_3$ | CH$_3$ | N | NH | N | bond |
| 2.053 | N—CH$_3$ | S | —CH$_2$CH$_3$ | C—H | CF$_3$ | CH$_3$ | N | N—CH$_3$ | N | bond |
| 2.054 | N—CH$_3$ | SO$_2$ | —CH$_2$CH$_3$ | C—H | CF$_3$ | CH$_3$ | N | N—CH$_3$ | N | bond |
| 2.055 | N—CH$_3$ | S | —CH$_2$CH$_3$ | N | CF$_3$ | CH$_3$ | N | N—CH$_3$ | N | bond |
| 2.056 | N—CH$_3$ | SO$_2$ | —CH$_2$CH$_3$ | N | CF$_3$ | CH$_3$ | N | N—CH$_3$ | N | bond |
| 2.057 | N—CH$_3$ | S | —CH$_2$CH$_3$ | C—H | CF$_3$ | CH$_3$ | N | N | N—CH$_3$ | bond |
| 2.058 | N—CH$_3$ | SO$_2$ | —CH$_2$CH$_3$ | C—H | CF$_3$ | CH$_3$ | N | N | N—CH$_3$ | bond |
| 2.059 | N—CH$_3$ | S | —CH$_2$CH$_3$ | N | CF$_3$ | CH$_3$ | N | N | N—CH$_3$ | bond |
| 2.060 | N—CH$_3$ | SO$_2$ | —CH$_2$CH$_3$ | N | CF$_3$ | CH$_3$ | N | N | N—CH$_3$ | bond |
| 2.061 | N—CH$_3$ | S | —CH$_2$CH$_3$ | C—H | CF$_3$ | CH$_3$ | N—CH$_3$ | N | N | bond |
| 2.062 | N—CH$_3$ | SO$_2$ | —CH$_2$CH$_3$ | C—H | CF$_3$ | CH$_3$ | N—CH$_3$ | N | N | bond |
| 2.063 | N—CH$_3$ | S | —CH$_2$CH$_3$ | N | CF$_3$ | CH$_3$ | N—CH$_3$ | N | N | bond |
| 2.064 | N—CH$_3$ | SO$_2$ | —CH$_2$CH$_3$ | N | CF$_3$ | CH$_3$ | N—CH$_3$ | N | N | bond |
| 2.065 | N—CH$_3$ | S | —CH$_2$CH$_3$ | C—H | CF$_3$ | CH$_3$ | CH | C—CF3 | CH | CH |
| 2.066 | N—CH$_3$ | SO$_2$ | —CH$_2$CH$_3$ | C—H | CF$_3$ | CH$_3$ | CH | C—CF3 | CH | CH |
| 2.067 | N—CH$_3$ | S | —CH$_2$CH$_3$ | N | CF$_3$ | CH$_3$ | CH | C—CF3 | CH | CH |
| 2.068 | N—CH$_3$ | SO$_2$ | —CH$_2$CH$_3$ | N | CF$_3$ | CH$_3$ | CH | C—CF3 | CH | CH |
| 2.069 | N—CH$_3$ | S | —CH$_2$CH$_3$ | C—H | CF$_3$ | CH$_3$ | CH | C—F | CH | CH |
| 2.070 | N—CH$_3$ | SO$_2$ | —CH$_2$CH$_3$ | C—H | CF$_3$ | CH$_3$ | CH | C—F | CH | CH |
| 2.071 | N—CH$_3$ | S | —CH$_2$CH$_3$ | N | CF$_3$ | CH$_3$ | CH | C—F | CH | CH |
| 2.072 | N—CH$_3$ | SO$_2$ | —CH$_2$CH$_3$ | N | CF$_3$ | CH$_3$ | CH | C—F | CH | CH |
| 2.073 | N—CH$_3$ | S | —CH$_2$CH$_3$ | C—H | CF$_3$ | CH$_3$ | N | C—H | S | bond |
| 2.074 | N—CH$_3$ | SO$_2$ | —CH$_2$CH$_3$ | C—H | CF$_3$ | CH$_3$ | N | C—H | S | bond |
| 2.075 | N—CH$_3$ | S | —CH$_2$CH$_3$ | N | CF$_3$ | CH$_3$ | N | C—H | S | bond |
| 2.076 | N—CH$_3$ | SO$_2$ | —CH$_2$CH$_3$ | N | CF$_3$ | CH$_3$ | N | C—H | S | bond |
| 2.077 | N—CH$_3$ | S | —CH$_2$CH$_3$ | C—H | CF$_3$ | CH$_3$ | N | C—CH$_3$ | S | bond |
| 2.078 | N—CH$_3$ | SO$_2$ | —CH$_2$CH$_3$ | C—H | CF$_3$ | CH$_3$ | N | C—CH$_3$ | S | bond |

TABLE 2-continued

| Comp. No. | G$_3$ | X | R$_1$ | A | R$_2$ | R$_4$ | L$_1$ | L$_2$ | L$_3$ | L$_4$ |
|---|---|---|---|---|---|---|---|---|---|---|
| 2.079 | N—CH$_3$ | S | —CH$_2$CH$_3$ | N | CF$_3$ | CH$_3$ | N | C—CH$_3$ | S | bond |
| 2.080 | N—CH$_3$ | SO$_2$ | —CH$_2$CH$_3$ | N | CF$_3$ | CH$_3$ | N | C—CH$_3$ | S | bond |
| 2.081 | N—CH$_3$ | S | —CH$_2$CH$_3$ | C—H | CF$_3$ | CH$_3$ | N | C—CF$_3$ | S | bond |
| 2.082 | N—CH$_3$ | SO$_2$ | —CH$_2$CH$_3$ | C—H | CF$_3$ | CH$_3$ | N | C—CF$_3$ | S | bond |
| 2.083 | N—CH$_3$ | S | —CH$_2$CH$_3$ | N | CF$_3$ | CH$_3$ | N | C—CF$_3$ | S | bond |
| 2.084 | N—CH$_3$ | SO$_2$ | —CH$_2$CH$_3$ | N | CF$_3$ | CH$_3$ | N | C—CF$_3$ | S | bond |
| 2.085 | N—CH$_3$ | S | —CH$_2$CH$_3$ | C—H | CF$_3$ | CH$_3$ | S | C—H | N | bond |
| 2.086 | N—CH$_3$ | SO$_2$ | —CH$_2$CH$_3$ | C—H | CF$_3$ | CH$_3$ | S | C—H | N | bond |
| 2.087 | N—CH$_3$ | S | —CH$_2$CH$_3$ | N | CF$_3$ | CH$_3$ | S | C—H | N | bond |
| 2.088 | N—CH$_3$ | SO$_2$ | —CH$_2$CH$_3$ | N | CF$_3$ | CH$_3$ | S | C—H | N | bond |
| 2.089 | N—CH$_3$ | S | —CH$_2$CH$_3$ | C—H | CF$_3$ | CH$_3$ | S | C—CH$_3$ | N | bond |
| 2.090 | N—CH$_3$ | SO$_2$ | —CH$_2$CH$_3$ | C—H | CF$_3$ | CH$_3$ | S | C—CH$_3$ | N | bond |
| 2.091 | N—CH$_3$ | S | —CH$_2$CH$_3$ | N | CF$_3$ | CH$_3$ | S | C—CH$_3$ | N | bond |
| 2.092 | N—CH$_3$ | SO$_2$ | —CH$_2$CH$_3$ | N | CF$_3$ | CH$_3$ | S | C—CH$_3$ | N | bond |
| 2.093 | N—CH$_3$ | S | —CH$_2$CH$_3$ | C—H | CF$_3$ | CH$_3$ | S | C—CF$_3$ | N | bond |
| 2.094 | N—CH$_3$ | SO$_2$ | —CH$_2$CH$_3$ | C—H | CF$_3$ | CH$_3$ | S | C—CF$_3$ | N | bond |
| 2.095 | N—CH$_3$ | S | —CH$_2$CH$_3$ | N | CF$_3$ | CH$_3$ | S | C—CF$_3$ | N | bond |
| 2.096 | N—CH$_3$ | SO$_2$ | —CH$_2$CH$_3$ | N | CF$_3$ | CH$_3$ | S | C—CF$_3$ | N | bond |
| 2.097 | N—CH$_3$ | S | —CH$_2$CH$_3$ | C—H | CF$_3$ | CH$_3$ | N—H | C—CF$_3$ | N | bond |
| 2.098 | N—CH$_3$ | SO$_2$ | —CH$_2$CH$_3$ | C—H | CF$_3$ | CH$_3$ | N—H | C—CF$_3$ | N | bond |
| 2.099 | N—CH$_3$ | S | —CH$_2$CH$_3$ | N | CF$_3$ | CH$_3$ | N—H | C—CF$_3$ | N | bond |
| 2.100 | N—CH$_3$ | SO$_2$ | —CH$_2$CH$_3$ | N | CF$_3$ | CH$_3$ | N—H | C—CF$_3$ | N | bond |
| 2.101 | N—CH$_3$ | S | —CH$_2$CH$_3$ | C—H | CF$_3$ | CH$_3$ | N—H | C—CH$_3$ | N | bond |
| 2.102 | N—CH$_3$ | SO$_2$ | —CH$_2$CH$_3$ | C—H | CF$_3$ | CH$_3$ | N—H | C—CH$_3$ | N | bond |
| 2.103 | N—CH$_3$ | S | —CH$_2$CH$_3$ | N | CF$_3$ | CH$_3$ | N—H | C—CH$_3$ | N | bond |
| 2.104 | N—CH$_3$ | SO$_2$ | —CH$_2$CH$_3$ | N | CF$_3$ | CH$_3$ | N—H | C—CH$_3$ | N | bond |
| 2.105 | N—CH$_3$ | S | —CH$_2$CH$_3$ | C—H | CF$_3$ | CH$_3$ | N—H | CH | N | bond |
| 2.106 | N—CH$_3$ | SO$_2$ | —CH$_2$CH$_3$ | C—H | CF$_3$ | CH$_3$ | N—H | CH | N | bond |
| 2.107 | N—CH$_3$ | S | —CH$_2$CH$_3$ | N | CF$_3$ | CH$_3$ | N—H | CH | N | bond |
| 2.108 | N—CH$_3$ | SO$_2$ | —CH$_2$CH$_3$ | N | CF$_3$ | CH$_3$ | N—H | CH | N | bond |
| 2.109 | N—CH$_3$ | S | —CH$_2$CH$_3$ | C—H | CF$_3$ | CH$_3$ | N—CH$_3$ | CH | N | bond |
| 2.110 | N—CH$_3$ | SO$_2$ | —CH$_2$CH$_3$ | C—H | CF$_3$ | CH$_3$ | N—CH$_3$ | CH | N | bond |
| 2.111 | N—CH$_3$ | S | —CH$_2$CH$_3$ | N | CF$_3$ | CH$_3$ | N—CH$_3$ | CH | N | bond |
| 2.112 | N—CH$_3$ | SO$_2$ | —CH$_2$CH$_3$ | N | CF$_3$ | CH$_3$ | N—CH$_3$ | CH | N | bond |
| 2.113 | N—CH$_3$ | S | —CH$_2$CH$_3$ | C—H | CF$_3$ | CH$_3$ | N—CH$_3$ | C—CH$_3$ | N | bond |
| 2.114 | N—CH$_3$ | SO$_2$ | —CH$_2$CH$_3$ | C—H | CF$_3$ | CH$_3$ | N—CH$_3$ | C—CH$_3$ | N | bond |
| 2.115 | N—CH$_3$ | S | —CH$_2$CH$_3$ | N | CF$_3$ | CH$_3$ | N—CH$_3$ | C—CH$_3$ | N | bond |
| 2.116 | N—CH$_3$ | SO$_2$ | —CH$_2$CH$_3$ | N | CF$_3$ | CH$_3$ | N—CH$_3$ | C—CH$_3$ | N | bond |
| 2.117 | N—CH$_3$ | S | —CH$_2$CH$_3$ | C—H | CF$_3$ | CH$_3$ | N—CH$_3$ | C—CF$_3$ | N | bond |
| 2.118 | N—CH$_3$ | SO$_2$ | —CH$_2$CH$_3$ | C—H | CF$_3$ | CH$_3$ | N—CH$_3$ | C—CF$_3$ | N | bond |
| 2.119 | N—CH$_3$ | S | —CH$_2$CH$_3$ | N | CF$_3$ | CH$_3$ | N—CH$_3$ | C—CF$_3$ | N | bond |
| 2.120 | N—CH$_3$ | SO$_2$ | —CH$_2$CH$_3$ | N | CF$_3$ | CH$_3$ | N—CH$_3$ | C—CF$_3$ | N | bond |
| 2.121 | N—CH$_3$ | S | —CH$_2$CH$_3$ | C—H | CF$_3$ | CH$_3$ | N | CH | N—CH$_3$ | bond |
| 2.122 | N—CH$_3$ | SO$_2$ | —CH$_2$CH$_3$ | C—H | CF$_3$ | CH$_3$ | N | CH | N—CH$_3$ | bond |
| 2.123 | N—CH$_3$ | S | —CH$_2$CH$_3$ | N | CF$_3$ | CH$_3$ | N | CH | N—CH$_3$ | bond |
| 2.124 | N—CH$_3$ | SO$_2$ | —CH$_2$CH$_3$ | N | CF$_3$ | CH$_3$ | N | CH | N—CH$_3$ | bond |
| 2.125 | N—CH$_3$ | S | —CH$_2$CH$_3$ | C—H | CF$_3$ | CH$_3$ | N | C—CH$_3$ | N—CH$_3$ | bond |
| 2.126 | N—CH$_3$ | SO$_2$ | —CH$_2$CH$_3$ | C—H | CF$_3$ | CH$_3$ | N | C—CH$_3$ | N—CH$_3$ | bond |
| 2.127 | N—CH$_3$ | S | —CH$_2$CH$_3$ | N | CF$_3$ | CH$_3$ | N | C—CH$_3$ | N—CH$_3$ | bond |
| 2.128 | N—CH$_3$ | SO$_2$ | —CH$_2$CH$_3$ | N | CF$_3$ | CH$_3$ | N | C—CH$_3$ | N—CH$_3$ | bond |
| 2.129 | N—CH$_3$ | S | —CH$_2$CH$_3$ | C—H | CF$_3$ | CH$_3$ | N | C—CF$_3$ | N—CH$_3$ | bond |
| 2.130 | N—CH$_3$ | SO$_2$ | —CH$_2$CH$_3$ | C—H | CF$_3$ | CH$_3$ | N | C—CF$_3$ | N—CH$_3$ | bond |
| 2.131 | N—CH$_3$ | S | —CH$_2$CH$_3$ | N | CF$_3$ | CH$_3$ | N | C—CF$_3$ | N—CH$_3$ | bond |
| 2.132 | N—CH$_3$ | SO$_2$ | —CH$_2$CH$_3$ | N | CF$_3$ | CH$_3$ | N | C—CF$_3$ | N—CH$_3$ | Bond |
| 2.133 | N—CH$_2$CH$_3$ | S | —CH$_2$CH$_3$ | C—H | CF$_3$ | CH$_3$ | CH | CH | CH | CH |
| 2.134 | N—CH$_2$CH$_3$ | SO$_2$ | —CH$_2$CH$_3$ | C—H | CF$_3$ | CH$_3$ | CH | CH | CH | CH |
| 2.135 | N—CH$_2$CH$_3$ | S | —CH$_2$CH$_3$ | C—H | SCF$_3$ | CH$_3$ | CH | CH | CH | CH |
| 2.136 | N—CH$_2$CH$_3$ | SO$_2$ | —CH$_2$CH$_3$ | C—H | SCF$_3$ | CH$_3$ | CH | CH | CH | CH |
| 2.137 | N—CH$_2$CH$_3$ | S | —CH$_2$CH$_3$ | C—H | CF$_2$CF$_3$ | CH$_3$ | CH | CH | CH | CH |
| 2.138 | N—CH$_2$CH$_3$ | SO$_2$ | —CH$_2$CH$_3$ | C—H | CF$_2$CF$_3$ | CH$_3$ | CH | CH | CH | CH |
| 2.139 | N—CH$_2$CH$_3$ | S | —CH$_2$CH$_3$ | N | CF$_3$ | CH$_3$ | CH | CH | CH | CH |
| 2.140 | N—CH$_2$CH$_3$ | SO$_2$ | —CH$_2$CH$_3$ | N | CF$_3$ | CH$_3$ | CH | CH | CH | CH |
| 2.141 | N—CH$_2$CH$_3$ | S | —CH$_2$CH$_3$ | N | SCF$_3$ | CH$_3$ | CH | CH | CH | CH |
| 2.142 | N—CH$_2$CH$_3$ | SO$_2$ | —CH$_2$CH$_3$ | N | SCF$_3$ | CH$_3$ | CH | CH | CH | CH |
| 2.143 | N—CH$_2$CH$_3$ | S | —CH$_2$CH$_3$ | N | CF$_2$CF$_3$ | CH$_3$ | CH | CH | CH | CH |
| 2.144 | N—CH$_2$CH$_3$ | SO$_2$ | —CH$_2$CH$_3$ | N | CF$_2$CF$_3$ | CH$_3$ | CH | CH | CH | CH |
| 2.145 | N—CH$_2$CH$_3$ | S | —CH$_2$CH$_3$ | C—H | CF$_3$ | CH$_3$ | CH | N | N—CH$_3$ | bond |
| 2.146 | N—CH$_2$CH$_3$ | SO$_2$ | —CH$_2$CH$_3$ | C—H | CF$_3$ | CH$_3$ | CH | N | N—CH$_3$ | bond |
| 2.147 | N—CH$_2$CH$_3$ | S | —CH$_2$CH$_3$ | C—H | CF$_3$ | CH$_3$ | CH | N—CH$_3$ | N | bond |
| 2.148 | N—CH$_2$CH$_3$ | SO$_2$ | —CH$_2$CH$_3$ | C—H | CF$_3$ | CH$_3$ | CH | N—CH$_3$ | N | bond |
| 2.149 | N—CH$_2$CH$_3$ | S | —CH$_2$CH$_3$ | N | CF$_3$ | CH$_3$ | CH | N | N—CH$_3$ | bond |
| 2.15 | N—CH$_2$CH$_3$ | SO$_2$ | —CH$_2$CH$_3$ | N | CF$_3$ | CH$_3$ | CH | N | N—CH$_3$ | bond |
| 2.151 | N—CH$_2$CH$_3$ | S | —CH$_2$CH$_3$ | N | CF$_3$ | CH$_3$ | CH | N—CH$_3$ | N | bond |
| 2.152 | N—CH$_2$CH$_3$ | SO$_2$ | —CH$_2$CH$_3$ | N | CF$_3$ | CH$_3$ | CH | N—CH$_3$ | N | bond |
| 2.153 | N—CH$_2$CH$_3$ | S | —CH$_2$CH$_3$ | C—H | CF$_3$ | CH$_3$ | N | CH | CH | CH |
| 2.154 | N—CH$_2$CH$_3$ | SO$_2$ | —CH$_2$CH$_3$ | C—H | CF$_3$ | CH$_3$ | N | CH | CH | CH |
| 2.155 | N—CH$_2$CH$_3$ | S | —CH$_2$CH$_3$ | N | CF$_3$ | CH$_3$ | N | CH | CH | CH |
| 2.156 | N—CH$_2$CH$_3$ | SO$_2$ | —CH$_2$CH$_3$ | N | CF$_3$ | CH$_3$ | N | CH | CH | CH |

TABLE 2-continued

| Comp. No. | G$_3$ | X | R$_1$ | A | R$_2$ | R$_4$ | L$_1$ | L$_2$ | L$_3$ | L$_4$ |
|---|---|---|---|---|---|---|---|---|---|---|
| 2.157 | N—CH$_2$CH$_3$ | S | —CH$_2$CH$_3$ | C—H | CF$_3$ | CH$_3$ | CH | N | CH | CH |
| 2.158 | N—CH$_2$CH$_3$ | SO$_2$ | —CH$_2$CH$_3$ | C—H | CF$_3$ | CH$_3$ | CH | N | CH | CH |
| 2.159 | N—CH$_2$CH$_3$ | S | —CH$_2$CH$_3$ | N | CF$_3$ | CH$_3$ | CH | N | CH | CH |
| 2.160 | N—CH$_2$CH$_3$ | SO$_2$ | —CH$_2$CH$_3$ | N | CF$_3$ | CH$_3$ | CH | N | CH | CH |
| 2.161 | N—CH$_2$CH$_3$ | S | —CH$_2$CH$_3$ | C—H | CF$_3$ | CH$_3$ | N—CH$_3$ | N | CH | Bond |
| 2.162 | N—CH$_2$CH$_3$ | SO$_2$ | —CH$_2$CH$_3$ | C—H | CF$_3$ | CH$_3$ | N—CH$_3$ | N | CH | Bond |
| 2.163 | N—CH$_2$CH$_3$ | S | —CH$_2$CH$_3$ | N | CF$_3$ | CH$_3$ | N—CH$_3$ | N | CH | Bond |
| 2.164 | N—CH$_2$CH$_3$ | SO$_2$ | —CH$_2$CH$_3$ | N | CF$_3$ | CH$_3$ | N—CH$_3$ | N | CH | Bond |
| 2.165 | N—CH$_2$CH$_3$ | S | —CH$_2$CH$_3$ | C—H | CF$_3$ | CH$_3$ | N | N—CH$_3$ | CH | Bond |
| 2.166 | N—CH$_2$CH$_3$ | SO$_2$ | —CH$_2$CH$_3$ | C—H | CF$_3$ | CH$_3$ | N | N—CH$_3$ | CH | Bond |
| 2.167 | N—CH$_2$CH$_3$ | S | —CH$_2$CH$_3$ | N | CF$_3$ | CH$_3$ | N | N—CH$_3$ | CH | Bond |
| 2.168 | N—CH$_2$CH$_3$ | SO$_2$ | —CH$_2$CH$_3$ | N | CF$_3$ | CH$_3$ | N | N—CH$_3$ | CH | Bond |
| 2.169 | N—CH$_2$CH$_3$ | S | —CH$_2$CH$_3$ | C—H | CF$_3$ | CH$_3$ | N | N—H | CH | Bond |
| 2.170 | N—CH$_2$CH$_3$ | SO$_2$ | —CH$_2$CH$_3$ | C—H | CF$_3$ | CH$_3$ | N | N—H | CH | Bond |
| 2.171 | N—CH$_2$CH$_3$ | S | —CH$_2$CH$_3$ | N | CF$_3$ | CH$_3$ | N | N—H | CH | Bond |
| 2.172 | N—CH$_2$CH$_3$ | SO$_2$ | —CH$_2$CH$_3$ | N | CF$_3$ | CH$_3$ | N | N—H | CH | Bond |
| 2.173 | N—CH$_2$CH$_3$ | S | —CH$_2$CH$_3$ | C—H | CF$_3$ | CH$_3$ | CH | N | N—H | bond |
| 2.174 | N—CH$_2$CH$_3$ | SO$_2$ | —CH$_2$CH$_3$ | C—H | CF$_3$ | CH$_3$ | CH | N | N—H | bond |
| 2.175 | N—CH$_2$CH$_3$ | S | —CH$_2$CH$_3$ | N | CF$_3$ | CH$_3$ | CH | N | N—H | bond |
| 2.176 | N—CH$_2$CH$_3$ | SO$_2$ | —CH$_2$CH$_3$ | N | CF$_3$ | CH$_3$ | CH | N | N—H | bond |
| 2.177 | N—CH$_2$CH$_3$ | S | —CH$_2$CH$_3$ | C—H | CF$_3$ | CH$_3$ | N | S | N | bond |
| 2.178 | N—CH$_2$CH$_3$ | SO$_2$ | —CH$_2$CH$_3$ | C—H | CF$_3$ | CH$_3$ | N | S | N | bond |
| 2.179 | N—CH$_2$CH$_3$ | S | —CH$_2$CH$_3$ | N | CF$_3$ | CH$_3$ | N | S | N | bond |
| 2.180 | N—CH$_2$CH$_3$ | SO$_2$ | —CH$_2$CH$_3$ | N | CF$_3$ | CH$_3$ | N | S | N | bond |
| 2.181 | N—CH$_2$CH$_3$ | S | —CH$_2$CH$_3$ | C—H | CF$_3$ | CH$_3$ | N | NH | N | bond |
| 2.182 | N—CH$_2$CH$_3$ | SO$_2$ | —CH$_2$CH$_3$ | C—H | CF$_3$ | CH$_3$ | N | NH | N | bond |
| 2.183 | N—CH$_2$CH$_3$ | S | —CH$_2$CH$_3$ | N | CF$_3$ | CH$_3$ | N | NH | N | bond |
| 2.184 | N—CH$_2$CH$_3$ | SO$_2$ | —CH$_2$CH$_3$ | N | CF$_3$ | CH$_3$ | N | NH | N | bond |
| 2.185 | N—CH$_2$CH$_3$ | S | —CH$_2$CH$_3$ | C—H | CF$_3$ | CH$_3$ | N | N—CH$_3$ | N | bond |
| 2.186 | N—CH$_2$CH$_3$ | SO$_2$ | —CH$_2$CH$_3$ | C—H | CF$_3$ | CH$_3$ | N | N—CH$_3$ | N | bond |
| 2.187 | N—CH$_2$CH$_3$ | S | —CH$_2$CH$_3$ | N | CF$_3$ | CH$_3$ | N | N—CH$_3$ | N | bond |
| 2.188 | N—CH$_2$CH$_3$ | SO$_2$ | —CH$_2$CH$_3$ | N | CF$_3$ | CH$_3$ | N | N—CH$_3$ | N | bond |
| 2.189 | N—CH$_2$CH$_3$ | S | —CH$_2$CH$_3$ | C—H | CF$_3$ | CH$_3$ | N | N | N—CH$_3$ | bond |
| 2.190 | N—CH$_2$CH$_3$ | SO$_2$ | —CH$_2$CH$_3$ | C—H | CF$_3$ | CH$_3$ | N | N | N—CH$_3$ | bond |
| 2.191 | N—CH$_2$CH$_3$ | S | —CH$_2$CH$_3$ | N | CF$_3$ | CH$_3$ | N | N | N—CH$_3$ | bond |
| 2.192 | N—CH$_2$CH$_3$ | SO$_2$ | —CH$_2$CH$_3$ | N | CF$_3$ | CH$_3$ | N | N | N—CH$_3$ | bond |
| 2.193 | N—CH$_2$CH$_3$ | S | —CH$_2$CH$_3$ | C—H | CF$_3$ | CH$_3$ | N—CH$_3$ | N | N | bond |
| 2.194 | N—CH$_2$CH$_3$ | SO$_2$ | —CH$_2$CH$_3$ | C—H | CF$_3$ | CH$_3$ | N—CH$_3$ | N | N | bond |
| 2.195 | N—CH$_2$CH$_3$ | S | —CH$_2$CH$_3$ | N | CF$_3$ | CH$_3$ | N—CH$_3$ | N | N | bond |
| 2.196 | N—CH$_2$CH$_3$ | SO$_2$ | —CH$_2$CH$_3$ | N | CF$_3$ | CH$_3$ | N—CH$_3$ | N | N | bond |
| 2.197 | N—CH$_2$CH$_3$ | S | —CH$_2$CH$_3$ | C—H | CF$_3$ | CH$_3$ | CH | C—CF3 | CH | CH |
| 2.198 | N—CH$_2$CH$_3$ | SO$_2$ | —CH$_2$CH$_3$ | C—H | CF$_3$ | CH$_3$ | CH | C—CF$_3$ | CH | CH |
| 2.199 | N—CH$_2$CH$_3$ | S | —CH$_2$CH$_3$ | N | CF$_3$ | CH$_3$ | CH | C—CF$_3$ | CH | CH |
| 2.200 | N—CH$_2$CH$_3$ | SO$_2$ | —CH$_2$CH$_3$ | N | CF$_3$ | CH$_3$ | CH | C—CF$_3$ | CH | CH |
| 2.201 | N—CH$_2$CH$_3$ | S | —CH$_2$CH$_3$ | C—H | CF$_3$ | CH$_3$ | CH | C—F | CH | CH |
| 2.202 | N—CH$_2$CH$_3$ | SO$_2$ | —CH$_2$CH$_3$ | C—H | CF$_3$ | CH$_3$ | CH | C—F | CH | CH |
| 2.203 | N—CH$_2$CH$_3$ | S | —CH$_2$CH$_3$ | N | CF$_3$ | CH$_3$ | CH | C—F | CH | CH |
| 2.204 | N—CH$_2$CH$_3$ | SO$_2$ | —CH$_2$CH$_3$ | N | CF$_3$ | CH$_3$ | CH | C—F | CH | CH |
| 2.205 | N—CH$_2$CH$_3$ | S | —CH$_2$CH$_3$ | C—H | CF$_3$ | CH$_3$ | N | C—H | S | bond |
| 2.206 | N—CH$_2$CH$_3$ | SO$_2$ | —CH$_2$CH$_3$ | C—H | CF$_3$ | CH$_3$ | N | C—H | S | bond |
| 2.207 | N—CH$_2$CH$_3$ | S | —CH$_2$CH$_3$ | N | CF$_3$ | CH$_3$ | N | C—H | S | bond |
| 2.208 | N—CH$_2$CH$_3$ | SO$_2$ | —CH$_2$CH$_3$ | N | CF$_3$ | CH$_3$ | N | C—H | S | bond |
| 2.209 | N—CH$_2$CH$_3$ | S | —CH$_2$CH$_3$ | C—H | CF$_3$ | CH$_3$ | N | C—CH$_3$ | S | bond |
| 2.210 | N—CH$_2$CH$_3$ | SO$_2$ | —CH$_2$CH$_3$ | C—H | CF$_3$ | CH$_3$ | N | C—CH$_3$ | S | bond |
| 2.211 | N—CH$_2$CH$_3$ | S | —CH$_2$CH$_3$ | N | CF$_3$ | CH$_3$ | N | C—CH$_3$ | S | bond |
| 2.212 | N—CH$_2$CH$_3$ | SO$_2$ | —CH$_2$CH$_3$ | N | CF$_3$ | CH$_3$ | N | C—CH$_3$ | S | bond |
| 2.213 | N—CH$_2$CH$_3$ | S | —CH$_2$CH$_3$ | C—H | CF$_3$ | CH$_3$ | N | C—CF$_3$ | S | bond |
| 2.214 | N—CH$_2$CH$_3$ | SO$_2$ | —CH$_2$CH$_3$ | C—H | CF$_3$ | CH$_3$ | N | C—CF$_3$ | S | bond |
| 2.215 | N—CH$_2$CH$_3$ | S | —CH$_2$CH$_3$ | N | CF$_3$ | CH$_3$ | N | C—CF$_3$ | S | bond |
| 2.216 | N—CH$_2$CH$_3$ | SO$_2$ | —CH$_2$CH$_3$ | N | CF$_3$ | CH$_3$ | N | C—CF$_3$ | S | bond |
| 2.217 | N—CH$_2$CH$_3$ | S | —CH$_2$CH$_3$ | C—H | CF$_3$ | CH$_3$ | S | C—H | N | bond |
| 2.218 | N—CH$_2$CH$_3$ | SO$_2$ | —CH$_2$CH$_3$ | C—H | CF$_3$ | CH$_3$ | S | C—H | N | bond |
| 2.219 | N—CH$_2$CH$_3$ | S | —CH$_2$CH$_3$ | N | CF$_3$ | CH$_3$ | S | C—H | N | bond |
| 2.220 | N—CH$_2$CH$_3$ | SO$_2$ | —CH$_2$CH$_3$ | N | CF$_3$ | CH$_3$ | S | C—H | N | bond |
| 2.221 | N—CH$_2$CH$_3$ | S | —CH$_2$CH$_3$ | C—H | CF$_3$ | CH$_3$ | S | C—CH$_3$ | N | bond |
| 2.222 | N—CH$_2$CH$_3$ | SO$_2$ | —CH$_2$CH$_3$ | C—H | CF$_3$ | CH$_3$ | S | C—CH$_3$ | N | bond |
| 2.223 | N—CH$_2$CH$_3$ | S | —CH$_2$CH$_3$ | N | CF$_3$ | CH$_3$ | S | C—CH$_3$ | N | bond |
| 2.224 | N—CH$_2$CH$_3$ | SO$_2$ | —CH$_2$CH$_3$ | N | CF$_3$ | CH$_3$ | S | C—CH$_3$ | N | bond |
| 2.225 | N—CH$_2$CH$_3$ | S | —CH$_2$CH$_3$ | C—H | CF$_3$ | CH$_3$ | S | C—CF$_3$ | N | bond |
| 2.226 | N—CH$_2$CH$_3$ | SO$_2$ | —CH$_2$CH$_3$ | C—H | CF$_3$ | CH$_3$ | S | C—CF$_3$ | N | bond |
| 2.227 | N—CH$_2$CH$_3$ | S | —CH$_2$CH$_3$ | N | CF$_3$ | CH$_3$ | S | C—CF$_3$ | N | bond |
| 2.228 | N—CH$_2$CH$_3$ | SO$_2$ | —CH$_2$CH$_3$ | N | CF$_3$ | CH$_3$ | S | C—CF$_3$ | N | bond |
| 2.229 | N—CH$_2$CH$_3$ | S | —CH$_2$CH$_3$ | C—H | CF$_3$ | CH$_3$ | N—H | C—CF$_3$ | N | bond |
| 2.230 | N—CH$_2$CH$_3$ | SO$_2$ | —CH$_2$CH$_3$ | C—H | CF$_3$ | CH$_3$ | N—H | C—CF$_3$ | N | bond |
| 2.231 | N—CH$_2$CH$_3$ | S | —CH$_2$CH$_3$ | N | CF$_3$ | CH$_3$ | N—H | C—CF$_3$ | N | bond |
| 2.232 | N—CH$_2$CH$_3$ | SO$_2$ | —CH$_2$CH$_3$ | N | CF$_3$ | CH$_3$ | N—H | C—CF$_3$ | N | bond |
| 2.233 | N—CH$_2$CH$_3$ | S | —CH$_2$CH$_3$ | C—H | CF$_3$ | CH$_3$ | N—H | C—CH$_3$ | N | bond |
| 2.234 | N—CH$_2$CH$_3$ | SO$_2$ | —CH$_2$CH$_3$ | C—H | CF$_3$ | CH$_3$ | N—H | C—CH$_3$ | N | bond |

TABLE 2-continued

| Comp. No. | G$_3$ | X | R$_1$ | A | R$_2$ | R$_4$ | L$_1$ | L$_2$ | L$_3$ | L$_4$ |
|---|---|---|---|---|---|---|---|---|---|---|
| 2.235 | N—CH$_2$CH$_3$ | S | —CH$_2$CH$_3$ | N | CF$_3$ | CH$_3$ | N—H | C—CH$_3$ | N | bond |
| 2.236 | N—CH$_2$CH$_3$ | SO$_2$ | —CH$_2$CH$_3$ | N | CF$_3$ | CH$_3$ | N—H | C—CH$_3$ | N | bond |
| 2.237 | N—CH$_2$CH$_3$ | S | —CH$_2$CH$_3$ | C—H | CF$_3$ | CH$_3$ | N—H | CH | N | bond |
| 2.238 | N—CH$_2$CH$_3$ | SO$_2$ | —CH$_2$CH$_3$ | C—H | CF$_3$ | CH$_3$ | N—H | CH | N | bond |
| 2.239 | N—CH$_2$CH$_3$ | S | —CH$_2$CH$_3$ | N | CF$_3$ | CH$_3$ | N—H | CH | N | bond |
| 2.240 | N—CH$_2$CH$_3$ | SO$_2$ | —CH$_2$CH$_3$ | N | CF$_3$ | CH$_3$ | N—H | CH | N | bond |
| 2.241 | N—CH$_2$CH$_3$ | S | —CH$_2$CH$_3$ | C—H | CF$_3$ | CH$_3$ | N—CH$_3$ | CH | N | bond |
| 2.242 | N—CH$_2$CH$_3$ | SO$_2$ | —CH$_2$CH$_3$ | C—H | CF$_3$ | CH$_3$ | N—CH$_3$ | CH | N | bond |
| 2.243 | N—CH$_2$CH$_3$ | S | —CH$_2$CH$_3$ | N | CF$_3$ | CH$_3$ | N—CH$_3$ | CH | N | bond |
| 2.244 | N—CH$_2$CH$_3$ | SO$_2$ | —CH$_2$CH$_3$ | N | CF$_3$ | CH$_3$ | N—CH$_3$ | CH | N | bond |
| 2.245 | N—CH$_2$CH$_3$ | S | —CH$_2$CH$_3$ | C—H | CF$_3$ | CH$_3$ | N—CH$_3$ | C—CH$_3$ | N | bond |
| 2.246 | N—CH$_2$CH$_3$ | SO$_2$ | —CH$_2$CH$_3$ | C—H | CF$_3$ | CH$_3$ | N—CH$_3$ | C—CH$_3$ | N | bond |
| 2.247 | N—CH$_2$CH$_3$ | S | —CH$_2$CH$_3$ | N | CF$_3$ | CH$_3$ | N—CH$_3$ | C—CH$_3$ | N | bond |
| 2.248 | N—CH$_2$CH$_3$ | SO$_2$ | —CH$_2$CH$_3$ | N | CF$_3$ | CH$_3$ | N—CH$_3$ | C—CH$_3$ | N | bond |
| 2.249 | N—CH$_2$CH$_3$ | S | —CH$_2$CH$_3$ | C—H | CF$_3$ | CH$_3$ | N—CH$_3$ | C—CF$_3$ | N | bond |
| 2.250 | N—CH$_2$CH$_3$ | SO$_2$ | —CH$_2$CH$_3$ | C—H | CF$_3$ | CH$_3$ | N—CH$_3$ | C—CF$_3$ | N | bond |
| 2.251 | N—CH$_2$CH$_3$ | S | —CH$_2$CH$_3$ | N | CF$_3$ | CH$_3$ | N—CH$_3$ | C—CF$_3$ | N | bond |
| 2.252 | N—CH$_2$CH$_3$ | SO$_2$ | —CH$_2$CH$_3$ | N | CF$_3$ | CH$_3$ | N—CH$_3$ | C—CF$_3$ | N | bond |
| 2.253 | N—CH$_2$CH$_3$ | S | —CH$_2$CH$_3$ | C—H | CF$_3$ | CH$_3$ | N | CH | N—CH$_3$ | bond |
| 2.254 | N—CH$_2$CH$_3$ | SO$_2$ | —CH$_2$CH$_3$ | C—H | CF$_3$ | CH$_3$ | N | CH | N—CH$_3$ | bond |
| 2.255 | N—CH$_2$CH$_3$ | S | —CH$_2$CH$_3$ | N | CF$_3$ | CH$_3$ | N | CH | N—CH$_3$ | bond |
| 2.256 | N—CH$_2$CH$_3$ | SO$_2$ | —CH$_2$CH$_3$ | N | CF$_3$ | CH$_3$ | N | CH | N—CH$_3$ | bond |
| 2.257 | N—CH$_2$CH$_3$ | S | —CH$_2$CH$_3$ | C—H | CF$_3$ | CH$_3$ | N | C—CH$_3$ | N—CH$_3$ | bond |
| 2.258 | N—CH$_2$CH$_3$ | SO$_2$ | —CH$_2$CH$_3$ | C—H | CF$_3$ | CH$_3$ | N | C—CH$_3$ | N—CH$_3$ | bond |
| 2.259 | N—CH$_2$CH$_3$ | S | —CH$_2$CH$_3$ | N | CF$_3$ | CH$_3$ | N | C—CH$_3$ | N—CH$_3$ | bond |
| 2.260 | N—CH$_2$CH$_3$ | SO$_2$ | —CH$_2$CH$_3$ | N | CF$_3$ | CH$_3$ | N | C—CH$_3$ | N—CH$_3$ | bond |
| 2.261 | N—CH$_2$CH$_3$ | S | —CH$_2$CH$_3$ | C—H | CF$_3$ | CH$_3$ | N | C—CF$_3$ | N—CH$_3$ | bond |
| 2.262 | N—CH$_2$CH$_3$ | SO$_2$ | —CH$_2$CH$_3$ | C—H | CF$_3$ | CH$_3$ | N | C—CF$_3$ | N—CH$_3$ | bond |
| 2.263 | N—CH$_2$CH$_3$ | S | —CH$_2$CH$_3$ | N | CF$_3$ | CH$_3$ | N | C—CF$_3$ | N—CH$_3$ | bond |
| 2.264 | N—CH$_2$CH$_3$ | SO$_2$ | —CH$_2$CH$_3$ | N | CF$_3$ | CH$_3$ | N | C—CF$_3$ | N—CH$_3$ | bond | and the N-oxides and tautomers of the compounds of Table 2.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate.

Examples of the abovementioned animal pests are:
from the order Acarina, for example,

*Acalitus* spp, *Aculus* spp, *Acaricalus* spp, *Aceria* spp, *Acarus siro*, *Amblyomma* spp., *Argas* spp., *Boophi-lus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.; from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *annia* spp. and *Tipula* spp.; from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella*

*singularis, Scaptocoris castanea, Scotino-phara* spp., *Thyanta* spp, *Triatoma* spp., *Vatiga illudens;*

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii Scop., Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp., *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae , Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp, *Slenopsis invicta, Solenopsis* spp. and *Vespa* spp.;

from the order lsoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp., *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusianu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusiani, Tutaabsoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. B. elatior, B. semperflorens, B. tubéreux), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (C. maritime), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (I. Walleriana), (*resines* spp., *Kalanchoe* spp., *Lantana camara, Lavatera trimestris, Leonotis leonurus, Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include *African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia*, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (*Endoparasitic-, Semiendoparasitic-* and *Ectoparasitic nematodes*), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniforrnis* and other *Rotylenchus* species; *Scutellonema* species; Stubby root nematodes, *Trichodorus prim itivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, *Ampullariidae; Arion* (*A. ater, A. circumscriptus, A. hortensis, A. rufus*); *Bradybaenidae* (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); *Helicidae Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from Bacillus cereus or Bacillus popilliae; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cryl-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further Examples of Such Transgenic Crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR$_{604}$ Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S. A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S. A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S. A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603×MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. kurstaki which brings about tolerance to certain *Lepidoptera*, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch). The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above. Crops may also be modified for enhanced resistance to fungal (for example *Fusarium, Anthracnose,* or *Phytophthora*), bacterial (for example *Pseudomonas*) or viral (for example potato leafroll virus, tomato spotted wilt virus, cucumber mosaic virus) pathogens.

Crops also include those that have enhanced resistance to nematodes, such as the soybean cyst nematode.

Crops that are tolerance to abiotic stress include those that have enhanced tolerance to drought, high salt, high temperature, chill, frost, or light radiation, for example through expression of NF-YB or other proteins known in the art.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents. A further object of the invention is therefore a substrate selected from nonwoven and fabric material comprising a composition which contains a compound of formula I.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO 2006/128870, EP 1724392, W02005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, |

TABLE B-continued

Examples of native woodborers of economic importance.

| Family | Species | Host or Crop Infested |
|---|---|---|
| | | Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and S. parvulus), and sod webworms (such as Crambus spp. and the tropical sod webworm, Herpetogramma phaeopteralis).

The present invention may also be used to control insect pests of turfgrass that live above the ground and feed on the turfgrass leaves, including chinch bugs (such as southern chinch bugs, Blissus insularis), Bermudagrass mite (Eriophyes cynodoniensis), rhodesgrass mealybug (Antonina graminis), two-lined spittlebug (Propsapia bicincta), leafhoppers, cutworms (Noctuidae family), and green bugs.

The present invention may also be used to control other pests of turfgrass such as red imported fire ants (Solenopsis invicta) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such Parasites are:

Of the order Anoplurida: Haematopinus spp., Linognathus spp., Pediculus spp. and Phtirus spp., Solenopotes spp.

Of the order Mallophagida: Trimenopon spp., Menopon spp., Trinoton spp., Bovicola spp., Werneckiella spp., Lepikentron spp., Damalina spp., Trichodectes spp. and Felicola spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus spp.*

Of the order Heteropterida, for example *Cimex* spp., *Triatoma* spp., *Rhodnius* spp., *Panstrongylus* spp.

Of the order Blattarida, for example Blatta orientalis, Periplaneta americana, Blattelagermanica and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula spp., Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Lam inosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharine*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents. The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated. The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethyl-hexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances. A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, $10^{th}$ Edition, Southern Illinois University, 2010. The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha. Preferred formulations can have the following compositions (weight %):

Emulsifiable Concentrates:
  active ingredient: 1 to 95%, preferably 60 to 90
  surface-active agent: 1 to 30%, preferably 5 to 20
  liquid carrier: 1 to 80%, preferably 1 to 35%
Dusts:
  active ingredient: 0.1 to 10%, preferably 0.1 to 5%
  solid carrier: 99.9 to 90%, preferably 99.9 to 99%
Suspension Concentrates:
  active ingredient: 5 to 75%, preferably 10 to 50%
  water: 94 to 24%, preferably 88 to 30%
  surface-active agent: 1 to 40%, preferably 2 to 30%
Wettable Powders:
  active ingredient: 0.5 to 90%, preferably 1 to 80%
  surface-active agent: 0.5 to 20%, preferably 1 to 15%
  solid carrier: 5 to 95%, preferably 15 to 90%
Granules:
  active ingredient: 0.1 to 30%, preferably 0.1 to 15%
  solid carrier: 99.5 to 70%, preferably 97 to 85%

The following Examples further illustrate, but do not limit, the invention.

| Wettable powders | a) | b) | c) |
|---|---|---|---|
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The combination is thoroughly mixed with the adjuvants and the mixture is thoroughly ground in a suitable mill, affording powders that can be used directly for seed treatment.

| Emulsifiable concentrate | |
|---|---|
| active ingredients | 10% |
| octylphenol polyethylene glycol ether (4-5 mol of ethylene oxide) | 3% |

Emulsifiable concentrate

| | |
|---|---|
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (E.G.), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

Preparatory Examples:

"Mp" means melting point in ° C. Free radicals represent methyl groups. $^1$H and $^{19}$F NMR measurements were recorded on Brucker 400 MHz or 300 MHz spectrometers, chemical shifts are given in ppm relevant to a TMS standard. Spectra measured in deuterated solvents as indicated.

LCMS Methods:

Method A (SQD13):

Spectra were recorded on a Mass Spectrometer from Waters (SQD Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05%

SYNTHESIS OF INTERMEDIATES

Intermediate 1

Synthesis of 3-ethylsulfanylquinoline-2-carboxylic acid

Step A: ethyl 3-ethylsulfanylquinoline-2-carboxylate

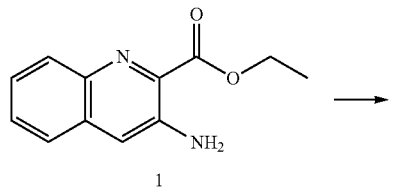

To stirred solution of compound 1 (3.6 g, 16.66 mmol) in DCE (30 ml) was added diethyldisulfide (4.51 ml, 36.6 mmol), t-butyl nitrite was then added dropwise at ambient temperature. The reaction mixture was heated to 40° C. for 2 hours. Reaction was monitored by TLC. After completion of the starting material, reaction mixture was diluted with $CH_2Cl_2$ and washed with water (2×10 mL). Organic layer was dried over $Na_2SO_4$. Filtered, concentrated and purified by column chromatography using hexane-ethyl acetate (100-200 silica gel) to give the desired compound as a yellow liquid (amount: 1.0 g; Yield=23%). $^1H$ NMR (400 MHz, $CDCl_3$): δ (ppm) 8.14 (d, 1H), 8.06 (s, 1H), 7.75 (d, 1H), 7.68 (m, 1H), 7.58 (m, 1H), 4.54 (q, 2H), 3.03 (q, 2H), 1.48 (t, 3H), 1.40 (t, 3H).

Step B: 3-ethylsulfanylquinoline-2-carboxylic acid

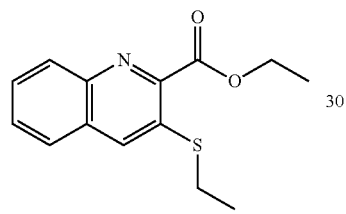

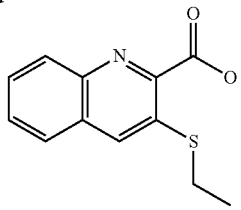

To as stirred solution of compound 3 (1 g, 3.8 mmol) in THF (8 ml) was added NaOH (2 N, 2.2 eq.) at RT. Reaction mixture was stirred for 16 hours at ambient temperature. Reaction was monitored by TLC. After completion of the starting material, reaction mixture was extracted with ethyl acetate (2×10 mL). Water part was then acidified to pH=4 by 10% citric acid solution and extracted with ethyl acetate (3×20 ml). Organic layer was dried over $Na_2SO_4$. Filtered, concentrated under reduced pressure to give the crude solid, which was triturated with ether to give the desired compound as yellow solid (amount: 613 mg; Yield=68%). $^1H$ NMR (400 MHz, DMSO-$d_6$): δ (ppm) 13.7 (s, 1H), 8.42 (s, 1H), 8.00 (m, 2H), 7.75 (m, 1H), 7.68 (m, 1H), 3.09 (q, 2H), 1.29 (t, 3H).

Intermediate 2

Synthesis of 3-ethylsulfanylnaphtalene-2-carboxylic acid

Step A: 3-sulfanylnaphthalene-2-carboxylic acid

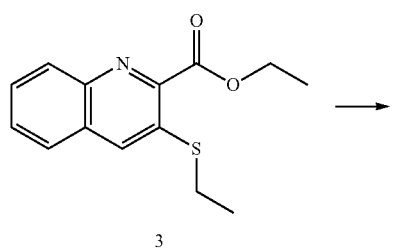

To a stirred suspension of compound-1 (10 g, 53.47 mmol) in water (28 mL) and concentrate HCl (11.4 mL) at 5° C. was added dropwise a solution of $NaNO_2$ (3.69 g, 53.47 mmol) in water (14.6 mL) and the solution maintained at 5° C. Crushed ice was added to the reaction mixture periodically during addition to keep the temperature below 5° C. Meanwhile, $Na_2S·9H_2O$ (13.7 g, 176.47 mmol) and sublimed sulfur (1.88 g, 58.82 mmol) were dissolved in water (15 mL) by heating and made alkaline by addition of NaOH (10 M, 5.5 mL), and the resulting alkaline disulfide solution was cooled to 5° C. in an ice bath. The cold solution was added to the alkaline disulfide solution dropwise with crushed ice added periodically to maintain the temperature below 5° C. Then, the mixture was stirred at room temperature until evolution of $N_2$ gas stopped. Concentrated HCl was added to the solution until precipitation of the crude product as a yellow solid was complete. The precipitate was collected and boiled in a saturated solution of $NaHCO_3$ (130 mL). After being boiled for 15 min, the mixture was filtered to remove the insoluble material, and conc. HCl was added to the filtrate until the crude product precipitated out as a yellow solid. Excess conc. HCl was added to the mixture until precipitation was completed, and the precipitate was isolated by filtration. This material was boiled in absolute EtOH (50 mL) for 15 min and filtered and the filtrate concentrated under reduced pressure to yield the dithiosalicylic acid derivative The dithiosalicylic acid derivative was then mixed with Zn dust(3.2 g) in glacial CH₃COOH (50 mL) and refluxed for 48 hours. The mixture was then cooled and filtered. The solid collected in this manner was boiled in 5 M NaOH (100 mL). After being boiled for 30 min, the solid was removed by filtration and the clear filtrate acidified with concentrated HCl until the crude product precipitated out as a yellow solid. Concentrated HCl was added to the mixture until the precipitation was complete. The precipitate was collected and boiled in EtOH (40 mL) and filtered and the filtrate concentrated under reduced pressure to yield the thiosalicylic acid derivative 2. This material was directly carried on to the next step without extra purification (amount: 4 g; Yield=36%).

Step B: 3-ethylsulfanylnaphtalene-2-carboxylic acid

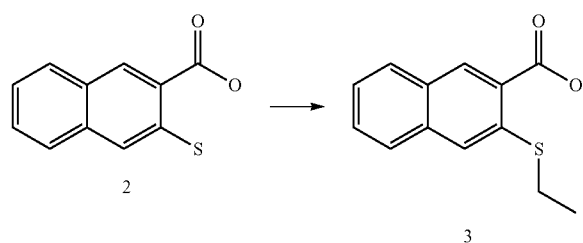 [SMILES: O=C(O)c1cc2ccccc2cc1S ; CCSc1cc2ccccc2cc1C(=O)O]

To a stirred solution of compound 2 (1.9 g, 9.36) in ethanol (10 ml) and NaOH (1M, 10 mL) was added EtI (0.75 ml, 9.36 mmol) at ambient temperature. The reaction mixture was stirred for 48 hours. LC-MS showed desired product was formed. Solvent was evaporated and the crude was acidified to pH=2, extracted with ethyl acetate (2×30 ml). Ethyl acetate layer was dried over Na₂SO₄. Filtered, concentrated and purified by column chromatography using hexane-ethyl acetate (100-200 silica gel) to give the desired compound as a yellow solid. Yield=amount: 274 mg; 25%. ¹H NMR (400 MHz, DMSO-d₆): δ (ppm) 13.14(s, 1H), 8.49 (s, 1H), 7.99 (d, 1H), 7.90 (d, 1H), 7.81 (s, 1H), 7.62 (t, 1H), 7.48 (t, 1H), 3.04 (q, 2 H), 1.32 (t, 3H).

Intermediate 3

4-amino-1-methyl-3-(methylamino)-6-(trifluoromethyl)pyridin-2-one

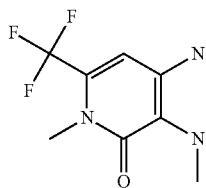

Step A: 1-methyl-3-(methylamino)-6-(trifluoromethyl)pyridin-2-one

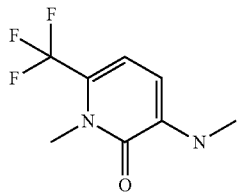

To a solution of 3-amino-1-methyl-6-(trifluoromethyl)pyridin-2-one (1.00 g, 5.20 mmol, Commercially available or synthesised as described for example in Synthesis 2005, No. 8, pp 1269-1278, Synthesis 2011, No. 7, pp 1149-1156) in 1,4-dioxane (62.5 mL, 726 mmol) and pyridine (1.49 mL, 18.2 mmol), under argon, was added diacetoxycopper (2.39 g, 13.0 mmol). The mixture was stirred for 15 min before addition of methylboronic acid (0.803 g, 13.0 mmol). The resulting green/blue suspension was refluxed for 5 hours. After cooling, the solution was filtered through a Celite pad. The dark green solution was concentrated under vacuum and was subjected to column chromatography over silica gel, eluting with ethyl acetate/cyclohexane. The selected fractions were evaporated to yield the title compound (0.71 g).
¹H NMR (400 MHz, CDCl₃) δ ppm 7.27 (s, 1 H); 6.72 (d, 1 H); 6.04 (d, 2 H), 5.46 (bs, 1 H), 3.68 (s, 3H), 2.88 (d, 3H).

Step B: 1-methyl-3-(methylamino)-4-nitro-6-(trifluoromethyl)pyridin-2-one

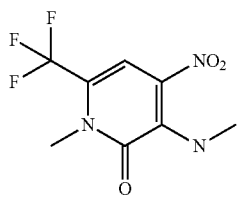 [SMILES: CNc1c([N+](=O)[O-])cc(C(F)(F)F)n(C)c1=O]

A solution of 1-methyl-3-(methylamino)-6-(trifluoromethyl)pyridin-2-one (4.00 g, 19.4 mmol) sulfuric acid (58.2 mL) was cooled with an ice bath at 0° C. Then, Ice (20.0 g) and nitric acid (1.88 g, 1.35 mL, 19.4 mmol) were added. After 15 min at 0-10° C., the brown thick solution was poured into iced water. The orange precipitate form was filtrated off, rinsing with water and drying under vacuum to give an orange solid. The water phase was extracted 3 times with AcOEt and the orange solid, obtained before, was added to the combinated organic phase. The combinated organic phase was washed with a saturated solution of sodium hydrogenocarbonate, water and brine, dried over magnesium sulfate and concentrated under vacuum to give yield the title compound (4.0 g). The compound was used without extra purification for the next step. LC-MS(Method A): RT 0.91, 252 (M+H⁺), 250 (M−H⁺).

Step C: 4-amino-1-methyl-3-(methylamino)-6-(trifluoromethyl)pyridin-2-one

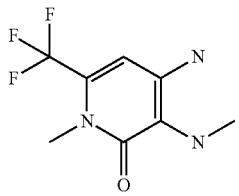

To a solution of 1-methyl-3-(methylamino)-4-nitro-6-(trifluoromethyl)pyridin-2-one (3.0 g, 11.9 mmol) in propan-2-ol (98.1 g, 125 mL, 1620 mmol) was added tin(II) chloride dihydrate (8.24 g, 43.0 mmol) followed by hydrogen chloride (10 mL, 120 mmol, 37%) . The resulting solution was stirred at 70° C. for one hour, and, then allowed to cool down to ambient temperature. The reaction mixture was poured into water, and pH was adjusted to 10-12 with a concentrated solution of sodium hydroxide (30%). The aqueous phase was extracted three times with ethyl acetate, the organic phases were combinated, dried over magnesium sulfate and concentrated under vacuum. subjected to column chromatography over silica gel, eluting with ethyl acetate/cyclohexane. The selected fractions were evaporated to yield the title compound (2.15 g). $^1$H NMR (400 MHz, CDCl$_3$) δ ppm 6.30 (s, 1 H); 4.15 (bs, 2 H), 3.8 (bs, 1 H), 3.60 (s, 3H), 2.64 (s, 3H).

Intermediate 4

4-amino-1-ethyl-3-(methylamino)-6-(trifluoromethyl)pyridin-2-one

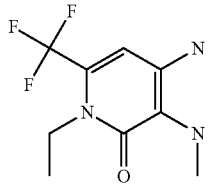

Step A: 1-ethyl-3-(methylamino)-6-(trifluoromethyl)pyridin-2-one

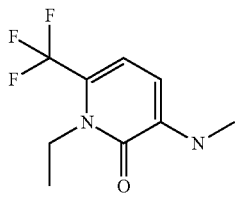

To a solution of 3-amino-1-ethyl-6-(trifluoromethyl)pyridin-2-one (5.00 g, 24.3 mmol, Commercially available or synthesised by analogy with literature, for example, Synthesis 2005, No. 8, pp 1269-1278 and Synthesis 2011, No. 7, pp 1149-1156) in acetonitrile (150 mL) was added formaldehyde (37 mass %) in aq. solution (14.5 ml, 194 mmol) and acetic acid (6.96 ml, 121 mmol). The resulting suspension stirred for 1 hour, then sodium cyanoborohydride (6.42 g, 97.0 mmol) was added in 5 portions over 3 hours and the mixture was stirred overnight. The solution was diluted with water and extracted with ethyl acetate (3×). The combined organic layer was dried over Na$_2$SO$_4$, filtered, concentrated and purified by column chromatography using cyclohexane-ethyl acetate (100-200 silica gel) to give the desired compound as a white solid. $^1$H NMR (400 MHz, CDCl$_3$) δ ppm 6.70 (d, 1 H), 6.04 (d, 1 H), 5.44 (sb, 1 H), 4.15 (q, 2H), 2.85 (s, 3H), 1.32 (t, 3H).

Step B: 1-ethyl-3-(methylamino)-4-nitro-6-(trifluoromethyl)pyridin-2-one

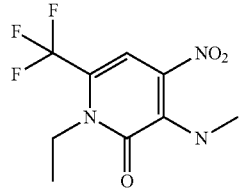 [SMILES: CCn1c(C(F)(F)F)cc([N+](=O)[O-])c(NC)c1=O]

The 1-ethyl-3-(methylamino)-4-nitro-6-(trifluoromethyl)pyridin-2-one was prepared as for Example 3, step B. LC-MS(Method A): RT 0.98, 266 (M+H$^+$), 264 (M–H$^+$).

Step C: 4-amino-1-ethyl-3-(methylamino)-6-(trifluoromethyl)pyridin-2-one

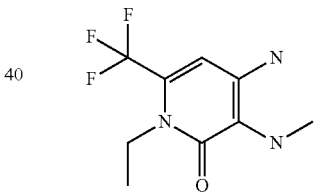

The 4-amino-1-ethyl-3-(methylamino)-6-(trifluoromethyl)pyridin-2-one was prepared as for Example 3, step C. LC-MS(Method A): RT 0.47, 236 (M+H$^+$).

Intermediate 5

6-ethylsulfonyl-1-methyl-2-(trifluoromethyl)benzimidazole-5-carboxylic acid

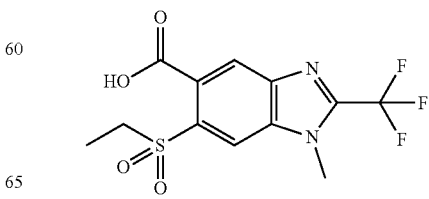

Step A: Synthesis of 4-chloro-2-ethylsulfanyl-5-nitro-benzoic acid

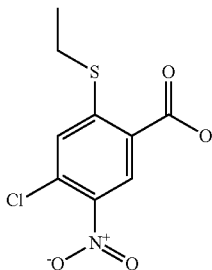

To a solution of 4-chloro-2-fluoro-5-nitro-benzoic acid (20 g, 91.095 mmol, commercially available) in 1-Methyl-2-pyrrolidone (250 mL) at 90° C. was added sodium t-butoxide (9.6302 g, 100.20 mmol). After 10min ethylsulfanyl-sodium (9.366 g, 100.20 mmol) was added.

The reaction was stirred at 90° C. for two hours. The conversion is complete, two products were formed. The reaction mixture was poured into one liter of water and pH was acidified by addition of hydrochloride acid conc. (37%) and precipitate was formed. Filtration of the solid gave the mixture of two products. Filtrate was allowed to stand. The solid was suspended in ethyl ether and filtered. The solid (pure) was identified as the bis-ethylsulfanyl product. The filtrate was concentration under vacuum to give 4-chloro-2-ethylsulfanyl-5-nitro-benzoic acid (8.9 g, 34 mmol, 37% Yield). LC-MS (Method A): RT 1.00 (260, MH$^-$) (262, MH$^+$).

$^1$H NMR (300 MHz, CDCl$_3$) ppm 13.84 (s, 1H) 8.52 (s, 1 H); 7.6 (s, 1 H); 3.09 (q, 2 H); 1.3 (t, 3H).

Step B: Synthesis of 2-ethylsulfanyl-4-(methylamino)-5-nitro-benzoic acid

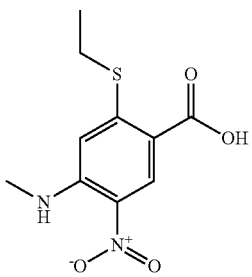

To a solution of 4-chloro-2-ethylsulfanyl-5-nitro-benzoic acid (8.9 g, 34 mmol) in tetrahydrofuran (20 mL, 244 mmol) was added gently methylamine (2 mol/L) in tetrahydrofuran (100 mL, 200 mmol). The mixture was stirred overnight at ambient temperature. Only a few conversions were observed. The suspension was transferred in an autoclave, 30 mL of methylamine 2N was added, and the reaction was stirred at 80° C. for five hours. The reaction is not complete and 20mL more of 2N methylamine was added then the reaction was stirred in an autoclave over week end. Reaction is finished, and reaction mixture was concentrated under vacuum. Solids were taken up in water and basified with sodium hydroxide 1 N, then extracted with ethyl acetate. The water phase was acidified with hydrochloride acid conc. 37% and extracted with ethyl acetate. All organic layers are combined and were dried on magnesium sulfate, and concentrated on vacuum. The residue was then purified by Flash Chromatography to give 2-ethylsulfanyl-4-(methylamino)-5-nitro-benzoic acid (3.95 g, 15.4 mmol, 45% Yield) as a yellow-brownish solid. LC-MS (Method A): RT 1.04 (257, MH$^+$). $^1$H NMR (300 MHz, CDCl$_3$) ppm 12.87 (s, 1H) 8.68 (s, 1 H); 6.55 (s, 1 H); 3.05 (s, 3 H); 3.00 (q, 2H) 1.33 (t, 3H).

Step C: Synthesis of 6-ethylsulfanyl-1-methyl-2-(trifluoromethyl)benzimidazole-5-carboxylic acid

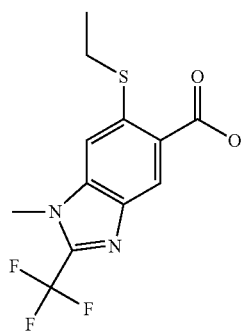 [SMILES: CCSc1cc2c(cc1C(=O)O)nc(C(F)(F)F)n2C]

To a solution of 2-ethylsulfanyl-4-(methylamino)-5-nitro-benzoic acid (0.300 g, 1.17 mmol) in 2,2,2-trifluoroacetic acid (10 mL,129 mmol) at 0° C., zinc (0.260 g, 3.98 mmol) was added and cooling bath was removed. After 30 min, reduction is complete according to LC/MS; a few cyclized product was observed. The brown solution was then heated at 70° C. to cyclize the di-amino product. After one hour LC/MS showed completion of the cyclisation. Reaction mixture was concentrated to the half, poured into water and extracted with ethyl acetate. Organic phase was washed with water and brine, dried over magnesium sulfate and concentrated under vacuum.

Residue was purified by flash chromatography to give 6-ethylsulfanyl-1-methyl-2-(trifluoromethyl)benzimidazole-5-carboxylic acid (0.14 g, 0.46 mmol,39.3% Yield).

LC-MS (Method A): RT 1.06 (303, MH$^-$) (305, MH$^+$). $^1$H NMR (300 MHz, CDCl$_3$) ppm 13.03 (s, 1H) 8.30 (s, 1 H); 7.64 (s, 1 H); 4.00 (s, 3 H); 3.06 (q, 2H) 1.32 (t, 3H).

Intermediate 6

7-ethylsulfanylisoquinoline-6-carboxylic acid

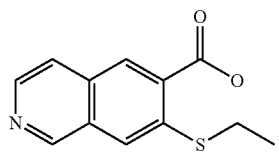 [SMILES: CCSc1cc2cnccc2cc1C(=O)O]

Step A: Synthesis of 7-fluoroisoquinoline-6-carbonitrile

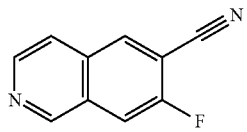 [SMILES: N#Cc1cc2ccncc2cc1F]

Under argon to a solution of 6-bromo-7-fluoroisoquinoline [1258833-80-5] (228.33 mg, 1 mmol) in N,N-Dimethylformamide (5 ml), was added copper cyanide (134.34 mg, 1 mmol). The mixture was heated to 100° C. After 24 h, the reaction was filtered through Celite, washed with ethyl acetate. The organic layer was washed with brine, dried and concentrated. The crude product was purified by flash chromatography to give 7-fluoroisoquinoline-6-carbonitrile (13 mg, 7.5%) as a pale brown solid.
$^1$H NMR (400 MHz, CDCl$_3$) ppm 9.33 (s, 1 H); 8.68 (d, 1 H); 8.27 (d, 1 H); 7.76 (d, 1 H); 7.72 (d, 1H). Mp: 157-158° C.

Step B: Synthesis of methyl 7-fluoroisoquinoline-6-carboxylate

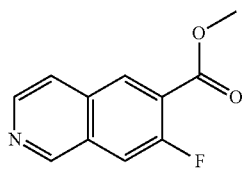

In an autoclave, 6-bromo-7-fluoroisoquinoline [1258833-80-5] (452.1 mg, 2 mmol), Bis(triphenylphoshine)palladuim dichloride (71 mg, 0.1 mmol) and triethylamine (404.7 mg, 2 mmol) were added to methanol (40 ml).Then, the inner atmosphere of autoclave was replaced by carbon monoxide, and the pressure in the vessel was 20 bar, heated to about 80° C. and stirred for 15 h. The solvent was evaporated, residue dissolved in ethyl acetate, washed with brine, dried and concentrated. The residue was purified by flash chromatography to give methyl 7-fluoroisoquinoline-6-carboxylate (314 mg, 76.5%) as a white solid. $^1$H NMR (400 MHz, CDCl$_3$) ppm 9.27(s, 1 H); 8.60 (d, 1 H); 8.50 (d, 1 H); 7.73 (d, 1 H); 7.68 (d, 1H); 4.02 (s, 3H). Mp: 89-90° C.

Step C: Synthesis of methyl 7-ethylsulfanylisoquinoline-6-carboxylate

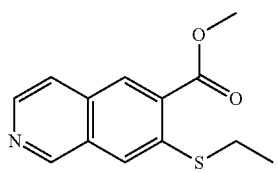 [SMILES: CCSc1cc2cnccc2cc1C(=O)OC]

The mixture of methyl 7-fluoroisoquinoline-6-carboxylate (324 mg, 1.58 mmol), sodium thioethoxide (1.62 mg, 1.58 mmol) and N,N-Dimethylformamide (3 ml) was stirred at room temperature for overnight. The solvent was evaporated by toluene, residue dissolved in ethyl acetate and washed with water, dried and evaporated. The crude product was purified by flash chromatography to give methyl 7-ethylsulfanylisoquinoline-6-carboxylate (235 mg, 60%) as a pale yellow solid.
$^1$H NMR (400 MHz, CDCl$_3$) ppm 9.21(s, 1 H); 8.52 (d, 1 H); 8,42(s, 1 H); 7.76(s, 1 H); 7.64 (d, 1H); 4.00 (s, t); 3.10 (q.,2H); 1.46 (t, 3H). Mp: 85-86° C.

Step D: Synthesis of 7-ethylsulfanylisoquinoline-6-carboxylic acid

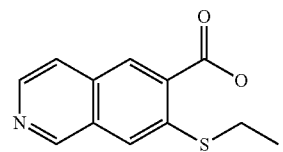 [SMILES: CCSc1cc2cnccc2cc1C(=O)O]

Methyl 7-ethylsulfanylisoquinoline-6-carboxylate (1.1 g, 4.51 mmol) was stirred in a mixture of sodium hydroxide (225 mg, 4.51 mmol) water (2 ml) and methanol (20 ml) at room temperature for overnight. Methanol in the reaction solution was distilled off and the residue was washed with ethyl acetate .The aqueous layer was acidified with diluted hydrochloric acid (pH 4-5). The yellow precipitate was filtered off and dried. $^1$H NMR (400 MHz, CDCl$_3$) ppm9.69 (s, 1 H); 8.68 (d, 1 H); 8.61 (d, 1 H); 8.36(2d, 2 H); 3.13 (q.,2H); 1.37 (t, 3H).

Example P1

Preparation 5-ethyl-2-(3-ethylsulfanyl-2-naphthyl)-3-methyl-6-(trifluoromethyl)-3aH-imidazo[4,5-c]pyrid in-4-one (A1, 2.133)

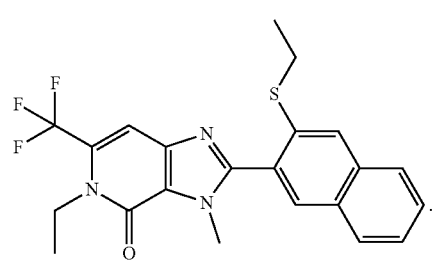

A1(2.133)

Step A: Preparation of N-[1-ethyl-3-(methylamino)-2-oxo-6-(trifluoromethyl)-3H-pyridin-4-yl]-3-ethyl-sulfanyl-naphthalene-2-carboxamide and N-[4-amino-1-ethyl-2-oxo-6-(trifluoromethyl)-3-pyridyl]-3-ethylsulfanyl-N-methyl-naphthalene-2-carboxamide

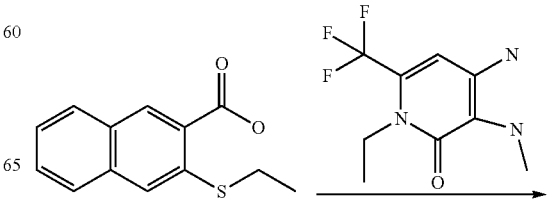

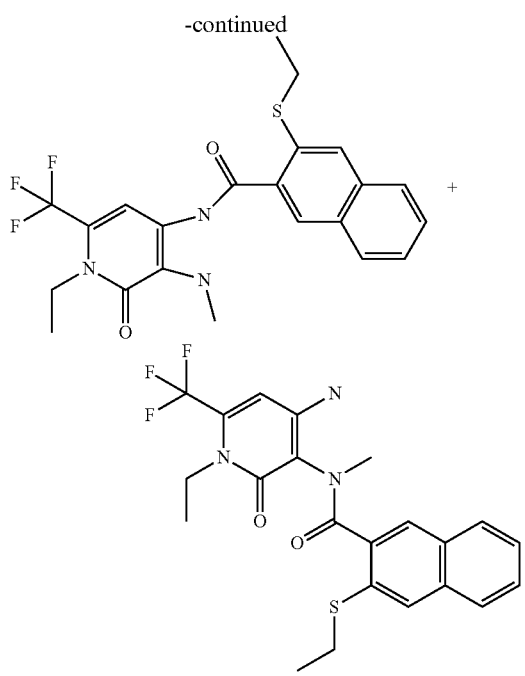

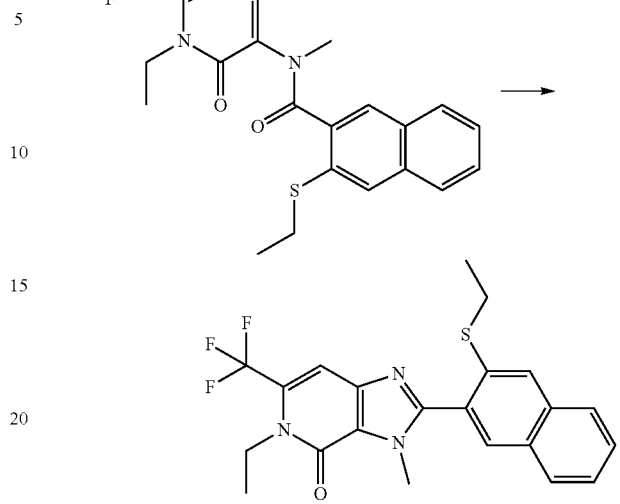

3-ethylsulfanylnaphthalene-2-carboxylic acid (132 mg, 0.570 mmol) was dissolved in dichloromethane (1.14 mL) and was added of oxalyl dichloride (0.101 mL, 1.14 mmol) and N,N-dimethylformamide (1 drop). The mixture was stirred for 30 min at ambient temperature then at reflux for 30 min. The solvent was removed and dried by vacuum.

The 3-ethylsulfanylnaphthalene-2-carbonyl chloride (143.0 mg, 0.571 mmol) was diluted with 0.5 ml of THF and added at a mixture of 4-amino-1-ethyl-3-(methylamino)-6-(trifluoromethyl)pyridin-2-one (Prepared in example 4, 122 mg, 0.51869 mmol) in tetrahydrofuran (1.0 mL) and pyridine (0.13 mL, 1.55 mmol). The mixture was stirred at reflux for 3 hours. The solution was diluted with a saturated solution of sodium carbonate and ethyl acetate. The aqueous phase was extracted with ethyl acetate (2×). The combined organic layer was dried over Na$_2$SO$_4$, filtered, concentrated and purified by column chromatography using cyclohexane-ethyl acetate to give the desired compounds (180 mg). The mixture was used without extra purification for the next step. LC-MS(Method A): RT 0.99, 450 (M+H$^+$).

Step B: Preparation 5-ethyl-2-(3-ethylsulfanyl-2-naphthyl)-3-methyl-6-(trifluoromethyl)-3aH-imidazo[4,5-c]pyridin-4-one (A1, 2.133)

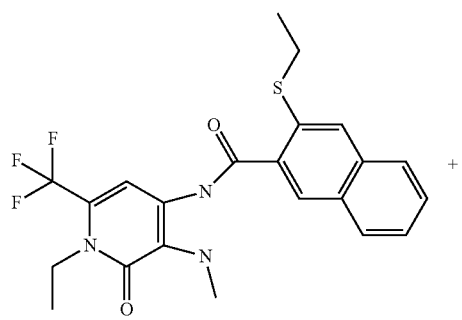

A microwave vial was charged with a mixture of N-[1-ethyl-3-(methylamino)-2-oxo-6-(trifluoromethyl)-3H-pyridin-4-yl]-3-ethylsulfanyl-naphthalene-2-carboxamide and N-[4-amino-1-ethyl-2-oxo-6-(trifluoromethyl)-3-pyridyl]-3-ethylsulfanyl-N-methyl-naphthalene-2-carboxamide (0.18 g, 0.4004 mmol) acetic acid (2.0 mL). Then, the mixture was stirred for 2 h20 at 150° C. under microwaves. The reaction mixture was diluted with water (10 mL) and extracted two time with ethyl acetate. The combined organic phases were washed with water and dried over sodium sulfate and concentrated under vacuum. The residue was subjected to column chromatography, eluting with ethyl acetate/cyclohexane. The selected fractions were evaporated to yield the title compound (135 mg). LC-MS(Method A): RT 1.19, 433 (M+H$^+$).

Example P2

Preparation of 5-ethyl-2-(3-ethylsulfonyl-2-naphthyl)-3-methyl-6-(trifluoromethyl)-6H-imidazo[4,5-c]pyridin-4-one (A2, 2.134)

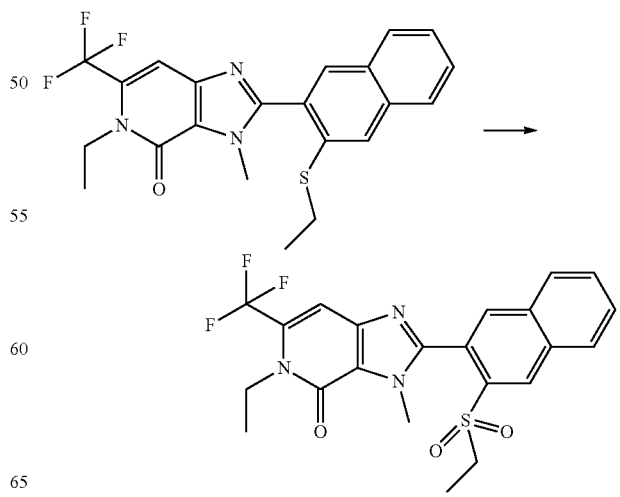

To a stirred solution of compound A1 (125 mg, 0.2897 mmol) in CH$_2$Cl$_2$ (5.7 ml) was added m-CPBA (171.4 mg, 0.6952 mmol) at ambient temperature. The reaction mixture was then stirred for 2 hours. Reaction was monitored by TLC. After completion of the starting, the reaction mixture was quenched with saturated Na$_2$S$_2$O$_3$, NaHCO$_3$ and extracted with CH$_2$Cl$_2$ (10×2 mL). CH$_2$Cl$_2$ layer was dried over Na$_2$SO$_4$. Filtered, concentrated and purified by column chromatography using cyclohexane-ethyl acetate (100-200 silica gel) to give the desired compound as a white solid (130 mg). LC-MS(Method A) : RT 1.05, 464 (M+H$^+$).

Example P3

Preparation of 5-ethyl-2-(3-ethylsulfanyl-2-quinolyl)-3-methyl-6-(trifluoromethyl)-3aH-imidazo[4,5-c]pyrid in-4-one (A3, 2.139)

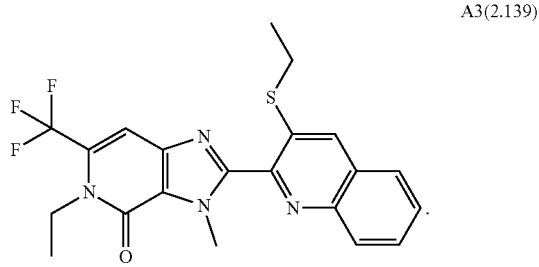 [SMILES: CCSc1cc2ccccc2nc1-c1nc2cc(C(F)(F)F)n(CC)c(=O)c2n1C]

A3(2.139)

Step A: The preparation of N-[1-ethyl-3-(methylamino)-2-oxo-6-(trifluoromethyl)-3H-pyridin-4-yl]-3-ethylsulfanyl-quinoline-2-carboxamide and N-[4-amino-1-ethyl-2-oxo-6-(trifluoromethyl)-3-pyridyl]-3-ethylsulfanyl-N-methyl-quinoline-2-carboxamide was done using the same protocol that described in Example P1, Step A for A1. LC-MS(Method A): RT 0.94, 451 (M+H$^+$), 449 (M−H$^+$).

Step B: The preparation of 5-ethyl-2-(3-ethylsulfanyl-2-quinolyl)-3-methyl-6-(trifluoromethyl)-3aH-imidazo[4,5-c]pyridin-4-one (A3, 2.139) was done using the same protocol that described in Example P1, Step B for A1. LC-MS (Method A): RT 1.14, 433 (M+H$^+$).

Example P4

Preparation of 5-ethyl-2-(3-ethylsulfonyl-2-quinolyl)-3-methyl-6-(trifluoromethyl)-6H-imidazo[4,5-c]pyridin-4-one (A4, 2.140)

A4

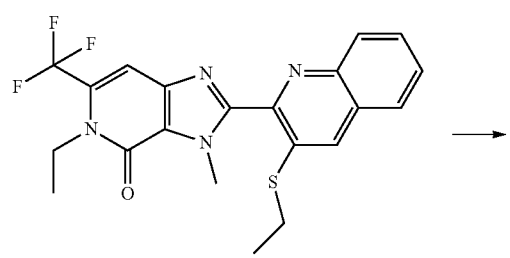

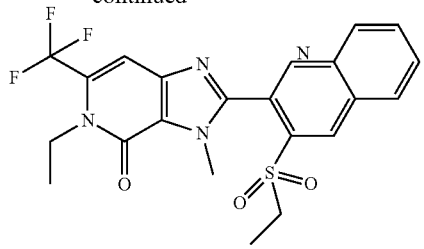

The 5-ethyl-2-(3-ethylsulfonyl-2-quinolyl)-3-methyl-6-(trifluoromethyl)-6H-imidazo[4,5-c]pyridin-4-one A4 was synthesized as for A2 in example P2. LC-MS (Method A): RT 1.06, 465 (M+H$^+$).

Example P5

Preparation of 5-ethyl-2-[6-ethylsulfanyl-1-methyl-2-(trifluoromethyl)benzimidazol-5-yl]-3-methyl-6-(trifluoromethyl)imidazo[4,5-c]pyridin-4-one (A5, 2.141)

A5

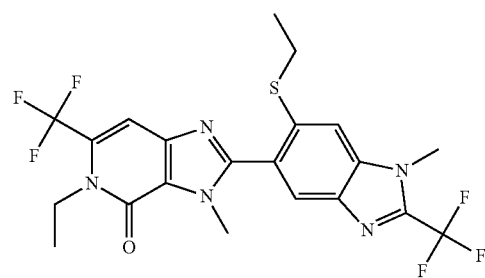

Step A: Preparation of N-[1-ethyl-3-(methylamino)-2-oxo-6-(trifluoromethyl)-4-pyridyl]-6-ethylsulfanyl-1-methyl-2-(trifluoromethyl)benzimidazole-5-carboxamide and N-[4-amino-1-ethyl-2-oxo-6-(trifluoromethyl)-3-pyridyl]-6-ethylsulfanyl-N,1-d imethyl-2-(trifluoromethyl)benzim idazole-5-carboxam ide

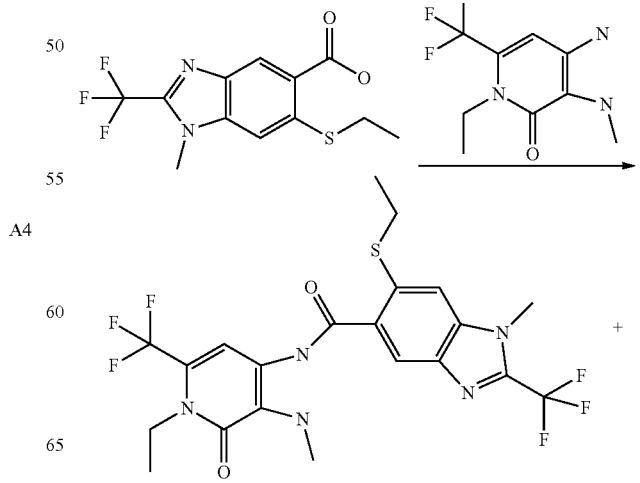

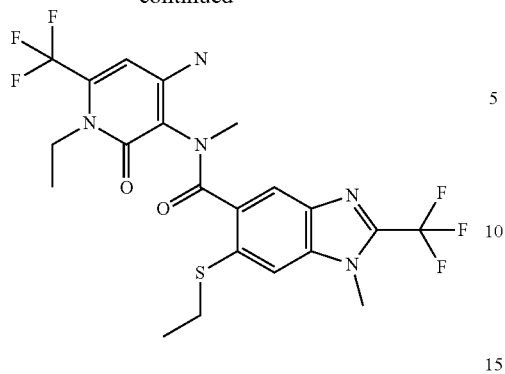

6-ethylsulfanyl-1-methyl-2-(trifluoromethyl)benzimidazole-5-carboxylic acid (162 mg, 0.533 mmol) was dissolved in dichloromethane (5 mL) and was added of oxalyl dichloride (0.083 mL, 0.941 mmol) and N,N-dimethylformamide (1 drop). The mixture was stirred for 30 min at ambient temperature then at reflux for 30 min. The solvent was removed and dried by vacuum.

The 3-ethylsulfanylnaphthalene-2-carbonyl chloride was diluted with 3 ml of THF and added at a mixture of 4-amino-1-ethyl-3-(methylamino)-6-(trifluoromethyl)pyridin-2-one (Prepared in example 4, 123 mg, 0.523 mmol) in tetrahydrofuran (5.0 mL) and N,N-diethylethanamine (0.184 mL, 1.31 mmol). The mixture was stirred at room temperature for 1 hour. The solution was diluted with a saturated solution of sodium carbonate and ethyl acetate. The aqueous phase was extracted with ethyl acetate (2×). The combined organic layer was dried over $Na_2SO_4$, filtered, concentrated and purified by column chromatography using cyclohexane-ethyl acetate to give the desired compounds (273 mg). The mixture was used without extra purification for the next step. LC-MS(Method A): RT 0.94, 520 (M–H$^+$) 522 (M+H$^+$).

Step B: Preparation 5-ethyl-2-(3-ethylsulfanyl-2-naphthyl)-3-methyl-6-(trifluoromethyl)-3aH-imidazo[4,5-c]pyridin-4-one (A5, 2.141)

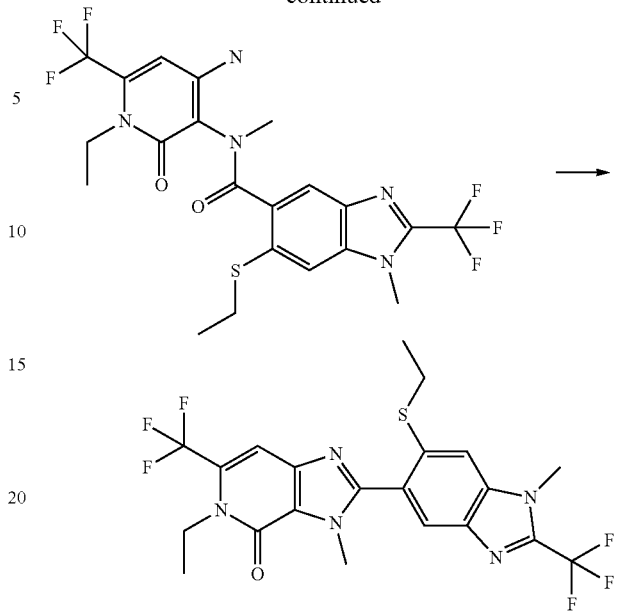

A microwave vial was charged with a mixture of N-[1-ethyl-3-(methylamino)-2-oxo-6-(trifluoromethyl)-4-pyridyl]-6-ethylsulfanyl-1-methyl-2-(trifluoromethyl)benzimidazole-5-carboxamide and N-[4-amino-1-ethyl-2-oxo-6-(trifluoromethyl)-3-pyridyl]-6-ethylsulfanyl-N,1-dimethyl-2-(trifluoromethyl)benzimidazole-5-carboxamide (0.273 g, 0.523 mmol) acetic acid (4.0 mL). Then, the mixture was stirred for 1 h at 150° C. under microwaves. The reaction mixture was diluted with water (10 mL) and extracted two time with ethyl acetate. The combined organic phases were washed with water and dried over sodium sulfate and concentrated under vacuum. The residue was subjected to column chromatography, eluting with ethyl acetate/cyclohexane. The selected fractions were evaporated to yield the title compound (164 mg). LC-MS (Method A): RT 1.13, 505 (M+H$^+$). $^1$H NMR (400 MHz, CDCl$_3$) δ ppm 1.25 (t, 3 H), 1.40 (t, 3 H), 2.89 (q, 2 H), 3.93 (s, 3 H), 4.01 (s, 3 H), 4.26 (q, 2 H), 7.30 (s, 1 H), 7.53 (s, 1 H), 7.89 (s, 1 H).

Example P6

Preparation of 5-ethyl-2-[6-ethylsulfonyl-1-methyl-2-(trifluoromethyl)benzimidazol-5-yl]-3-methyl-6-(trifluoromethyl)imidazo[4,5-c]pyridin-4-one (A6, 2.142)

A5

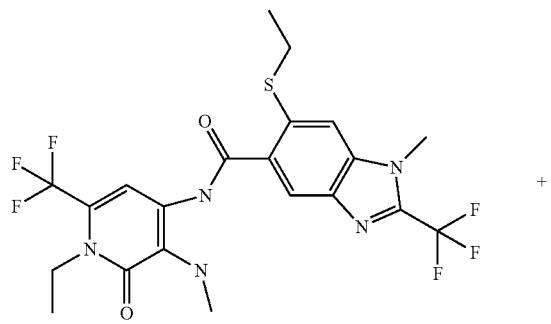

+

A6

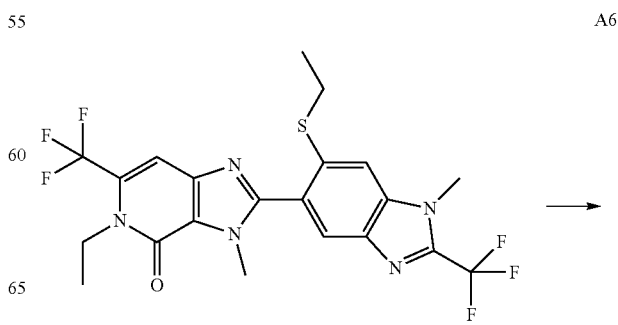

-continued

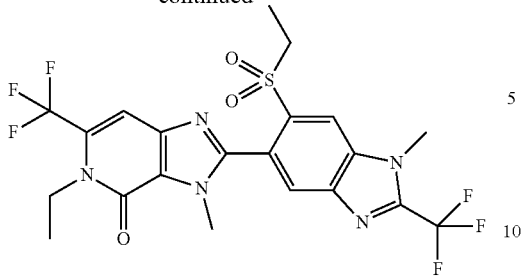

To a stirred solution of compound A5 (158 mg, 0.313 mmol) in CH$_2$Cl$_2$ (15 ml) was added m-CPBA (158 mg, 0.690 mmol) at ambient temperature. The reaction mixture was then stirred for overnight. Reaction was monitored by TLC. After completion of the starting, the reaction mixture was quenched with saturated Na$_2$S$_2$O$_3$, NaHCO$_3$ and extracted with CH$_2$Cl$_2$ (10×2 mL). CH$_2$Cl$_2$ layer was dried over Na$_2$SO$_4$. Filtered, concentrated and purified by column chromatography using cyclohexane-ethyl acetate (100-200 silica gel) to give the desired compound as a white solid (168 mg). LC-MS(Method A): RT 1.05, 537 (M+H$^+$).

$^1$H NMR (400 MHz, CDCl$_3$) δ ppm 1.27 (t, 3 H), 1.41 (t, 3 H), 3.55 (m, 2 H), 3.90 (s, 3 H), 4.14 (s, 3 H), 4.25 (q, 2 H), 7.22 (s, 1 H), 7.98 (s, 1 H), 8.41 (s, 1 H).

Example P7

Synthesis of N-[1-ethyl-3-(methylamino)-2-oxo-6-(trifluoromethyl)-4-pyridyl]-7-ethylsulfanyl-isoquinoline-6-carboxamide and N-[4-amino-1-ethyl-2-oxo-6-(trifluoromethyl)-3-pyridyl]-7-ethylsulfanyl-N-methyl-isoquinoline-6-carboxamide

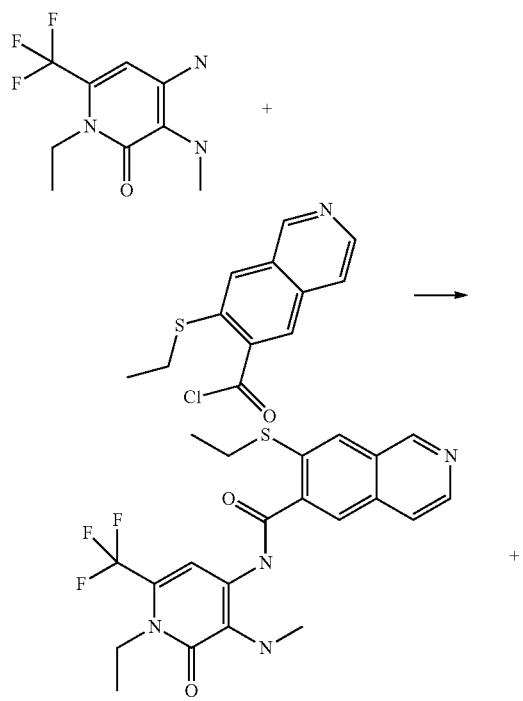

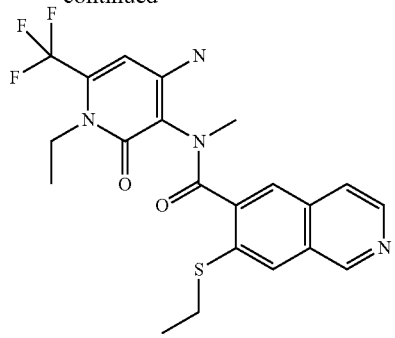

7-ethylsulfanylisoquinoline-6-carboxylic acid (109 mg, 0.467 mmol) is dissolved in dichloromethane (0.934 mL) with oxalyl chloride (121 mg, 0.0831 mL, 0.934 mmol) and N,N-dimethylformamide (1 drop). The mixture was stirred for 30 min at room temperature then at reflux for 30 min. Then the solvent was removed and dried by vacuum. The 7-ethylsulfanylisoquinoline-6-carbonyl chloride (118 mg, 0.467 mmol) was diluted with 0.5 ml of tetrahydrofuran and added at a solution of 4-amino-1-ethyl-3-(methylamino)-6-(trifluoromethyl)pyridin-2-one [1643139-91-6] (100 mg, 0.42515 mmol) in tetrahydrofuran (0.85 mL) and pyridine (0.10 mL). The mixture was stirred at reflux for 3 hours and stopped. Ethyl acetate and water were added; organic phase was collected, dried on magnesium sulfate and concentrated on vacuum. The residue was purified by flash chromatography to give a mixture of N-[1-ethyl-3-(methylamino)-2-oxo-6-(trifluoromethyl)-4-pyridyl]-7-ethylsulfanyl-isoquinoline-6-carboxamide and N-[4-amino-1-ethyl-2-oxo-6-(trifluoromethyl)-3-pyridyl]-7-ethylsulfanyl-N-methyl-isoquinoline-6-carboxamide. LC-MS (Method A) RT=0.75 min, m/z=449 [M−1], 451 [M+1].

Step A: Synthesis of 5-ethyl-2-(7-ethylsulfanyl-6-isoquinolyl)-3-methyl-6-(trifluoromethyl)imidazo[4,5-c]pyridin-4-one (A7)

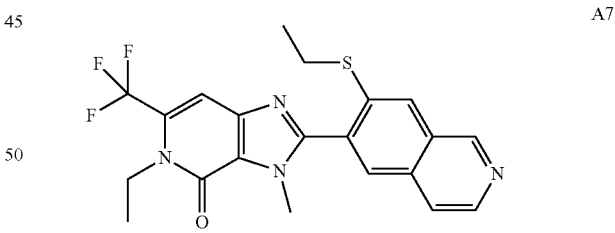

In MW vial, a mixture of N-[1-ethyl-3-(methylamino)-2-oxo-6-(trifluoromethyl)-4-pyridyl]-7-ethylsulfanyl-isoquinoline-6-carboxamide and N-[4-amino-1-ethyl-2-oxo-6-(trifluoromethyl)-3-pyridyl]-7-ethylsulfanyl-N-methyl-isoquinoline-6-carboxamide (0.1 g, 0.22 mmol) was solved in acetic acid (1.1 mL) and vial was stirred 30 min at 150° C. in the microwave system, to complete the reaction, vial was stirred 30 min more at 150° C. Water (10 mL)/ethyl acetate were added and organic phase was dried on Magnesium sulfate, and then concentrated. The residue was purified by flash chromatography to give 5-ethyl-2-(7-ethylsulfanyl-6-isoquinolyl)-3-methyl-6-(trifluoromethyl)imidazo[4,5-c]pyridin-4-one (A7).

$^1$H NMR (400 MHz, CDCl$_3$) δ ppm 1.34 (t, 3 H), 1.41 (t, 3 H), 3.03 (q, 2 H), 4.00 (s, 3 H), 4.27 (q, 2H), 7.30 (s, 1 H), 7.66 (d, 1 H), 7.90 (d, 2 H), 8.58 (d, 1 H), 9.29 (s, 1 H).

Step B: Synthesis of 5-ethyl-2-(7-ethylsulfonyl-6-isoquinolyl)-3-methyl-6-(trifluoromethyl)imidazo[4,5-c]pyridin-4-one (A8) and 5-ethyl-2-(7-ethylsulfonyl-2-oxido-isoquinolin-2-ium-6-yl)-3-methyl-6-(trifluoromethyl)imidazo[4,5-c]pyridin-4-one (A9)

A8

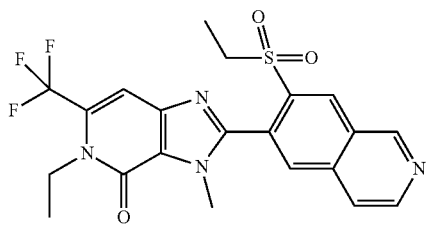

A9

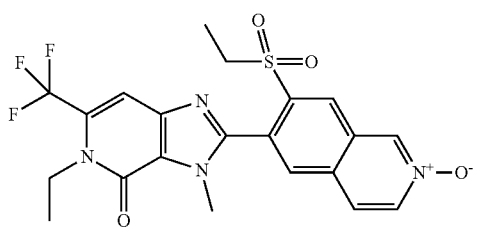

At 0° C., to a solution of 5-ethyl-2-(7-ethylsulfanyl-6-isoquinolyl)-3-methyl-6-(trifluoromethyl)imidazo[4,5-c]pyridin-4-one (A7) (53 mg, 0.1225 mmol) in dichloromethane (2.5 mL) was added 3-chlorobenzenecarboperoxoic acid (72.50 mg, 0.2941 mmol). Solution was stirred for 2 hours at room temperature. Water and dichloromethane were added, and organic layer washed 3 times with 5 ml of a solution 10% NaHSO$_3$, then with a solution of NaOH 1N, dried on magnesium sulfate and concentrated on vacuum. The residue was purified by flash chromatography to give 5-ethyl-2-(7-ethylsulfonyl-6-isoquinolyl)-3-methyl-6-(trifluoromethyl)imidazo[4,5-c]pyridin-4-one (A8) (17 mg, 29%) and 5-ethyl-2-(7-ethylsulfonyl-2-oxido-isoquinolin-2-ium-6-yl)-3-methyl-6-(trifluoromethyl)im idazo[4,5-c]pyridin-4-one (A9) (29 mg, 50%).

5-ethyl-2-(7-ethylsulfonyl-6-isoquinolyl)-3-methyl-6-(trifluoromethyl)imidazo[4,5-c]pyridin-4-one (A8):

$^1$H NMR (400 MHz, CDCl$_3$) δ ppm 1.29 (t, 3 H) 1.41 (t, 3 H) 3.50 (d, 2 H) 3.96 (s, 3 H) 4.26 (q, 2 H) 7.23 (s, 1 H) 7.75- 7.86 (m, 1 H) 7.94- 8.04 (m, 1 H) 8.81- 8.96 (m, 2 H) 9.57 (s, 1 H).

5-ethyl-2-(7-ethylsulfonyl-2-oxido-isoquinolin-2-ium-6-yl)-3-methyl-6-(trifluoromethyl)imidazo[4,5-c]pyridin-4-one (A9):

$^1$H NMR (400 MHz, CDCl$_3$) δ ppm 1.29 (t, 3 H), 1.32-1.32 (m, 1 H), 1.41 (t, 3 H), 3.49 (q, 2 H), 3.93-4.01 (m, 3 H), 3.97 (s, 3 H), 4.26 (q, 2 H), 7.21 (s, 1 H), 7.75- 7.85 (m, 1 H), 7.91 (s, 1 H), 8.34 (dd, 1 H), 8.58 (s, 1 H), 8.89- 8.99 (m, 1 H).

The following Table 3 discloses preferred compounds of the formula I-1b:

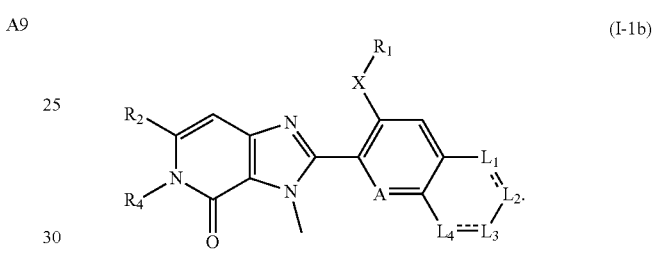

TABLE 3

| Comp. No. | X | $R_1$ | A | $R_2$ | $R_4$ | $L_1$ | $L_2$ | $L_3$ | $L_4$ |
|---|---|---|---|---|---|---|---|---|---|
| A1 (2.133) | S | CH$_2$CH$_3$ | CH | CF$_3$ | CH$_2$CH$_3$ | CH | CH | CH | CH |
| A2 (2.134) | SO$_2$ | CH$_2$CH$_3$ | CH | CF$_3$ | CH$_2$CH$_3$ | CH | CH | CH | CH |
| A3 (2.139) | S | CH$_2$CH$_3$ | N | CF$_3$ | CH$_2$CH$_3$ | CH | CH | CH | CH |
| A4 (2.140) | SO$_2$ | CH$_2$CH$_3$ | N | CF$_3$ | CH$_2$CH$_3$ | CH | CH | CH | CH |
| A5 (2.141) | S | CH$_2$CH$_3$ | CH | CF$_3$ | CH$_2$CH$_3$ | N—CH$_3$ | C—CF$_3$ | N | — |
| A6 (2.142) | SO$_2$ | CH$_2$CH$_3$ | CH | CF$_3$ | CH$_2$CH$_3$ | N—CH$_3$ | C—CF$_3$ | N | — |
| A7 | S | CH$_2$CH$_3$ | CH | CF$_3$ | CH$_2$CH$_3$ | CH | N | CH | CH |
| A8 | SO$_2$ | CH$_2$CH$_3$ | CH | CF$_3$ | CH$_2$CH$_3$ | CH | N | CH | CH |
| A9 | SO$_2$ | CH$_2$CH$_3$ | CH | CF$_3$ | CH$_2$CH$_3$ | CH | N+—O— | CH | CH |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Table 1 to 3 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion—S (1037)+TX, demeton (1038)+TX, demeton-methyl (224)+TX, demeton-O (1038)+TX, demeton-O-methyl (224)+TX, demeton-S (1038)+TX, demeton—S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxath ion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin 11 (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNl-0101 (compound code)+TX, NNl-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and Yl-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122) +TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis (dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of Adoxophyes orana GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, Bacillus firmus (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, Helicoverpa zea NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, Mamestra brassicae NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, Neodiprion sertifer NPV and N. lecontei NPV (575)+TX, *Orius* spp. (596)+TX, *Paecilomyces fumosoroseus* (613)+TX, *Phytoseiulus persimilis* (644)+TX, Spodoptera exigua multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-01 with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure $B_1$ (839)+TX, trimedlure $B_2$ (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056),+TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/ Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/ Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, Bacillus thuringiensis delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion—S (1037)+TX, demeton (1038)+TX, demeton-methyl (224)+TX, demeton-O (1038)+TX, demeton-O-methyl (224)+TX, demeton—S (1038)+TX, demeton—S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, El 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nomicotine (traditional name) (1319)+TX, novaluron (585)+TX, noviflumuron (586)+TX, 0-5-dichloro-4-iodophenyl 0-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1(696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, Sl-0009 (compound code)+TX, Sl-0205 (compound code)+TX, Sl-0404 (compound code)+TX, Sl-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19]+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, a molluscicide selected from the group of substances consisting of bis(tributyltin) oxide (IUPAC name) (913)+TX, bromoacetamide [CON]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, Myrothecium verrucaria composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and Reynoutria sachalinensis extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxo1-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole [60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imiben-conazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+ TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3 ]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-Ll90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1 ,3,4,4a,5,6,6a,12,12a,12b-decahydro-6,12-dihydroxy-4,6a,12b-trimethyl-11-oxo-9-(3-pyrid inyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX;

microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (*Azotomeal*®)+TX, *Azotobacter cysts* (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLe®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®) +TX, *Bacillus thuringiensis kurstaki* (Javelin®+TX, Deliver®+TX, CryMax®+TX, Bonide®+TX, Scutella WP®+TX, Turilav WP+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, *bacteria* spp. (GROWMEND®+TX, GROWSWEET®+TX, Shootup®)+TX, bacteriophage of *Clavipacter michiganensis* (AgriPhage®)+TX, Bakflor®30 TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, Botrytis cineria+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, *Enterobacteriaceae*+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera nucleopolyhedrovirus* (Helicovex®)+TX, *Helicoverpa zea nuclear polyhedrosis* virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar nucleopolyhedrosis* virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua nuclear polyhedrosis* virus (Spod-X®+TX, Spexit®)+TX, *Serratia marcescens*+TX, Serratia plymuthica+TX, *Serratia* spp.+TX, *Sordaria fimicola*+TX, *Spodoptera littoralis nucleopolyhedrovirus* (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX,

*Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly Gliocladium virens GL-21) (SoilGuard®)+TX, *Trichoderma viride*+TX, *Trichoderma viride* strain ICC 080 (Remedier®)+TX, *Trichosporon pullulans*+TX, *Trichosporon* spp.+*TX, Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanfi* (Mycotal®+TX, Vertalec®)+TX, Vip3Aa20 (VIPtera®)+TX, *Virgibaclillus marismortui*+TX, Xanthomonas campestris pv. Poae (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemba)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, *Rutaceae* plant extract (Soleo®)+TX, soybean oil (Ortho ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC-LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable pheromone®)+TX, Peachtree Borer Pheromone (Isomate-P®)+TX, Tomato Pinworm Pheromone (3M Sprayable pheromone®)+TX, Entostat powder (extract from palm tree) (Exosex CM®)+TX, (E+TX,Z+TX,Z)-3 +TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: Aphelinus abdominalis+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius califomicus* (Amblyline®+TX, Spical®)+TX, *Amblyseius cucumeris* (Thripex®)+TX, *Bugline cucumeris*®)+TX, *Amblyseius fallacis* (Fallacis®)+TX, *Amblyseius swirskii* (Bugline swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla camea* (Chrysoline®)+TX, *Chrysoperla camea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus califomicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack+TX, Nematop®)+TX, *Heterorhabditis megidis* (Nemasys H®30 +TX, BioNem H®+TX, Exhibitline hm®+TX, Larvanem-M®)+TX, *Hippodamia convergens*+TX, *Hypoaspis aculeifer*

(Aculeifer-System®)+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-l®+TX, Online i®)+TX, *Orius laevigatus* (Thripor-L®+TX, Oriline I®)+TX, *Orius majusculus* (Online m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys+TX, BioNem+TX, Steinernema-System®+TX, NemAttack®+TX, Nemaplus®+TX, Exhibitline sf®+TX, Scia-rid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (*Guardian Nematodes*®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIB IT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zeno+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Table 1 to 3 with active ingredients described above comprises a compound selected from Table 1 to 3 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Table 1 to 3 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Table 1 to 3 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula I. Further, it is hereby made available, a composition comprising a plant propagation material treated with a compound of formula I.

Seed treatment comprises all suitable seed treatment techniques known in the art, such as seed dressing, seed coating, seed dusting, seed soaking and seed pelleting. The seed treatment application of the compound formula I can be carried out by any known methods, such as spraying or by dusting the seeds before sowing or during the sowing/planting of the seeds.

Biological Examples

Example B1

Bemisia Tabaci (Cotton White Fly):
Feeding/Contact Activity

Cotton leaf discs were placed on agar in 24-well microtiter plates and sprayed with aqueous test solutions prepared from 10,000 ppm DMSO stock solutions. After drying the leaf discs were infested with adult white flies. The samples were checked for mortality 6 days after incubation.

The following compound resulted in at least 80% mortality at an application rate of 200 ppm:

A6.

Example B2

Diabrotica Balteata (Corn root worm)

Maize sprouts placed onto an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm:

A1, A2, A3, A4 and A8.

Example B3

*Euschistus heros* (Neotropical Brown Stink Bug)

Soybean leaves on agar in 24-well microtiter plates were sprayed with aqueous test solutions prepared from 10,000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A1, A2, A4, A5, A6 and A8.

Example B4

*Frankliniella occidentalis* (Western Flower Thrips): Feeding/Contact Activity

Sunflower leaf discs were placed on agar in 24-well microtiter plates and sprayed with aqueous test solutions prepared from 10,000 DMSO stock solutions. After drying the leaf discs were infested with a Frankliniella population of mixed ages. The samples were assessed for mortality 7 days after infestation.

The following compounds resulted in at least 80% mortality at an application rate of 200 ppm:
A2 and A6.

Example B5

*Myzus persicae* (Green Peach Aphid): Feeding/Contact Activity

Sunflower leaf discs were placed onto agar in a 24-well microtiter plate and sprayed with aqueous test solutions prepared from 10,000 ppm DMSO stock solutions. After drying, the leaf discs were infested with an aphid population of mixed ages. The samples were assessed for mortality 6 days after infestation. The following compounds resulted in at least 80% mortality at an application rate of 200 ppm:
A2, A3, A4 and A6

Example B6

*Myzus persicae* (Green Peach Aphid): Systemic Activity

Roots of pea seedlings infested with an aphid population of mixed ages were placed directly into aqueous test solutions prepared from 10,000 DMSO stock solutions. The samples were assessed for mortality 6 days after placing seedlings into test solutions.

The following compounds resulted in at least 80% mortality at a test rate of 24 ppm:
A6 and A9.

Example B7

*Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm:
A1, A2, A3, A4, A6, A8and A9.

Example B8

*Spodoptera littoralis* (Egyptian Cotton Leaf Worm)

Cotton leaf discs were placed onto agar in 24-well microtiter plates and sprayed with aqueous test solutions prepared from 10,000 ppm DMSO stock solutions. After drying the leaf discs were infested with five L1 larvae. The samples were assessed for mortality, anti-feeding effect, and growth inhibition in comparison to untreated samples 3 days after infestation. Control of Spodoptera littoralis by a test sample is given when at least one of the categories mortality, anti-feedant effect, and growth inhibition is higher than the untreated sample.

The following compounds resulted in at least 80% control at an application rate of 200 ppm:
A1, A2, A3, A4, A5, A6, A8 and A9.

Example B9

*Spodoptera littoralis* (Egyptian Cotton Leaf Worm)

Test compounds were applied by pipette from 10,000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. Spodoptera eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm:
A2, A4 and A6.

Example B10

*Tetranychus urticae* (Two-spotted Spider Mite): Feeding/Contact Activity

Bean leaf discs on agar in 24-well microtiter plates were sprayed with aqueous test solutions prepared from 10,000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm:
A2 and A4.

Example B11

*Aedes aegypti* (Yellow Fever Mosquito)

Test solutions, at an application rate of 200ppm in ethanol, were applied to 12 well tissue culture plates. Once the deposits were dry, five, two to five day old adult female Aedes aegypti were added to each well, and sustained with a 10% sucrose solution in a cotton wool plug. Assessment of knockdown was made one hour after introduction, and mortality was assessed at 24 and 48 hours after introduction.

The following compounds gave at least 80% control of Aedes aegypti after 48 h and/or 24 h:
A2, A4 and A6.

The invention claimed is:
1. A compound of formula I

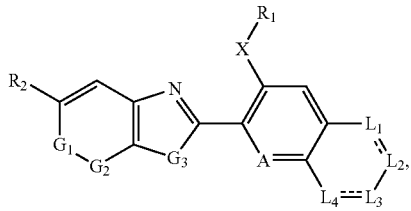

(I)

wherein
A is CH or N;
X is S, SO or $SO_2$;
$R_1$ is $C_1$-$C_6$ alkyl, $C_2$-$C_6$ alkenyl, $C_2$-$C_6$haloalkenyl, $C_2$-$C_6$alkynyl, $C_1$-$C_4$ haloalkyl, $C_3$-$C_6$ cycloalkyl, $C_3$-$C_6$cycloalkyl-$C_1$-$C_4$ alkyl; or is $C_3$-$C_6$ cycloalkyl mono- or polysubstituted by substituents selected from the group consisting of halogen, cyano, $C_1$-$C_4$ haloalkyl and $C_1$-$C_4$alkyl; or is $C_3$-$C_6$ cycloalkyl-$C_1$-$C_4$ alkyl mono- or polysubstituted by substituents selected from the group consisting of halogen, cyano, $C_1$-$C_4$ haloalkyl and $C_1$-$C_4$alkyl;
$R_2$ is hydrogen, halogen, $C_1$-$C_4$ haloalkylsulfanyl, $C_1$-$C_4$haloalkylsulfinyl, $C_1$-$C_4$ haloalkylsulfonyl, O($C_1$-$C_4$haloalkyl), —$SF_5$, —C(O)$C_1$-$C_4$ haloalkyl, cyano, $C_1$-$C_6$haloalkyl or is $C_1$-$C_6$ haloalkyl substituted by one or two substituents selected from the group consisting of hydroxyl, methoxy and cyano; or is $C_3$-$C_6$ cycloalkyl which can be mono- or polysubstituted by substituents selected from the group consisting of halogen, cyano, $C_1$-$C_4$ haloalkyl and $C_1$-$C_4$ alkyl;
$G_1$ is $NR_4$ and $G_2$ is C(Y); or
$G_1$ is C(Y) and $G_2$ is $NR_6$;
Y is O or S;
$G_3$ is $NR_6$;
$R_6$ is $C_1$-$C_4$ alkyl which can be mono- or polysubstituted by substituents selected from the group consisting of halogen and $C_1$-$C_2$ alkylsulfinyl;
$R_4$ is hydrogen, $C_1$-$C_6$ alkyl, $C_1$-$C_6$ haloalkyl, or are $C_3$-$C_6$cycloalkyl which can be mono- or polysubstituted by $R_7$,or is $C_3$-$C_6$ cycloalkyl-$C_1$-$C_4$ alkyl which can be mono-or polysubstituted by $R_7$, or
$R_4$ is $C_1$-$C_4$ alkyl substituted by cyano, $C_1$-$C_4$alkylsulfanyl, $C_1$-$C_4$ alkylsulfonyl, $C_1$-$C_4$ alkylsulfinyl,
$C_1$-$C_4$ alkoxy, $C_1$-$C_4$ alkoxy $C_1$-$C_4$ alkoxy, $C_3$-$C_6$ cycloalkyl or by phenyl which itself can be mono- or polysubstituted by substituents selected from the group consisting of halogen, $C_1$-$C_4$ alkyl, $C_1$-$C_4$ haloalkyl and $C_1$-$C_4$ alkoxy; or
$R_4$ is $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxy, $C_1$-$C_6$ alkoxy, $C_1$-$C_4$alkoxy $C_1$-$C_4$ alkyl $C_1$-$C_6$alkylsulfanyl, $C_1$-$C_4$ alkylsulfonyl, $C_1$-$C_6$ alkylsulfinyl, $C_1$-$C_6$ haloalkylsulfanyl, $C_1$-$C_6$haloalkylsulfonyl, $C_1$-$C_6$ haloalkylsulfinyl, amine or hydroxyl; or
$R_4$ is $C_2$-$C_6$ alkenyl substituted by $R_{11}$ or $C_2$-$C_6$ alkynyl substituted by $R_{11}$; or
$R_4$ is a five- to six-membered, aromatic, partially saturated or fully saturated ring system, said ring system can be mono- or polysubstituted by substituents selected from the group consisting of halogen, cyano, nitro, $C_2$-$C_6$ alkenyl, $C_2$-$C_6$ haloalkenyl, $C_2$-$C_6$ alkynyl, $C_2$-$C_6$ haloalkynyl, $C_1$-$C_4$ alkoxy $C_1$-$C_4$ alkyl, $C_1$-$C_4$ alkyl, $C_1$-$C_4$ haloalkyl, $C_1$-$C_4$ haloalkoxy, $C_1$-$C_4$ alkoxy, $C_1$-$C_4$alkylsulfanyl, $C_1$-$C_4$ alkylsulfinyl, $C_1$-$C_4$ alkylsulfonyl and —C(O)$C_1$-$C_4$ alkyl, $C_1$-$C_4$ haloalkylsulfanyl, $C_1$-$C_4$haloalkylsulfinyl, $C_1$-$C_4$ haloalkylsulfonyl and —C(O)$C_1$-$C_4$ haloalkyl; and said ring system can contain 1, 2 or 3 heteroatoms selected from the group consisting of nitrogen, oxygen and sulphur, where said ring system may not contain more than one oxygen atom and not more than one sulfur atom;
$R_5$ is hydrogen, $C_1$-$C_6$ alkyl, $C_1$-$C_6$ haloalkyl, or are $C_3$-$C_6$cycloalkyl which can be mono- or polysubstituted by $R_7$,or are $C_3$-$C_6$ cycloalkyl-$C_1$-$C_4$ alkyl which can be mono- or polysubstituted by $R_7$, or
$R_5$ is $C_1$-$C_4$ alkyl substituted by cyano, $C_1$-$C_4$alkylsulfanyl, $C_1$-$C_4$ alkylsulfonyl, $C_1$-$C_4$ alkylsulfinyl,
$C_1$-$C_4$ alkoxy, $C_1$-$C_4$ alkoxy $C_1$-$C_4$ alkoxy, $C_3$-$C_6$ cycloalkyl or by phenyl which itself can be mono- or polysubstituted by substituents selected from the group consisting of halogen, $C_1$-$C_4$ alkyl, $C_1$-$C_4$ haloalkyl and $C_1$-$C_4$ alkoxy; or
$R_5$ is $C_2$-$C_6$ alkenyl, $C_2$-$C_6$ haloalkenyl, $C_2$-$C_6$ alkynyl, $C_2$-$C_6$ haloalkynyl, $C_1$-$C_6$ haloalkoxy, $C_1$-$C_6$ alkoxy, $C_1$-$C_4$alkoxy $C_1$-$C_4$ alkyl $C_1$-$C_6$ alkylsulfanyl, $C_1$-$C_4$ alkylsulfonyl, $C_1$-$C_6$ alkylsulfinyl, $C_1$-$C_6$ haloalkylsulfanyl, $C_1$-$C_6$haloalkylsulfonyl, $C_1$-$C_6$ haloalkylsulfinyl, amine or hydroxyl; or
$R_5$ is $C_2$-$C_6$ alkenyl substituted by $R_{11}$ or $C_2$-$C_6$ alkynyl substituted by $R_{11}$; or
$R_5$ is a five- to six-membered, aromatic, partially saturated or fully saturated ring system, said ring system can be mono- or polysubstituted by substituents selected from the group consisting of halogen, cyano, nitro, $C_2$-$C_6$ alkenyl, $C_2$-$C_6$ haloalkenyl, $C_2$-$C_6$ alkynyl, $C_2$-$C_6$ haloalkynyl, $C_1$-$C_4$ alkoxy $C_1$-$C_4$ alkyl, $C_1$-$C_4$ alkyl, $C_1$-$C_4$ haloalkyl, $C_1$-$C_4$ haloalkoxy, $C_1$-$C_4$ alkoxy, $C_1$-$C_4$alkylsulfanyl, $C_1$-$C_4$ alkylsulfinyl, $C_1$-$C_4$ alkylsulfonyl and —C(O)$C_1$-$C_4$ alkyl, $C_1$-$C_4$ haloalkylsulfanyl, $C_1$-$C_4$haloalkylsulfinyl, $C_1$-$C_4$ haloalkylsulfonyl and
—C(O)$C_1$-$C_4$ haloalkyl; and said ring system can contain 1, 2 or 3 heteroatoms selected from the group consisting of nitrogen, oxygen and sulphur, where said ring system may not contain more than one oxygen atom and not more than one sulfur atom;
$R_7$ is cyano, halogen, $C_1$-$C_6$ alkyl or $C_1$-$C_4$ haloalkyl;
$L_1$, $L_2$, $L_3$ and $L_4$ form together with the two carbon atoms to which $L_1$ and $L_4$ are attached, an aromatic, partially saturated or fully saturated carbocyclic or heterocyclic ring system; wherein
$L_1$ is nitrogen, S(O)n, oxygen, N—$R_{10a}$ or C($R_{10a}$)$_m$;
$L_2$ is nitrogen, S(O)n, oxygen, N—$R_{10b}$ or C($R_{10b}$)$_m$;
$L_3$ is nitrogen, S(O)n, oxygen, N—$R_{10c}$, or C($R_{10c}$)$_m$;
$L_4$ is nitrogen, S(O)n, oxygen, a direct bond, N—$R_{10d}$ or C($R_{10d}$)$_m$; with the provisos that no more than 2 substituents selected from $L_1$, $L_2$, $L_3$ and $L_4$ can be oxygen or sulfur;
and if two L groups are oxygen, they are not adjacent to each other; and no more than three L groups can be nitrogen;
n is 0, 1 or 2;
m is 1 or 2;
$R_{10a}$, $R_{10b}$, $R_{10c}$, and $R_{10d}$ independently from each other, are hydrogen, halogen, nitro, cyano, hydroxyl, $C_1$-$C_6$alkyl, $C_2$-$C_6$ alkenyl, $C_2$-$C_6$ alkynyl, $C_3$-$C_6$ cycloalkyl, $C_1$-$C_6$haloalkyl, $C_2$-$C_6$ haloalkenyl, $C_2$-$C_6$ haloalkynyl, $C_3$-$C_6$halocycloalkyl, $C_1$-$C_6$ alkoxy, $C_1$-$C_4$ alkoxy $C_1$-$C_4$ alkyl, $C_1$-$C_6$haloalkoxy, $C_1$-$C_6$ alkylthio, $C_1$-$C_6$ alkylsulfinyl, $C_1$-$C_6$alkylsulfonyl, $C_1$-$C_6$ haloalkylthio, $C_1$-$C_6$ haloalkylsulfinyl, $C_1$-$C_6$ haloalkylsulfonyl, $C_2$-$C_6$ alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$ alkyl)NH, ($C_1$-$C_6$ alkyl)$_2$N, ($C_1$-$C_6$ cycloalkyl)NH, ($C_1$-$C_6$ cycloalkyl)$_2$N, $C_1$-$C_6$alkylcarbonylamino, $C_1$-$C_6$ cycloalkylcarbonylamino or —$SF_5$;

additionally one of $R_{10a}$, $R_{10b}$, $R_{10c}$ and $R_{10d}$ can be oxo; or $R_{10a}$, $R_{10b}$, $R_{10c}$, and $R_{10d}$, independently from each other, are $C_3$-$C_6$ cycloalkyl mono- to polysubstituted by substituents selected from the group consisting of halogen, $C_1$-$C_4$ haloalkyl, $C_1$-$C_4$ alkyl and cyano; or $R_{10a}$, $R_{10b}$, $R_{10c}$, and $R_{10d}$, independently from each other, are phenyl witch can be mono- to polysubstituted by substituents selected from the group consisting of halogen, $C_1$-$C_4$ haloalkyl, $C_1$-$C_4$ alkyl and cyano; and $R_{11}$ is nitro, phenyl, cyano, $C_1$-$C_4$ alkoxy, $C_1$-$C_4$ alkoxy $C_1$-$C_4$ alkoxy, $C_1$-$C_4$ alkylsulfanyl, $C_1$-$C_4$ alkylsulfonyl, $C_1$-$C_4$alkylsulfinyl, $C_1$-$C_4$ haloalkylsulfanyl, $C_1$-$C_4$haloalkylsulfonyl or $C_1$-$C_4$ haloalkylsulfinyl;

or an agrochemically acceptable salt, stereoisomer, enantiomer, tautomer or N-oxide thereof.

2. A compound of formula I according to claim 1, represented by the compounds of formula I-1

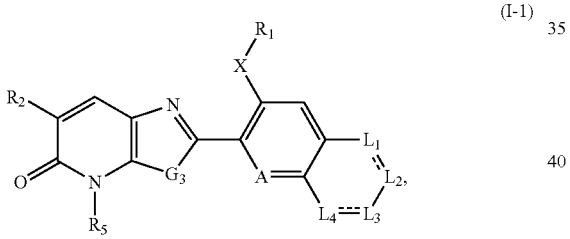

(I-1)

wherein the substituents X, A, $R_1$, $R_2$, $R_5$, $G_3$, $L_1$, $L_2$, $L_3$ and $L_4$ are as defined under formula I in claim 1.

3. A compound of formula I-1 according to claim 2, wherein

A is C—H or N;

$R_1$ is $C_1$-$C_4$ alkyl, $C_3$-$C_6$ cycloalkyl-$C_1$-$C_4$ alkyl or $C_3$-$C_6$ cycloalkyl;

$R_2$ is halogen, $C_1$-$C_4$ haloalkylsulfanyl, $C_1$-$C_4$haloalkylsulfinyl, $C_1$-$C_4$ haloalkylsulfonyl, $C_1$-$C_4$haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$ alkyl; and $R_{10a}$, $R_{10b}$, $R_{10c}$, and $R_{10d}$, independently from each other, are hydrogen, halogen, nitro, cyano, hydroxyl, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl-$C_1$-C4 cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_3$-$C_6$cyclohaloalkyl-$C_1$-$C_4$ cycloalkyl, $C_1$-$C_6$ alkoxy, $C_1$-$C_6$haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$haloalkylsulfinyl, $C_1$-$C_4$ haloalkylsulfonyl, C2-C4 alkylcarbonyl, $C_2$-$C_6$ alkoxycarbonyl or —$SF_5$, additionally one of $R_{10a}$, $R_{10b}$, $R_{10c}$ and $R_{10d}$ can be oxo.

4. A compound of formula I according to claim 1, represented by the compounds of formula I-1 a

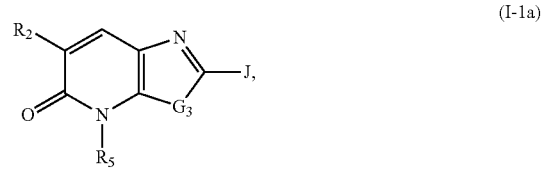

(I-1a)

wherein J is selected from the group consisting of

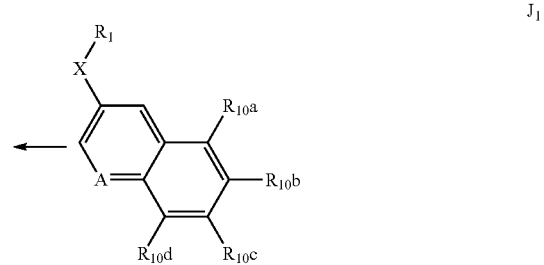

$J_1$

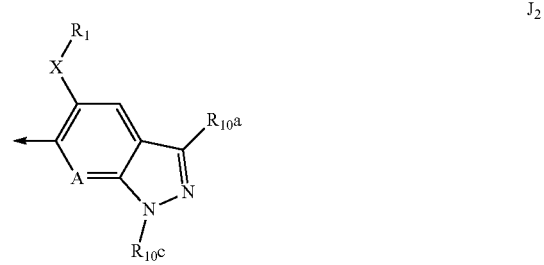

$J_2$

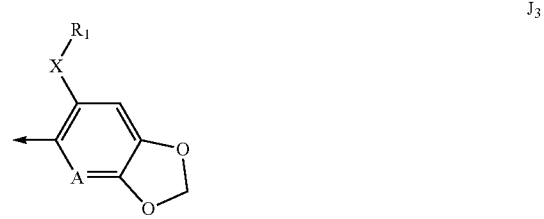

$J_3$

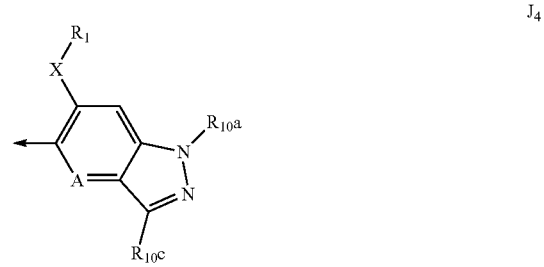

$J_4$

121
-continued
J₅
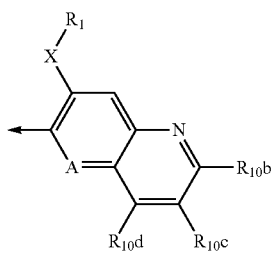
J₆
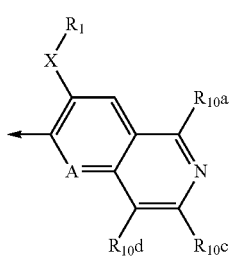
J₇
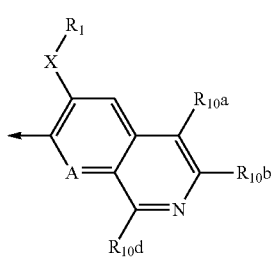
J₈
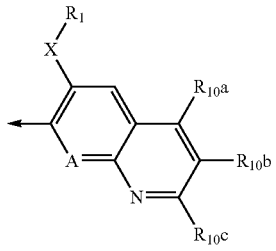
J₉
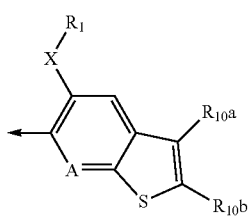
J₁₀
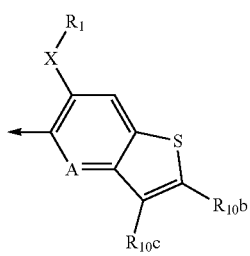
122
-continued
J₁₁
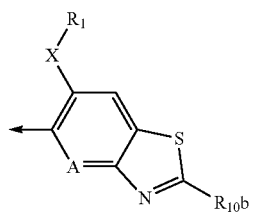
J₁₂
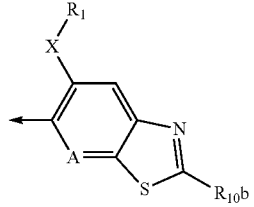
J₁₃
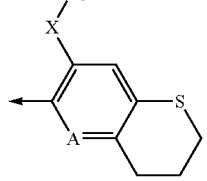
J₁₄
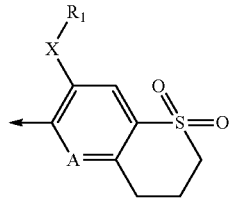
J₁₅
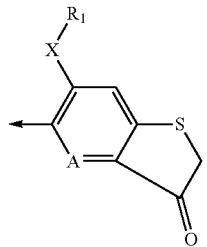
J₁₆
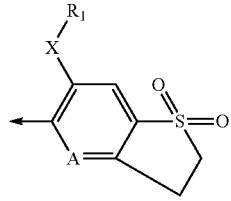
J₁₇
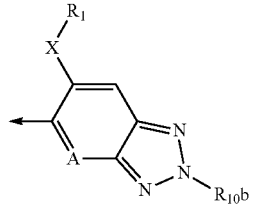

-continued

J₁₈ 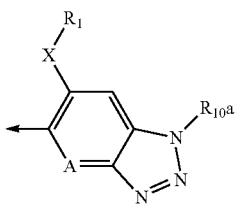

J₁₉ 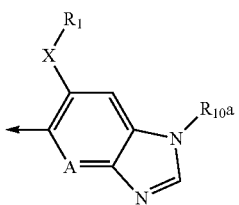

J₂₀ 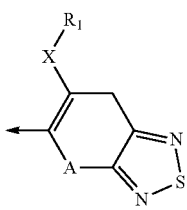

J₂₁ 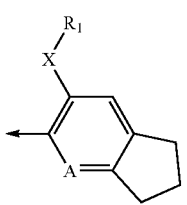

J₂₂ 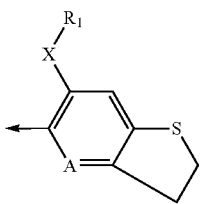

J₂₃ 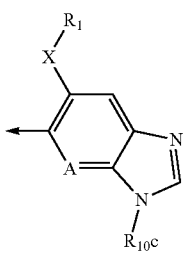

J₂₄ 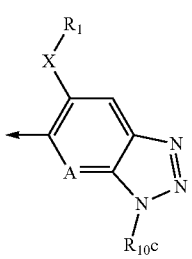

-continued

J₂₅ 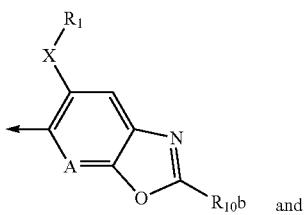 and

J₂₆ 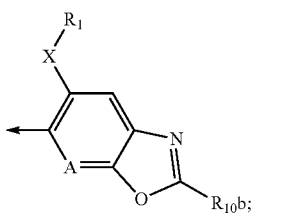;

A is C—H or N;

R₁ is $C_1$-$C_4$ alkyl, $C_3$-$C_6$ cycloalkyl-$C_1$-$C_4$ alkyl or $C_3$-$C_6$ cycloalkyl;

R₂ is halogen, $C_1$-$C_4$ haloalkylsulfanyl, $C_1$-$C_4$haloalkylsulfinyl, $C_1$-$C_4$ haloalkylsulfonyl, $C_1$-$C_4$haloalkoxy, $C_1$-$C_4$ haloalkyl, cyano or is $C_3$-$C_6$cycloalkyl which can be mono- or polysubstituted by substituents selected from the group consisting of halogen, cyano and $C_1$-$C_4$ alkyl;

R₅ is hydrogen, $C_1$-$C_6$ alkyl, $C_1$-$C_6$ haloalkyl, or are $C_3$-$C_6$ cycloalkyl which can be mono- or poly substituted by R₇, or are $C_3$-$C_6$ cycloalkyl-$C_1$-$C_4$alkyl which can be mono- or polysubstituted by R₇;

or R₅ is $C_1$-$C_4$ alkyl substituted by cyano or by phenyl which itself can be mono-or polysubstituted by substituents selected from the group consisting of halogen, $C_1$-$C_4$ alkyl, $C_1$-$C_4$haloalkyl and $C_1$-$C_4$ alkoxy; or R₅ is $C_2$-$C_6$ alkenyl, $C_2$-$C_6$ haloalkenyl, $C_2$-$C_6$alkynyl, $C_2$-$C_6$ haloalkynyl, $C_1$-$C_6$ haloalkoxy, $C_1$-$C_6$alkoxy, $C_1$-$C_6$ alkylsulfanyl, $C_1$-$C_4$ alkylsulfonyl, $C_1$-$C_6$ alkylsulfinyl, $C_1$-$C_6$ haloalkylsulfanyl, $C_1$-$C_6$haloalkylsulfonyl, $C_1$-$C_6$ haloalkylsulfinyl, amine or hydroxyl;

R₇ is cyano, halogen or $C_1$-$C_2$ haloalkyl;

X is S, SO or $SO_2$;

G₃ is NR₆;

R₆ is $C_1$-$C_4$ alkyl which can be mono- or polysubstituted by substituents selected from the group consisting of halogen and $C_1$-$C_2$alkylsulfinyl; and $R_{10a}$, $R_{10b}$, $R_{10c}$, and $R_{10d}$, independently from each other, are hydrogen, halogen, nitro, cyano, hydroxyl, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl-$C_1$-$C_4$ cycloalkyl, $C_1$-$C_6$ haloalkyl, $C_2$-$C_6$ haloalkenyl, $C_2$-$C_6$haloalkynyl, $C_3$-$C_6$ halocycloalkyl, $C_3$-$C_6$cyclohaloalkyl- $C_1$-$C_4$ cycloalkyl, $C_1$-$C_6$ alkoxy, $C_1$-$C_6$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$haloalkylsulfinyl, $C_1$-$C_4$ haloalkylsulfonyl, $C_2$-$C_4$alkylcarbonyl, $C_2$-$C_6$ alkoxycarbonyl or —$SF_5$; additionally one of $R_{10a}$, $R_{10b}$, $R_{10c}$ and $R_{10d}$ oxo.

5. A compound of formula I according to claim 1, represented by the compounds of formula I-2

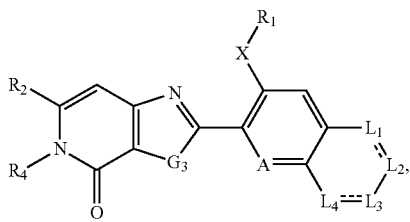
(I-2)

wherein the substituents X, A, $R_1$, $R_2$, $R_4$, $G_3$, $L_1$, $L_2$, $L_3$ and $L_4$ are as defined under formula I in claim 1.

6. A compound of formula I-1 according to claim 5, wherein

A is C—H or N;

$R_1$ is $C_1$-$C_4$ alkyl, $C_3$-$C_6$ cycloalkyl-$C_1$-$C_4$ alkyl or $C_3$-$C_6$ cycloalkyl;

$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$ cycloalkyl which can be mono- or polysubstituted by substituents selected from the group consisting of halogen, cyano and $C_1$-$C_4$ alkyl; and $R_{10a}$, $R_{10b}$, $R_{10c}$, and $R_{10d}$, independently from each other, are hydrogen, halogen, nitro, cyano, hydroxyl, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl-$C_1$-$C_4$ cycloalkyl, $C_1$-$C_6$ haloalkyl, $C_2$-$C_6$ haloalkenyl, $C_2$-$C_6$ haloalkynyl, $C_3$-$C_6$ halocycloalkyl, $C_3$-$C_6$ cyclohaloalkyl-$C_1$-$C_4$ cycloalkyl, $C_1$-$C_6$ alkoxy, $C_1$-$C_6$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$ haloalkylsulfinyl, $C_1$-$C_4$ haloalkylsulfonyl, $C_2$-$C_4$ alkylcarbonyl, $C_2$-$C_6$ alkoxycarbonyl or —SF$_5$; additionally one of $R_{10a}$, $R_{10b}$, $R_{10c}$ and $R_{10b}$ can be oxo.

7. A compound of formula I according to claim 1, represented by the compounds of formula I-2a

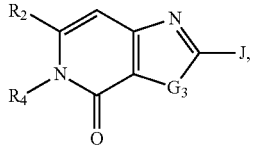
(I-2a)

wherein J is selected from the group consisting of

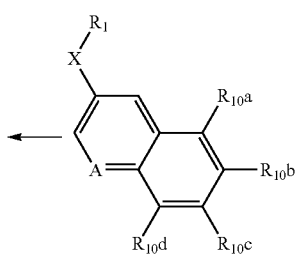
$J_1$

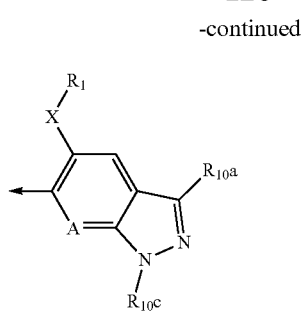
$J_2$

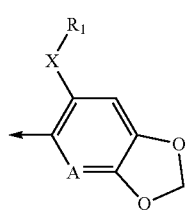
$J_3$

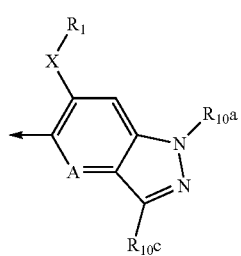
$J_4$

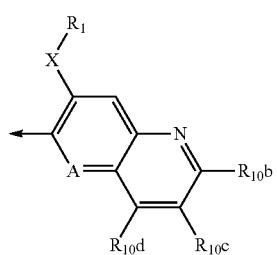
$J_5$

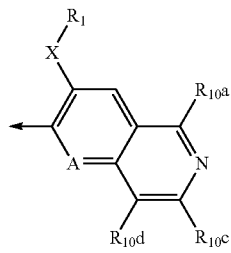
$J_6$

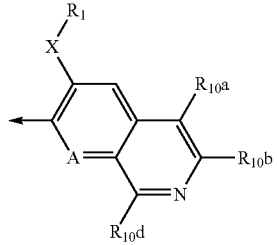
$J_7$

J8
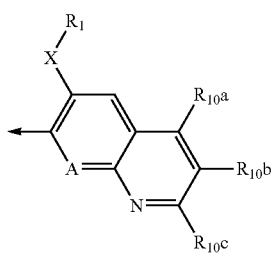
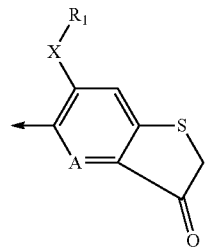
J15
J9
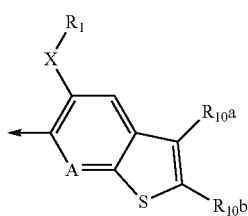
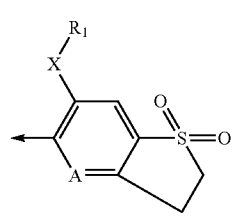
J16
J10
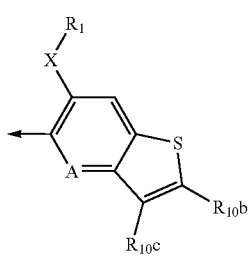
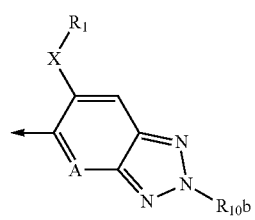
J17
J11
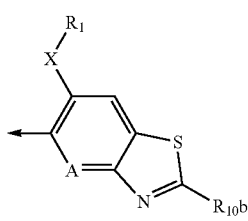
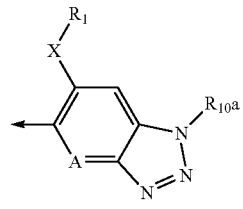
J18
J12
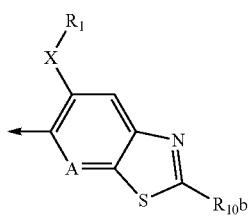
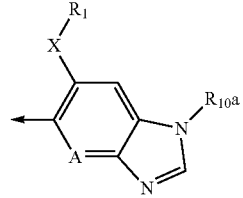
J19
J13
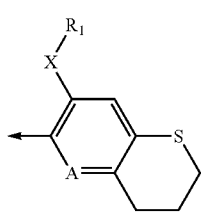
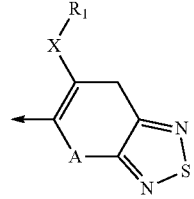
J20
J14
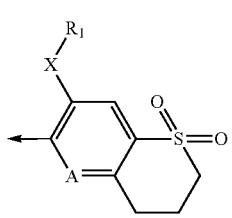
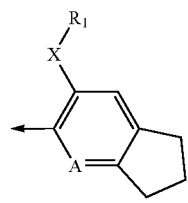
J21

-continued

J22 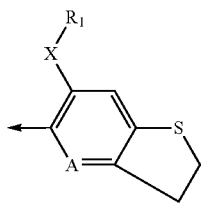

J23 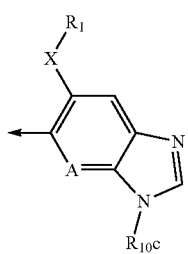

J24 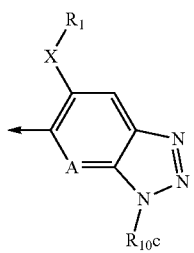

J25 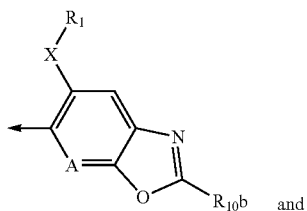 and

J26 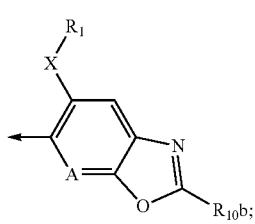;

A is C—H or N;

$R_1$ is $C_1$-$C_4$ alkyl, $C_3$-$C_6$ cycloalkyl-$C_1$-$C_4$ alkyl or $C_3$-$C_6$ cycloalkyl;

$R_2$ is halogen, $C_1$-$C_4$ haloalkylsulfanyl, $C_1$-$C_4$ haloalkylsulfinyl, $C_1$-$C_4$ haloalkylsulfonyl, $C_1$-$C_4$ haloalkoxy, $C_1$-$C_4$ haloalkyl, cyano or is $C_3$-$C_6$ cycloalkyl which can be mono- or polysubstituted by substituents selected from the group consisting of halogen, cyano and $C_1$-$C_4$ alkyl;

$R_4$ is hydrogen, $C_1$-$C_6$ alkyl, $C_1$-$C_6$ haloalkyl, or are $C_3$-$C_6$ cycloalkyl which can be mono- or poly substituted by $R_7$; or are $C_3$-$C_6$ cycloalkyl-$C_1$-$C_4$alkyl which can be mono- or polysubstituted by $R_7$; or $R_4$ is $C_1$-$C_4$ alkyl substituted by cyano or by phenyl which itself can be mono- or polysubstituted by substituents selected from the group consisting of halogen, $C_1$-$C_4$ alkyl, $C_1$-$C_4$ haloalkyl and $C_1$-$C_4$alkoxy; or $R_4$ is $C_2$-$C_6$ alkenyl, $C_2$-$C_6$ haloalkenyl, $C_2$-$C_6$alkynyl, $C_2$-$C_6$ haloalkynyl, $C_1$-$C_6$ haloalkoxy, $C_1$-$C_6$alkoxy, $C_1$-$C_6$ alkylsulfanyl, $C_1$-$C_4$ alkylsulfonyl, $C_1$-$C_6$ alkylsulfinyl, $C_1$-$C_6$ haloalkylsulfanyl, $C_1$-$C_6$haloalkylsulfonyl, $C_1$-$C_6$ haloalkylsulfinyl, amine or hydroxyl;

$R_7$ is cyano, halogen or $C_1$-$C_2$ haloalkyl;

X is S, SO or $SO_2$;

$G_3$ is $NR_6$;

$R_6$ is $C_1$-$C_4$ alkyl which can be mono- or polysubstituted by substituents selected from the group consisting of halogen and $C_1$-$C_2$alkylsulfinyl; and $R_{10a}$, $R_{10b}$, $R_{10c}$, and $R_{10d}$, independently from each other, are hydrogen, halogen, nitro, cyano, hydroxyl, $C_1$-$C_6$ alkyl, $C_2$-$C_6$ alkenyl, $C_2$-$C_6$ alkynyl, $C_3$-$C_6$ cycloalkyl, $C_3$-$C_6$ cycloalkyl-$C_1$-$C_4$ cycloalkyl, $C_1$-$C_6$ haloalkyl, $C_2$-$C_6$ haloalkenyl, $C_2$-$C_6$haloalkynyl, $C_3$-$C_6$ halocycloalkyl, $C_3$-$C_6$cyclohaloalkyl- $C_1$-$C_4$ cycloalkyl, $C_1$-$C_6$ alkoxy, $C_1$-$C_6$ haloalkoxy, $C_1$-$C_4$ alkylthio, $C_1$-$C_4$ alkylsulfinyl, $C_1$-$C_4$ alkylsulfonyl, $C_1$-$C_4$ haloalkylthio, $C_1$-$C_4$haloalkylsulfinyl, $C_1$-$C_4$ haloalkylsulfonyl, $C_2$-$C_4$alkylcarbonyl, $C_2$-$C_6$ alkoxycarbonyl or —$SF_5$; additionally one of $R_{10a}$, $R_{10b}$, $R_{10c}$ and $R_{10d}$ can be oxo.

8. A compound of formula I according to claim 1, represented by the compounds of formula I-2a

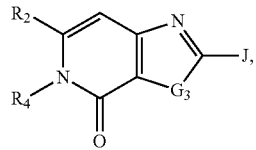

(I-2a)

wherein J is selected from the group consisting of

J1 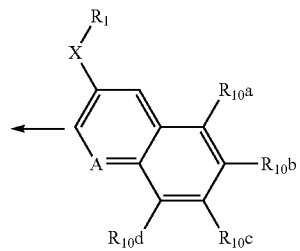

J6 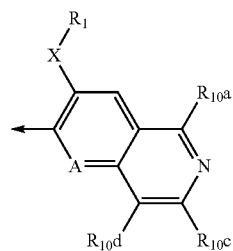

J19b 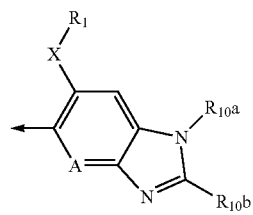

wherein
A is CH or N;
$R_2$ is $C_1$-$C_2$haloalkyl;
$R_4$ is $C_1$-$C_4$ alkyl; and
$R_{10a}$, $R_{10b}$, $R_{10c}$, and $R_{10d}$, independently from each other, are hydrogen, $C_1$-$C_2$ haloalkyl or $C_1$-$C_2$alkyl.

9. A compound of formula I according to claim 1, represented by the compounds of formula I-2a

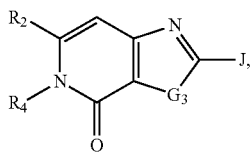
(I-2a)

wherein J is selected from the group consisting of

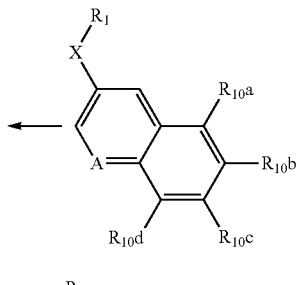
$J_1$

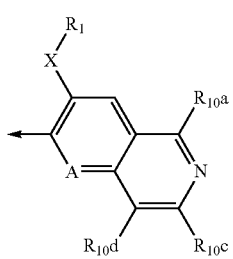
$J_6$

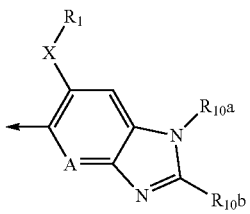
$J_{19b}$ wherein
A is CH or N;
$R_2$ is trifluoromethyl;
$R_4$ is methyl or ethyl; and
$R_{10a}$, $R_{10b}$, $R_{10c}$, and $R_{10d}$, independently from each other, are hydrogen, trifluoromethyl or methyl.

10. A pesticidal composition, which comprises at least one compound of formula I according to claim 1 or, where appropriate, a tautomer thereof, in each case in free form or in agrochemic ally utilizable salt form, as active ingredient and at least one auxiliary.

11. A method for controlling pests, which comprises applying a composition according to claim 10 to the pests or their environment with the exception of a method for treatment of the human or animal body by surgery or therapy and diagnostic methods practised on the human or animal body.

12. A method for the protection of seeds from the attack by pests, which comprises treating the seeds or the site, where the seeds are planted, with a composition according to claim 10.

13. The compound of claim 1, wherein X is SO or $SO_2$.

14. The compound of claim 1, wherein A is N.

15. The compound of claim 1, wherein $G_1$ is $NR_4$ and $G_2$ is C(Y).

16. The compound of claim 1, wherein $R_5$ is not hydrogen.

17. The compound of claim 1, wherein $R_6$ is not methyl.

* * * * *